(12) United States Patent
Bettati et al.

(10) Patent No.: US 6,936,608 B2
(45) Date of Patent: *Aug. 30, 2005

(54) IMIDAZO-TRIAZINE DERIVATIVES AS LIGANDS FOR GABA RECEPTORS

(75) Inventors: Michela Bettati, Sawbridgeworth (GB); Peter Blurton, Welwyn Garden (GB); William Robert Carling, Bishops Stortford (GB); Mark Stuart Chambers, Puckeridge (GB); David James Hallett, Watford (GB); Andrew Jennings, Sawbridgworth (GB); Richard Thomas Lewis, Bishop's Stortford (GB); Michael Geoffrey Neil Russell, Welwyn Garden (GB); Leslie Joseph Street, Little Hallingbury (GB); Helen Jane Szekeres, Roydon (GB); Monique Bodil Van Neil, Welwyn Garden (GB)

(73) Assignee: Merck Sharp & Dohme Ltd., Hoddesdon ( * ) Notice: Subject to any disclaimer, the term of this patent is extended or adjusted under 35 U.S.C. 154(b) by 40 days.

This patent is subject to a terminal disclaimer.

(21) Appl. No.: 10/416,318

(22) PCT Filed: Nov. 8, 2001

(86) PCT No.: PCT/GB01/04948

§ 371 (c)(1), (2), (4) Date: May 8, 2003

(87) PCT Pub. No.: WO02/38568

PCT Pub. Date: May 16, 2002

(65) Prior Publication Data

US 2004/0023964 A1 Feb. 5, 2004

(30) Foreign Application Priority Data

Nov. 10, 2000 (GB) ............................................. 0027562
Jul. 16, 2001 (GB) ............................................. 0117277

(51) Int. Cl.$^7$ ...................... C07D 487/04; A61K 31/53; A61P 25/08; A61P 25/22; A61P 25/28
(52) U.S. Cl. ....................................... 514/243; 544/184
(58) Field of Search ........................... 544/184; 514/243

(56) References Cited

U.S. PATENT DOCUMENTS

| | | | |
|---|---|---|---|
| 3,433,194 A | | 3/1969 | Loev |
| 6,617,326 B2 | * | 9/2003 | Carling et al. .............. 514/243 |
| 6,696,444 B2 | * | 2/2004 | Carling et al. .............. 514/243 |

FOREIGN PATENT DOCUMENTS

| | | |
|---|---|---|
| WO | WO 00 78728 | 12/2000 |

OTHER PUBLICATIONS

Scott et al. Prog. Med. Chem. 36: 169–200, 1999.*

* cited by examiner

Primary Examiner—Venkataraman Balasubramanian
(74) Attorney, Agent, or Firm—J. Eric Thies; Melvin Winokur

(57) ABSTRACT

A class of 7-phenylimidazo[1,2-b][1,2,4]triazine derivatives, substituted at the meta position of the phenyl ring by an optionally substituted aryl or heteroaryl group which is directly attached or bridged by an oxygen atom or a —NH— linkage, being selective ligands for GABA$_A$ receptors, in particular having good affinity for the α2 and/or α3 and/or α5 subunit thereof, are accordingly of benefit in the treatment and/or prevention of adverse conditions of the central nervous system, including anxiety, convulsions and cognitive disorders.

17 Claims, No Drawings

IMIDAZO-TRIAZINE DERIVATIVES AS LIGANDS FOR GABA RECEPTORS

CROSS REFERENCE TO RELATED APPLICATIONS

This application is a U.S. National Phase application under 35 U.S.C. § 371 of PCT Application No. PCT/GB01/04948, filed Nov. 8, 2001, which claims priority under 35 U.S.C. § 119 from GB Application No. 0027562.8, filed Nov. 10, 2000, and GB Application No. 0117277.4, filed Jul. 16, 2001.

The present invention relates to a class of substituted imidazo-triazine derivatives and to their use in therapy. More particularly, this invention is concerned with imidazo[1,2-b][1,2,4]triazine analogues which are substituted in the 7-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta\gamma1$, $\alpha2\beta2/3\gamma2$, $\alpha3\beta\gamma2/3$, $\alpha4\beta\delta$, $\alpha5\beta3\gamma2/3$, $\alpha6\beta\gamma2$ and $\alpha6\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Moreover, agents which are inverse agonists of the $\alpha5$ subunit are likely to be beneficial in enhancing cognition, for example in subjects suffering from dementing conditions such as Alzheimer's disease. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse and dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

The present invention provides a class of imidazo-triazine derivatives which possess desirable binding properties at various GABA$_A$ receptor subtypes. The compounds in accordance with the present invention have good affinity as ligands for the α2 and/or α3 and/or α5 subunit of the human GABA$_A$ receptor. The compounds of this invention may interact more favourably with the α2 and/or α3 subunit than with the α1 subunit; and/or may interact more favourably with the α5 subunit than with the α1 subunit.

The compounds of the present invention are GABA$_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

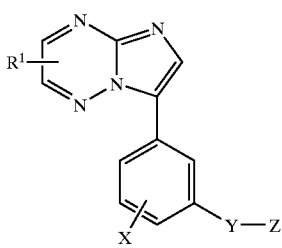

(I)

wherein

X represents hydrogen or halogen;

Y represents a chemical bond, an oxygen atom, or a —NH— linkage;

Z represents an optionally substituted aryl or heteroaryl group;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

The aryl or heteroaryl group Z in the compounds of formula I above may be unsubstituted, or substituted by one or more substituents. For example, the group Z may be unsubstituted, or substituted by one, two or three substituents. Typically, the group Z will be unsubstituted, or substituted by one or two substituents. Suitably, the group Z is unsubstituted or monosubstituted. In a particular embodiment, Z is substituted by two substituents.

Suitable substituents on the group Z include C$_{1-6}$ alkyl, halogen, trifluoromethyl, hydroxy, hydroxy(C$_{1-6}$)alkyl, C$_{1-6}$ alkoxy, nitro, cyano, carboxyethenyl, C$_{2-6}$ alkoxycarbonyl, formyl, C$_{2-6}$ alkylcarbonyl, C$_{1-8}$ alkylthio, C$_{1-6}$ alkylsulphonyl, amino, C$_{2-6}$ alkylcarbonylamino, aminocarbonyl, di(C$_{1-6}$)alkylaminocarbonyl and —CR$^a$=NOR$^b$.

Representative substituents on the group Z include C$_{1-6}$ alkyl, halogen, hydroxy, hydroxy(C$_{1-6}$)alkyl, C$_{1-6}$ alkoxy, nitro, cyano, carboxyethenyl, formyl, C$_{2-6}$ alkylcarbonyl, C$_{1-6}$ alkylthio, C$_{1-6}$ alkylsulphonyl, amino, C$_{2-6}$ alkylcarbonylamino and di(C$_{1-6}$)alkylaminocarbonyl.

Typical substituents on the group Z include halogen, cyano, nitro, amino, formyl, C$_{2-6}$ alkoxycarbonyl and —CR$^a$=NOR$^b$.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-8}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylamino" and "C$_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular-cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$R$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Specifically, the present invention provides a compound of formula IA or IB, or a salt or prodrug thereof:

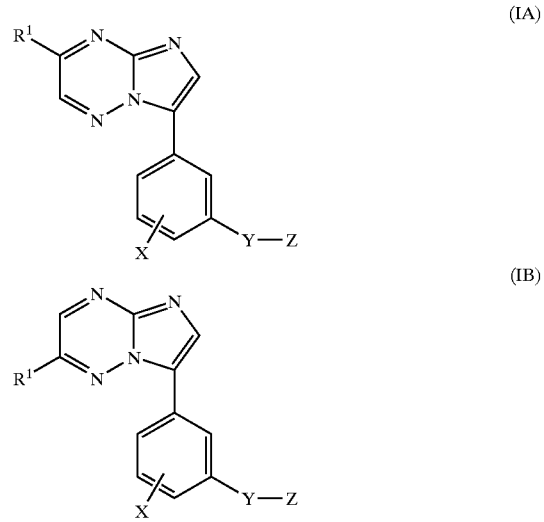

wherein X, Y, Z and R$^1$ are as defined above.

In one embodiment, the present invention provides a compound of formula IA as depicted above, or a salt or prodrug thereof.

In another embodiment, the present invention provides a compound of formula IB as depicted above, or a salt or prodrug thereof.

Suitably, X represents hydrogen or fluoro. Additionally, X may represent chloro.

In a preferred embodiment, X represents fluoro.

In another embodiment, X represents hydrogen.

In a preferred embodiment, Y represents a chemical bond.

In another embodiment, Y represents an oxygen atom.

In a further embodiment, Y represents a —NH— linkage.

Suitable values for the substituent Z include phenyl, pyridinyl, pyridazinyl, pyrimidinyl, pyrazinyl, furyl, thienyl, pyrrolyl, pyrazolyl, oxazolyl, isoxazolyl, thiazolyl, imidazolyl, oxadiazolyl, thiadiazolyl, triazolyl and tetrazolyl, any of which groups may be optionally substituted by one or more substituents.

Representative values for the substituent Z include phenyl, pyridinyl, thienyl and thiazolyl, any of which groups may be optionally substituted. In one favoured embodiment, Z represents an optionally substituted phenyl group, especially monosubstituted or disubstituted phenyl, and in particular monosubstituted phenyl. In another favoured embodiment, Z represents optionally substituted pyridinyl, particularly unsubstituted, monosubstituted or disubstituted pyridin-2-yl, pyridin-3-yl or pyridin-4-yl, and especially unsubstituted or monosubstituted pyridin-2-yl, pyridin-3-yl or pyridin-4-yl.

Suitably, Z represents disubstituted phenyl.

Suitably, Z represents disubstituted pyridin-2-yl.

Examples of individual substituents on the group Z include methyl, ethyl, fluoro, trifluoromethyl, hydroxy, hydroxymethyl, methoxy, nitro, cyano, carboxyethenyl, methoxycarbonyl, formyl, acetyl, methylthio, methylsulphonyl, amino, acetylamino, aminocarbonyl, dimethylaminocarbonyl and —CH=NOH.

Examples of specific substituents on the group Z include methyl, ethyl, fluoro, hydroxy, hydroxymethyl, methoxy, nitro, cyano, carboxyethenyl, formyl, acetyl, methylthio, methylsulphonyl, amino, acetylamino and dimethylaminocarbonyl.

Examples of suitable substituents on the group Z include fluoro, chloro, methoxy, trifluoromethyl, cyano, nitro, amino, formyl, methoxycarbonyl and —CH=NOH, especially fluoro and cyano.

Examples of typical substituents on the group Z include chloro, methoxy, trifluoromethyl, cyano, nitro, amino, formyl, methoxycarbonyl and —CH=NOH, especially cyano.

Itemised values of Z include fluorophenyl, trifluoromethylphenyl, hydroxyphenyl, hydroxymethyl-phenyl, methoxyphenyl, dimethoxyphenyl, nitrophenyl, cyanophenyl, (cyano)(fluoro)phenyl, (cyano)(difluoro) phenyl, carboxyethenyl-phenyl, formylphenyl, acetylphenyl, methylthio-phenyl, methylsulphonyl-phenyl, aminophenyl, acetylamino-phenyl, pyridinyl, methylpyridinyl, fluoropyridinyl, difluoropyridinyl, cyanopyridinyl, (amino)(chloro)pyridinyl, pyridazinyl, methoxypyridazinyl, pyrimidinyl, cyanopyrimidinyl, pyrazinyl, furyl, thienyl, cyano-thienyl, methoxycarbonyl-thienyl, formyl-thienyl, acetyl-thienyl, thienyl-CH=NOH, pyrrolyl, pyrazolyl, methyl-pyrazolyl, ethyl-pyrazolyl, oxazolyl, dimethyl-isoxazolyl, thiazolyl, nitro-thiazolyl, dimethylaminocarbonyl-thiazolyl, imidazolyl, methyl-oxadiazolyl, thiadiazolyl, methyl-thiadiazolyl, triazolyl, methyl-triazolyl and methyl-tetrazolyl.

Individual values of Z include fluorophenyl, hydroxyphenyl, hydroxymethyl-phenyl, methoxyphenyl, dimethoxyphenyl, nitrophenyl, cyanophenyl, (cyano)(fluoro)phenyl, (cyano)(difluoro)phenyl, carboxyethenyl-phenyl, formylphenyl, acetylphenyl, methylthio-phenyl, methylsulphonyl-phenyl, aminophenyl, acetylamino-phenyl, pyridinyl, methylpyridinyl, fluoropyridinyl, difluoropyridinyl, cyanopyridinyl, pyridazinyl, methoxypyridazinyl, pyrimidinyl, cyanopyrimidinyl, pyrazinyl, furyl, thienyl, formyl-thienyl, acetyl-thienyl, pyrrolyl, pyrazolyl, methyl-pyrazolyl, ethyl-pyrazolyl, oxazolyl, dimethyl-isoxazolyl, thiazolyl, nitro-thiazolyl, dimethylaminocarbonyl-thiazolyl, imidazolyl, methyl-oxadiazolyl, thiadiazolyl, methyl-thiadiazolyl, triazolyl, methyl-triazolyl and methyl-tetrazolyl.

Illustrative values of Z include trifluoromethylphenyl, cyanophenyl, nitrophenyl, methoxyphenyl, (cyano)(fluoro) phenyl, pyridinyl, cyanopyridinyl, (amino)(chloro) pyridinyl, cyano-thienyl, formyl-thienyl, methoxycarbonyl-thienyl, thienyl-CH=NOH and thiazolyl.

Specific values of Z include trifluoromethylphenyl, cyanophenyl, nitrophenyl, methoxyphenyl, pyridinyl, (amino)(chloro)pyridinyl, cyano-thienyl, formyl-thienyl, methoxycarbonyl-thienyl, thienyl-CH=NOH and thiazolyl.

Representative values of Z include cyanophenyl, (cyano)(fluoro)phenyl, pyridinyl and cyanopyridinyl. Exemplary Z groups include 2-cyanophenyl, 2-cyano-4-fluorophenyl, 2-cyano-5-fluorophenyl, 2-cyano-6-fluorophenyl, pyridin-2-yl, 3-cyanopyridin-2-yl, pyridin-3-yl and pyridin-4-yl.

A particular value of Z is cyanophenyl, especially 2-cyanophenyl.

In one embodiment, Z represents (cyano)(fluoro)phenyl, especially 2-cyano-6-fluorophenyl. In another embodiment, Z represents pyridinyl. In a further embodiment, Z represents difluoropyridinyl, especially 3,5-difluoropyridin-2-yl.

Suitably, $R^1$ represents hydrocarbon, a heterocyclic group, halogen, trifluoromethyl, —$OR^a$, —$COR^a$, —$CO_2R^a$ or —$CR^a$=$NOR^b$. Additionally, $R^1$ may represent hydrogen.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl.

Suitably, $R^b$ represents hydrogen, methyl, ethyl, hydroxyethyl or dimethylaminoethyl. Particular values of $R^b$ include hydrogen, hydroxyethyl and dimethylaminoethyl.

Illustrative values of $R^1$ include $C_{1-6}$ alkyl, halo($C_{1-6}$) alkyl, dihalo($C_{1-6}$)alkyl, hydroxy($C_{1-6}$)alkyl, heteroaryl, halogen, trifluoromethyl, $C_{1-6}$ alkoxy, formyl, $C_{2-6}$ alkylcarbonyl, $C_{2-6}$ alkoxycarbonyl and —$CR^a$=$NOR^b$, in which $R^a$ and $R^b$ are as defined above. Additionally, $R^1$ may represent hydrogen.

Typical values of $R^1$ include hydrogen, methyl, fluoromethyl, difluoromethyl, trifluoromethyl, hydroxymethyl, difluoroethyl, hydroxyethyl, fluoropropyl, hydroxypropyl, tert-butyl, furyl, chloro, methoxy, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl.

Specific values of $R^1$ include methyl, fluoromethyl, difluoromethyl, trifluoromethyl, hydroxymethyl, hydroxyethyl, furyl, chloro, methoxy, formyl, acetyl, methoxycarbonyl and —$CR^2$=$NOR^3$, in which $R^2$ and $R^3$ are as defined above.

Representative values of $R^1$ include hydrogen, methyl, difluoroethyl (especially 1,1-difluoroethyl), fluoropropyl (especially 2-fluoroprop-2-yl), hydroxypropyl (especially 2-hydroxyprop-2-yl), tert-butyl and trifluoromethyl.

Particular values of $R^1$ include methyl, fluoromethyl, difluoromethyl, trifluoromethyl and hydroxymethyl.

In one embodiment, $R^1$ represents methyl. In another embodiment, $R^1$ represents trifluoromethyl. In a further embodiment, $R^1$ represents 2-hydroxyprop-2-yl. In an additional embodiment, $R^1$ represents 2-fluoroprop-2-yl.

A particular sub-class of compounds according to the invention is represented by the compounds of formula IIA, and salts and prodrugs thereof:

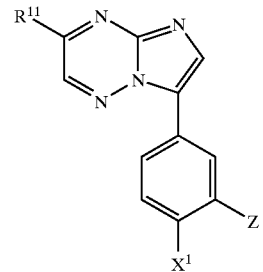

(IIA)

wherein $X^1$ represents hydrogen or fluoro;

Z is as defined above;

$R^{11}$ represents hydrogen, $C_{1-6}$ alkyl, halo($C_{1-6}$)alkyl, dihalo($C_{1-6}$)alkyl, hydroxy($C_{1-6}$)alkyl, heteroaryl, halogen, trifluoromethyl, $C_{1-6}$ alkoxy, formyl, $C_{2-8}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alkylamino($C_{1-6}$)alkyl.

The present invention also provides a compound of formula IIA as depicted above, or a salt or prodrug thereof, wherein $R^{11}$ represents $C_{1-6}$ alkyl, halo($C_{1-6}$)alkyl, dihalo($C_{1-6}$) alkyl, hydroxy($C_{1-6}$)alkyl, heteroaryl, halogen, trifluoromethyl, $C_{1-6}$ alkoxy, formyl, $C_{2-6}$ alkylcarbonyl, $C_{2-6}$ alkoxycarbonyl or —$CR^4$=$NOR^5$; and $X^1$, Z, $R^4$ and $R^5$ are as defined above.

In one embodiment, $X^1$ represents hydrogen. In another embodiment, $X^1$ represents fluoro.

Suitably, $R^4$ represents hydrogen or methyl.

Suitably, $R^5$ represents hydrogen, methyl, ethyl, hydroxyethyl or dimethylaminoethyl. Particular values of $R^5$ include hydrogen, hydroxyethyl and dimethylaminoethyl.

Where $R^{11}$ represents heteroaryl, this group is suitably furyl.

Illustrative values of $R^{11}$ include hydrogen, methyl, fluoromethyl, difluoromethyl, trifluoromethyl, hydroxymethyl, difluoroethyl, hydroxyethyl, fluoropropyl, hydroxypropyl, tert-butyl, furyl, chloro, methoxy, formyl, acetyl, methoxycarbonyl and —$CR^2$=$NOR^3$, in which $R^2$ and $R^3$ are as defined above.

Representative values of $R^{11}$ include methyl, fluoromethyl, difluoromethyl, trifluoromethyl, hydroxymethyl, hydroxyethyl, furyl, chloro, methoxy, formyl, acetyl, methoxycarbonyl and —$CR^2$=$NOR^3$, in which $R^2$ and $R^3$ are as defined above.

Specific values of $R^{11}$ include hydrogen, methyl, difluoroethyl (especially 1,1-difluoroethyl), fluoropropyl (especially 2-fluoroprop-2-yl), hydroxypropyl (especially 2-hydroxyprop-2-yl), tert-butyl and trifluoromethyl.

Particular values of $R^{11}$ include methyl, fluoromethyl, difluoromethyl, trifluoromethyl and hydroxymethyl.

In one embodiment, $R^{11}$ represents methyl. In another embodiment, $R^{11}$ represents trifluoromethyl. In a further embodiment, $R^{11}$ represents 2-hydroxyprop-2-yl. In an additional embodiment, $R^{11}$ represents 2-fluoroprop-2-yl.

The present invention advantageously provides a compound of formula IIA as depicted above, wherein $X^1$ and $R^{11}$ are as defined above; and Z represents (cyano)(fluoro)phenyl, cyanopyridinyl, fluoropyridinyl or difluoropyridinyl.

One representative subset of the compounds of formula IIA above is represented by the compounds of formula IIB, and salts and prodrugs thereof:

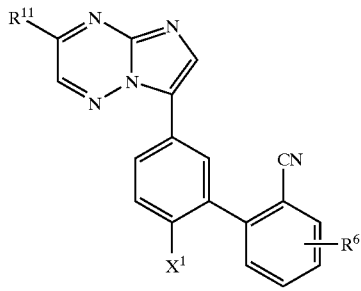

(IIB)

wherein $X^1$ and $R^{11}$ are as defined with reference to formula IIA above; and $R^6$ represents hydrogen or fluoro.

In one embodiment, $R^6$ is hydrogen.

In another embodiment, $R^6$ is fluoro, in which case the fluorine atom $R^6$ is favourably attached to the phenyl ring at the 4-, 5- or 6-position (relative to the cyano group at position 2), preferably at the 6-position.

Another representative subset of the compounds of formula IIA above is represented by the compounds of formula IIC, and salts and prodrugs thereof:

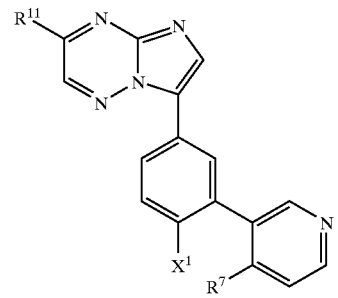

(IIC)

wherein $X^1$ and $R^{11}$ are as defined with reference to formula IIA above; and $R^7$ represents hydrogen, halogen or $C_{1-6}$ alkyl.

Typical values of $R^7$ include hydrogen, fluoro and methyl.

In one embodiment, $R^7$ represents hydrogen.

A further representative subset of the compounds of formula IIA above is represented by the compounds of formula IID, and salts and prodrugs thereof:

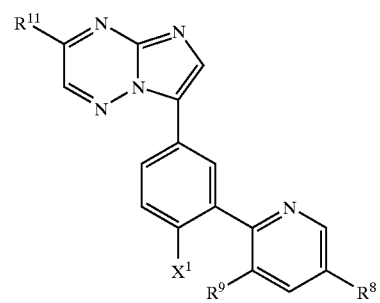

(IID)

wherein $X^1$ and $R^{11}$ are as defined with reference to formula IIA above;

$R^8$ represents hydrogen or fluoro; and $R^9$ represents hydrogen, fluoro or cyano.

In one embodiment, $R^8$ represents hydrogen and $R^9$ represents fluoro.

In another embodiment, $R^8$ represents fluoro and $R^9$ represents hydrogen.

In a preferred embodiment, $R^8$ and $R^9$ both represent fluoro.

In a further embodiment, $R^8$ and $R^9$ both represent hydrogen.

In an additional embodiment, $R^8$ represents hydrogen and $R^9$ represents cyano.

Another sub-class of compounds according to the invention is represented by the compounds of formula IIE, and salts and prodrugs thereof:

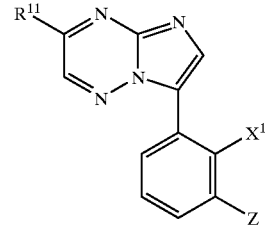

(IIE)

wherein Z, $X^1$ and $R^{11}$ are as defined above.

Specific compounds within the scope of the present invention include:

3'-(2-methylimidazo[1,2-b][1,2,4]triazin-7-yl)biphenyl-2-carbonitrile;
3'-(3-methylimidazo[1,2-b][1,2,4]triazin-7-yl)biphenyl-2-carbonitrile;
2'-fluoro-5'-(3-trifluoromethylimidazo[1,2-b][1,2,4]triazin-7-yl)biphenyl-2-carbonitrile;
3-(1-fluoro-1-methylethyl)-7-[4-fluoro-3-(pyridin-3-yl)phenyl]imidazo[1,2-b][1,2,4]triazine;
4,2'-difluoro-5'-[3-(1-fluoro-1-methylethyl)imidazo[1,2-b][1,2,4]triazin-7-yl]biphenyl-2-carbonitrile;
2'-fluoro-5'-(imidazo[1,2-b][1,2,4]triazin-7-yl)biphenyl-2-carbonitrile;
7-[4-fluoro-3-(pyridin-2-yl)phenyl]-3-trifluoromethylimidazo[1,2-b][1,2,4]triazine;
2'-fluoro-3'-(3-trifluoromethylimidazo[1,2-b][1,2,4]triazin-7-yl)biphenyl-2-carbonitrile;
5,2'-difluoro-5'-(3-trifluoromethylimidazo[1,2-b][1,2,4]triazin-7-yl)-biphenyl-2-carbonitrile;
2-[2-fluoro-5-(3-trifluoromethylimidazo[1,2-b]triazin-7-yl)phenyl]-nicotinonitrile;
3-(1,1-difluoroethyl)-7-[4-fluoro-3-(pyridin-3-yl)phenyl]imidazo[1,2-b][1,2,4]triazine;
3-tert-butyl-7-[4-fluoro-3-(pyridin-3-yl)phenyl]imidazo[1,2-b][1,2,4]triazine;
3-tert-butyl-7-[4-fluoro-3-(pyridin-2-yl)phenyl]imidazo[1,2-b][1,2,4]triazine;
4,2'-difluoro-5'-[3-(1-hydroxy-1-methylethyl)imidazo[1,2-b][1,2,4]triazin-7-yl]biphenyl-2-carbonitrile;
2-{7-[4-fluoro-3-(pyridin-3-yl)phenyl]imidazo[1,2-b][1,2,4]triazin-3-yl}propan-2-ol;
2-{7-[4-fluoro-3-(pyridin-4-yl)phenyl]imidazo[1,2-b][1,2,4]triazin-3-yl}propan-2-ol;
2'-fluoro-5'-[3-(1-hydroxy-1-methylethyl)imidazo[1,2-b][1,2,4]triazin-7-yl]biphenyl-2-carbonitrile;
4-fluoro-3'-[3-(1-hydroxy-1-methylethyl)imidazo[1,2-b][1,2,4]triazin-7-yl]-biphenyl-2-carbonitrile;
6,2'-difluoro-5'-[3-(1-hydroxy-1-methylethyl)imidazo[1,2-b][1,2,4]triazin-7-yl]biphenyl-2-carbonitrile;
2-{7-[2-fluoro-3-(pyridin-4-yl)phenyl]imidazo[1,2-b][1,2,4]triazin-3-yl}propan-2-ol;
2-{2-fluoro-5-[3-(1-hydroxy-1-methylethyl)imidazo[1,2-b][1,2,4]triazin-7-yl]phenyl}nicotinonitrile;
7-[6-fluoro-2'-(methanesulfonyl)biphenyl-3-yl]-3-trifluoromethylimidazo[1,2-b][1,2,4]triazine;
3'-[3-(1-hydroxy-1-methylethyl)imidazo[1,2-b][1,2,4]triazin-7-yl]biphenyl-2-carbonitrile;
2-{7-[3-(3,5-difluoropyridin-2-yl)-4-fluorophenyl]imidazo[1,2-b][1,2,4]triazin-3-yl}propan-2-ol;
4-{2-fluoro-5-[3-(1-hydroxy-1-methylethyl)imidazo[1,2-b][1,2,4]triazin-7-yl]phenyl}nicotinonitrile;
6,2'-difluoro-5'-[3-(1-fluoro-1-methylethyl)imidazo[1,2-b][1,2,4]triazin-7-yl]biphenyl-2-carbonitrile;
7-[3-(3,5-difluoropyridin-2-yl)-4-fluorophenyl]-3-(1-fluoro-1-methylethyl)-imidazo[1,2-b][1,2,4]triazine;
4,6,2'-trifluoro-5'-[3-(1-fluoro-1-methylethyl)imidazo[1,2-b][1,2,4]triazin-7-yl]biphenyl-2-carbonitrile;
2-{7-[4-fluoro-3-(3-fluoropyridin-2-yl)phenyl]imidazo[1,2-b][1,2,4]triazin-3-yl}propan-2-ol;
2-{7-[4-fluoro-3-(5-fluoropyridin-2-yl)phenyl]imidazo[1,2-b][1,2,4]triazin-3-yl}propan-2-ol;
2-[7-(4-fluoro-3-(pyridin-2-yl)phenyl)imidazo[1,2-b][1,2,4]triazin-3-yl]-propan-2-ol;
2-[7-(4-fluoro-3-(pyridazin-3-yl)phenyl)imidazo[1,2-b][1,2,4]triazin-3-yl]-propan-2-ol;
2-[7-(4-fluoro-3-(pyrimidin-4-yl)phenyl)imidazo[1,2-b][1,2,4]triazin-3-yl]-propan-2-ol;
2-[7-(4-fluoro-3-(pyridazin-4-yl)phenyl)imidazo[1,2-b][1,2,4]triazin-3-yl]-propan-2-ol;
4-{2-fluoro-5-[3-(1-hydroxy-1-methylethyl)imidazo[1,2-b][1,2,4]triazin-7-yl]phenyl}pyrimidine-5-carbonitrile;
2-{7-[3-(3,5-difluoropyridin-2-yl)phenyl]imidazo[1,2-b][1,2,4]triazin-3-yl}-propan-2-ol;
7-[3-(1-methyl-1H-pyrazol-3-yl)phenyl]-3-trifluoromethylimidazo[1,2-b][1,2,4]triazine;
7-[4-chloro-3-(pyridin-3-yl)phenyl]-3-trifluoromethylimidazo[1,2-b][1,2,4]-triazine;
7-[3-(pyridin-3-yl)phenyl]-3-trifluoromethylimidazo[1,2-b][1,2,4]triazine;
7-[3-([1,2,4]triazol-1-yl)phenyl]-3-trifluoromethylimidazo[1,2-b][1,2,4]triazine;
7-[3-(2-methyl-2H-[1,2,3]triazol-4-yl)phenyl]-3-trifluoromethylimidazo[1,2-b][1,2,4]triazine;
7-[3-(1-methyl-1H-[1,2,4]triazol-3-yl)phenyl]-3-trifluoromethylimidazo[1,2-b][1,2,4]triazine;
7-[4-fluoro-3-(imidazol-1-yl)phenyl]-3-trifluoromethylimidazo[1,2-b][1,2,4]triazine;
7-[4-fluoro-3-(pyridin-3-yl)phenyl]-3-trifluoromethylimidazo[1,2-b][1,2,4]triazine;
7-[4-fluoro-3-(5-fluoropyridin-2-yl)phenyl]-3-trifluoromethylimidazo[1,2-b][1,2,4]triazine;
7-[3-(pyrrol-1-yl)phenyl]-3-trifluoromethylimidazo[1,2-b][1,2,4]triazine;
7-[3-(pyridin-4-yl)phenyl]-3-trifluoromethylimidazo[1,2-b][1,2,4]triazine;
7-[3-(thiazol-2-yl)phenyl]-3-trifluoromethylimidazo[1,2-b][1,2,4]triazine;
7-[3-(5-fluoropyridin-2-yl)phenyl]-3-trifluoromethylimidazo[1,2-b][1,2,4]triazine;
7-[4-fluoro-3-(pyrazol-1-yl)phenyl]-3-trifluoromethylimidazo[1,2b][1,2,4]triazine;
7-[4-fluoro-3-([1,2,4]triazol-1-yl)phenyl]-3-trifluoromethylimidazo[1,2-b][1,2,4]triazine;
7-[4-fluoro-3-(oxazol-2-yl)phenyl]-3-trifluoromethylimidazo[1,2-b][1,2,4]triazine;
7-[3-(fur-2-yl)phenyl]-3-trifluoromethylimidazo[1,2-b][1,2,4]triazine;
7-[3-(2-methyltetrazol-5-yl)phenyl]-3-trifluoromethylimidazo[1,2-b][1,2,4]triazine;
7-[4-fluoro-3-(4-fluoropyridin-3-yl)phenyl]-3-trifluoromethylimidazo[1,2-b][1,2,4]triazine;
7-[4-fluoro-3-(pyridin-4-yl)phenyl]-3-trifluoromethylimidazo[1,2-b][1,2,4]triazine;
7-[3-(3,5-difluoropyridin-2-yl)-4-fluorophenyl]-3-trifluoromethylimidazo[1,2-b][1,2,4]triazine;
7-[4-fluoro-3-(2-methyltetrazol-5-yl)phenyl]-3-trifluoromethylimidazo[1,2-b][1,2,4]triazine;
7-[4-fluoro-3-(thiazol-4-yl)phenyl]-3-trifluoromethylimidazo[1,2-b][1,2,4]triazine;
7-[4-fluoro-3-(5-nitrothiazol-2-yl)phenyl]-3-trifluoromethylimidazo[1,2-b][1,2,4]triazine;
7-[3-(5-dimethylaminocarbonylthiazol-2-yl)-4-fluorophenyl]-3-trifluoromethylimidazo[1,2-b][1,2,4]triazine;
7-[4-fluoro-3-(thiazol-2-yl)phenyl]-3-trifluoromethylimidazo[1,2-b][1,2,4]triazine;
7-[3-(thien-2-yl)phenyl]-3-trifluoromethylimidazo[1,2-b][1,2,4]triazine;
7-[3-(thien-3-yl)phenyl]-3-trifluoromethylimidazo[1,2-b][1,2,4]triazine;
7-[3-(fur-3-yl)phenyl]-3-trifluoromethylimidazo[1,2-b][1,2,4]triazine;
7-[3-(4-methylpyridin-2-yl)phenyl]-3-trifluoromethylimidazo[1,2-b][1,2,4]triazine;

7-[3-(pyridin-2-yl)phenyl]-3-trifluoromethylimidazo[1,2-b][1,2,4]triazine;
7-[3-(pyrazin-2-yl)phenyl]-3-trifluoromethylimidazo[1,2-b][1,2,4]triazine;
7-[3-(4-fluoropyridin-2-yl)phenyl]-3-trifluoromethylimidazo[1,2-b][1,2,4]triazine;
7-[3-(thiazol-4-yl)phenyl]-3-trifluoromethylimidazo[1,2-b][1,2,4]triazine;
7-[4-fluoro-3-(1-methylpyrazol-4-yl)phenyl]-3-trifluoromethylimidazo[1,2-b][1,2,4]triazine;
7-[3-(imidazol-1-yl)phenyl]-3-trifluoromethylimidazo[1,2-b][1,2,4]triazine;
7-[3-(3-methyl-[1,2,4]oxadiazol-5-yl)phenyl]-3-trifluoromethylimidazo[1,2-b][1,2,4]triazine;
7-[3-(1-ethylpyrazol-3-yl)phenyl]-3-trifluoromethylimidazo[1,2-b][1,2,4]triazine;
7-[3-(5-methyl-[1,2,4]oxadiazol-2-yl)phenyl]-3-trifluoromethylimidazo[1,2-b][1,2,4]triazine;
7-[3-([1,2,3]thiadiazol-4-yl)phenyl]-3-trifluoromethylimidazo[1,2-b][1,2,4]triazine;
7-[3-(5-methyl-[1,2,4]thiadiazol-2-yl)phenyl]-3-trifluoromethylimidazo[1,2-b][1,2,4]triazine;
7-[2-fluoro-3-(pyridin-4-yl)phenyl]-3-trifluoromethylimidazo[1,2-b][1,2,4]triazine;
7-(2'-methoxybiphenyl-3-yl)-3-trifluoromethylimidazo[1,2-b][1,2,4]triazine;
1-[3'-(3-trifluoromethylimidazo[1,2-b][1,2,4]triazin-7-yl)biphenyl-3-yl]ethanone;
3'-(3-trifluoromethylimidazo[1,2-b][1,2,4]triazin-7-yl)biphenyl-4-carbaldehyde;
7-(2-fluoro-3',4'-dimethoxybiphenyl-5-yl)-3-trifluoromethylimidazo[1,2-b][1,2,4]triazine;
1-[2'-fluoro-5'-(3-trifluoromethylimidazo[1,2-b][1,2,4]triazin-7-yl)biphenyl-3-yl]ethanone;
3-[2'-fluoro-5'-(3-trifluoromethylimidazo[1,2-b][1,2,4]triazin-7-yl)biphenyl-3-yl]acrylic acid;
2'-fluoro-5'-(3-trifluoromethylimidazo[1,2-b][1,2,4]triazin-7-yl)biphenyl-4-carbaldehyde;
2'-fluoro-5'-(3-trifluoromethylimidazo[1,2-b][1,2,4]triazin-7-yl)biphenyl-3-ylamine;
N-[3'-(3-trifluoromethylimidazo[1,2-b][1,2,4]triazin-7-yl)biphenyl-3-yl]acetamide;
3'-(3-trifluoromethylimidazo[1,2-b][1,2,4]triazin-7-yl)biphenyl-2-carbaldehyde;
[3'-(3-trifluoromethylimidazo[1,2-b][1,2,4]triazin-7-yl)biphenyl-4-yl]-methanol;
1-[3'-(3-trifluoromethylimidazo[1,2-b][1,2,4]triazin-7-yl)biphenyl-4-yl]-ethanone;
3-[3-(3-trifluoromethylimidazo[1,2-b][1,2,4]triazin-7-yl)phenyl]thiophene-2-carbaldehyde;
3'-(3-trifluoromethylimidazo[1,2-b][1,2,4]triazin-7-yl)biphenyl-4-carbonitrile;
7-[3-(3,5-dimethylisoxazol-4-yl)-4-fluorophenyl]-3-trifluoromethylimidazo[1,2-b][1,2,4]triazine;
7-[3-(3-methoxypyridazin-5-yl)phenyl]-3-trifluoromethylimidazo[1,2-b][1,2,4]triazine;
7-(2-fluoro-4'-methoxybiphenyl-5-yl)-3-trifluoromethylimidazo[1,2-b][1,2,4]triazine;
7-[4-fluoro-3-(fur-2-yl)phenyl]-3-trifluoromethylimidazo[1,2-b][1,2,4]triazine;
7-(2-fluoro-4'-methylthiobiphenyl-5-yl)-3-trifluoromethylimidazo[1,2-b][1,2,4]triazine;
7-(2-fluoro-2'-methoxybiphenyl-5-yl)-3-trifluoromethylimidazo[1,2-b][1,2,4]triazine;
1-{5-[2-fluoro-5-(3-trifluoromethylimidazo[1,2-b][1,2,4]triazin-7-yl)-phenyl]thien-2-yl}ethanone;
7-(2,4'-difluorobiphenyl-5-yl)-3-trifluoromethylimidazo[1,2-b][1,2,4]triazine;
2'-fluoro-5'-(3-trifluoromethylimidazo[1,2-b][1,2,4]triazin-7-yl)biphenyl-4-ol;
7-(3'-nitrobiphenyl-3-yl)-3-trifluoromethylimidazo[1,2-b][1,2,4]triazine;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

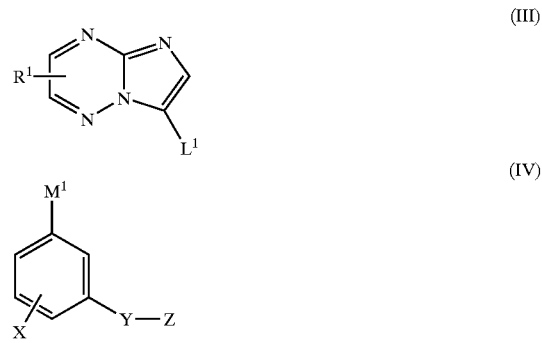

wherein X, Y, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds III and IV is suitably tetrakis (triphenylphosphine)-palladium(0). The reaction is conveniently carried out at an elevated temperature in a solvent such as N,N-dimethylacetamide, 1,2-dimethoxyethane, tetrahydrofuran or 1,4-dioxane, advantageously in the presence of potassium phosphate, sodium carbonate or copper(I) iodide. Alternatively, the transition metal catalyst employed may be dichloro[1,1'-bis(diphenylphosphino)ferrocene] palladium(II), in which case the reaction may conveniently be carried out at an elevated temperature in a solvent such as N,N-dimethylformamide, typically in the presence of potassium phosphate.

In an alternative procedure, the compounds according to the present invention in which Y represents a chemical bond may be prepared by a process which comprises reacting a compound of formula V with a compound of formula VI:

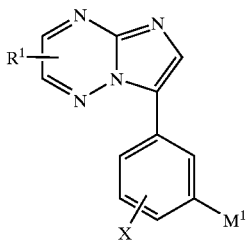

(V)

wherein X, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents an oxygen atom may be prepared by a process which comprises reacting a compound of formula VI as defined above with a compound of formula VII:

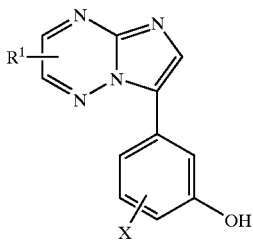

(VII)

wherein X and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula VI as defined above with a compound of formula VIII:

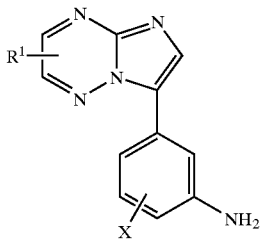

(VIII)

wherein X and $R^1$ are as defined above.

In relation to the reaction between compounds VI and VIII, the leaving group $L^1$ in the compounds of formula VI may suitably represent fluoro.

The reaction between compounds VI and VIII is conveniently carried out by heating the reactants, typically at a temperature in the region of 120° C., in a solvent such as N,N-dimethylformamide.

Where $M^1$ in the intermediates of formula IV and V above represents a boronic acid moiety —$B(OH)_2$ or a cyclic ester thereof formed with pinacol or neopentyl glycol, the relevant compound IV or V may be prepared by reacting bis(pinacolato)diboron or bis(neopentyl glycolato)diborane respectively with a compound of formula IVA or VA:

(IVA)

(VA)

wherein X, Y, Z and $R^1$ are as defined above, and $L^2$ represents hydroxy or a suitable leaving group; in the presence of a transition metal catalyst.

Where $L^2$ represents a leaving group, this is typically trifluoromethanesulfonyloxy (triflyloxy); or a halogen atom such as bromo.

The transition metal catalyst of use in the reaction between bis(pinacolato)diboron or bis(neopentyl glycolato) diborane and compound IVA or VA is suitably dichloro[1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where $L^2$ in the intermediates of formula VA above represents triflyloxy, the relevant compound VA may be prepared by reacting the appropriate compound of formula VII as defined above with N-phenyl-triflylimide, typically in the presence of triethylamine; or with triflic anhydride, typically in the presence of pyridine. Analogous conditions may be utilised for converting an intermediate of formula IVA above wherein $L^2$ represents hydroxy into the corresponding compound wherein $L^2$ represents triflyloxy.

The intermediates of formula VII above may suitably be prepared from the appropriate methoxy-substituted precursor of formula IX:

(IX)

wherein X and $R^1$ are as defined above; by treatment with boron tribromide, typically in chloroform; or with hydrogen bromide, typically in acetic acid at reflux.

The intermediates of formula VIII and IX above may be prepared by reacting a compound of formula III as defined above with the appropriate compound of formula X:

(X)

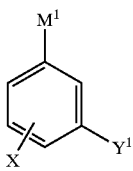

wherein X and M¹ are as defined above, and Y¹ represents amino or methoxy; in the presence of a transition metal catalyst; under conditions analogous to those described above for the reaction between compounds III and IV.

Where L¹ in the intermediates of formula III above represents bromo, this compound may be prepared by bromination of the corresponding compound of formula XI:

(XI)

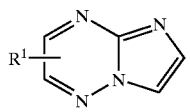

wherein R¹ is as defined above; typically by treatment with bromine in acetic acid, in the presence of sodium acetate and optionally also potassium bromide.

The intermediates of formula XI may be prepared by reacting bromoacetaldehyde with the requisite compound of formula XII:

(XII)

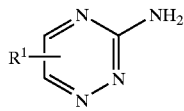

wherein R¹ is as defined above.

The reaction is conveniently carried out by heating the reactants in 1,2-dimethoxyethane, or a lower alkanol such as methanol and/or ethanol, at a temperature typically in the region of 60–80° C.

In a still further procedure, the compounds according to the present invention may be prepared by a process which comprises reacting a compound of formula XII as defined above with a compound of formula XIII:

(XIII)

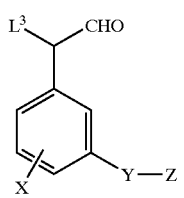

wherein X, Y and Z are as defined above, and L³ represents a suitable leaving group; under conditions analogous to those described above for the reaction between bromoacetaldehyde and compound XII.

The leaving group L³ is suitably a halogen atom, e.g. bromo.

In a yet further procedure, the compounds according to the present invention wherein X represents hydrogen and R¹ represents an aryl or heteroaryl moiety may be prepared by a process which comprises reacting a compound of formula XIV with a compound of formula XV:

(XIV)

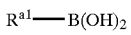

(XV)

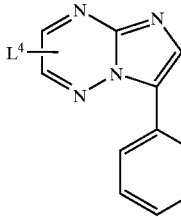

wherein Y and Z are as defined above, $R^{1a}$ represents an aryl or heteroaryl moiety, and L⁴ represents a suitable leaving group; in the presence of a transition metal catalyst.

The leaving group L⁴ is typically a halogen atom, e.g. chloro.

The transition metal catalyst of use in the reaction between compounds XIV and XV is suitably tris(dibenzylideneacetone)-dipalladium(0), in which case the reaction is conveniently effected at an elevated temperature in a solvent such as 1,4-dioxane, typically in the presence of tri-tert-butylphosphine and cesium carbonate.

Where L⁴ in the compounds of formula XV above represents a halogen atom, these compounds correspond to compounds of formula I as defined above wherein R¹ represents halogen, and they may therefore be prepared by any of the methods described above for the preparation of the compounds according to the invention.

In an additional procedure, the compounds according to the present invention in which Y represents a chemical bond may be prepared by reacting a compound of formula VA as defined above, wherein L² represents a suitable leaving group, with a compound of formula M¹-Z, wherein Z and M¹ are as defined above; in the presence of a transition metal catalyst; under conditions analogous to those described above for the reaction between compounds III and IV.

The compounds according to the present invention in which Y represents a chemical bond and Z represents pyrrol-1-yl may be prepared by reacting a compound of formula VIII as defined above with 2,5-dimethoxytetrahydrofuran. The reaction is conveniently accomplished at an elevated temperature in a solvent such as acetic acid.

Where they are not commercially available, the starting materials of formula VI, X, XII, XIII and XIV may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein R¹ represents $C_{2-6}$ alkoxycarbonyl initially obtained may be reduced with lithium aluminium hydride to the corresponding compound of formula I wherein R¹ represents hydroxymethyl. The latter compound may then be oxidised to the corresponding compound of formula I wherein R¹ represents formyl by treatment with manganese dioxide. The formyl derivative thereby obtained may be condensed with a hydroxylamine derivative of formula $H_2N$—$OR^b$ to provide a compound of formula I wherein R¹ represents —CH=NOR$^b$. Alternatively, the compound of formula I wherein R¹ represents formyl may be reacted with a Grignard reagent of formula $R^aMgBr$ to afford a compound of formula I wherein $R^1$ represents —CH(OH)$R^a$, and this compound may in turn be oxidised using manganese dioxide to the corresponding compound of formula I wherein $R^1$ represents —CO$R^a$. The latter compound may then be condensed with a hydroxylamine derivative of formula $H_2N$—O$R^b$ to provide a compound of formula I wherein $R^1$ represents —C$R^a$=NO$R^b$. A compound of formula I wherein the moiety Z is substituted by aminocarbonyl (—CONH$_2$) may be converted into the corresponding compound of formula I wherein Z is substituted by cyano by treatment with dibutyltin oxide, typically in refluxing toluene.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk$^−$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human GABA$_A$ receptor of 100 nM or less.

EXAMPLE 1

3'-(2-Methylimidazo[1,2-b][1,2,4]triazin-7-yl) biphenyl-2-carbonitrile and 3'-(3-methylimidazo[1,2-b][1,2,4]triazin-7-yl)biphenyl-2-carbonitrile a) 2- and 3-Methylimidazo[1,2-b][1,2,4]triazine A stirred mixture of bromoacetaldehyde diethyl acetal (5.10 ml, 32.9 mmol) in concentrated hydrobromic acid (1.62 ml) and water (1.62 ml) was heated at reflux for 2 h, then poured into ethanol (54 ml). The solution was neutralised to pH 7 with solid sodium hydrogencarbonate, then filtered. To the filtrate was added a 1:1 mixture of 3-amino-5-methyl-1,2,4-triazine and 3-amino-6-methyl-1,2,4-triazine (1.5210 g, 13.8 mmol) (prepared from pyruvic aldehyde and aminoguanidine bicarbonate as described by J. Daunis et al., *Bull. Soc. Chim. Fr.,* 1969, 10, 3675) and the mixture was stirred at 60° C. for 18 h. After allowing to cool, silica gel was added to the mixture, the solvent was removed in vacuao and the residue was introduced onto a flash column (silica gel, 2% MeOH/CH$_2$Cl$_2$) to give 0.2887 g (16%) of the title compounds as a 71:29 mixture: $^1$H NMR (360 MHz, CDCl$_3$) δ 2.64 and 2.69 (3H, two s), 7.86 (1H, two m), 7.89 and 7.92 (1H, two d, J 1.1 Hz), 8.24 and 8.33 (1H, two s); MS (ES$^+$) m/z 135 [M+H]$^+$.

b) 7-Bromo-2-methylimidazo[1,2-b][1,2,4]triazine and 7-bromo-3-methylimidazo[1,2-b][1,2,4]triazine To a solution of the 71:29 mixture of 2- and 3-methylimidazo[1,2-b][1,2,4]triazine (0.256 g, 1.91 mmol) in acetic acid (3 ml) was added sodium acetate (0.252 g, 3.07 mmol), then, dropwise over 3 min, bromine (109 μl, 2.12 mmol). The solution was stirred at room temperature for 15 min, then partitioned between saturated aqueous NaHCO$_3$ (135 ml) and ethyl acetate (150 ml). The aqueous layer (pH 8) was further extracted with ethyl acetate (150 ml), and the combined organic extracts were dried ($Na_2SO_4$) and evaporated in vacuo. The residue was purified by flash chromatography (silica gel, EtOAc) to afford 0.2623 g (66%) of the title compounds as a 74:26 mixture: $^1$H NMR (360 MHz, $CDCl_3$) δ 2.72 (3H, s), 7.86 (1H, two m), 7.89 and 7.93 (1H, two s), 8.35 and 8.36 (1H, two s); MS ($ES^+$) m/z 213/215 $[M+H]^+$.

c) 3'-(2-Methylimidazo[1,2-b][1,2,4]triazin-7-yl)biphenyl-2-carbonitrile and 3'-(3-methylimidazo[1,2-b][1,2,4]triazin-7-yl)biphenyl-2-carbonitrile A mixture of 2-bromobenzonitrile (9.1 g, 50 mmol), 3-aminobenzeneboronic acid monohydrate (11.6 g, 75 mmol) and tetrakis(triphenylphosphine)palladium(0) (1.73 g, 1.5 mmol) in ethylene glycol dimethyl ether (50 ml) and 2 M aqueous sodium carbonate (25 ml) was heated at 80° C. for 20 h. After cooling to ambient temperature the reaction was partitioned between ethyl acetate (400 ml) and water (400 ml). The organic layer was washed with brine (400 ml), dried ($Na_2SO_4$), and evaporated in vacuo. Purification of the residue by flash chromatography (silica gel, 0–25% EtOAc/isohexane) gave 9.5 g (98%) of 3'-aminobiphenyl-2-carbonitrile as a colourless oil that solidified on standing to afford a white solid: $^1$H NMR (400 MHz, $CDCl_3$) δ 3.79 (2H, br), 6.75 (1H, ddd, J 8, 3, 1 Hz), 6.84 (1H, dd, J 3, 3 Hz), 6.92 (1H, dd, J 8, 3 Hz), 7.25 (1H, dd, J 8, 8 Hz), 7.40 (1H, ddd, J 8, 8, 1 Hz), 7.50 (1H, dd, J 8, 1 Hz), 7.62 (1H, ddd, J 8, 8, 1 Hz), 7.73 (1H, dd, J 8, 1 Hz).

A solution of 3'-aminobiphenyl-2-carbonitrile (10.9 g, 56 mmol) in 1,4-dioxane (30 ml) was treated with a solution of 25% aqueous sulfuric acid (150 ml). The resulting suspension was cooled to 0° C. before being treated dropwise over 10 minutes with a solution of sodium nitrite (4.6 g, 67 mmol) in water (10 ml). After stirring at 0° C. for 30 minutes the reaction was poured into hot (70° C.) water (500 ml). On cooling to ambient temperature the product was extracted into ethyl acetate (500 ml), the organic layer was washed with water (300 ml), then brine (300 ml) and dried ($Na_2SO_4$). Filtration and evaporation in vacuo afforded 7.1 g (65%) of 3'-hydroxybiphenyl-2-carbonitrile as a dark oil: $^1$H NMR (400 MHz, $CDCl_3$) δ 5.40 (1H, br), 6.92 (1H, ddd, J 8, 3, 1 Hz), 7.04 (1H, dd, J 3, 3 Hz), 7.11 (1H, ddd, J 8, 3, 1 Hz), 7.35 (1H, dd, J 8, 8 Hz), 7.44 (1H, ddd, J 8, 8, 1 Hz), 7.51 (1H, dd, J 8, 1 Hz), 7.64 (1H, ddd, J 8, 8, 1 Hz), 7.75 (1H, dd, J 8, 1 Hz).

3'-Hydroxybiphenyl-2-carbonitrile (0.48 g, 2.47 mmol) and dry pyridine (0.98 g, 12.35 mmol) were dissolved in dichloromethane (7 ml) and cooled to 0° C. before the dropwise addition of trifluoromethanesulfonic anhydride (1.04 g, 3.70 mmol) over 5 min. The mixture was stirred at 0° C. for 10 min and then at 25° C. for 1 h. The solvent was evaporated in vacuo and the residue was partitioned between ethyl acetate (200 ml) and water (150 ml). The organic layer was washed with brine (150 ml), dried ($Na_2SO_4$) and evaporated in vacuo to give a brown oil. Purification by chromatography (silica gel, 0–30% EtOAc/isohexane) gave 544 mg (67%) of trifluoromethanesulfonic acid 2'-cyanobiphenyl-3-yl ester as a yellow oil: $^1$H NMR (400 MHz, $CDCl_3$) δ 7.37 (1H, ddd, J 8, 3, 1 Hz), 7.39 (1H, dd, J 3, 3 Hz), 7.50–7.60 (2H, m), 7.61–7.65 (2H, m), 7.64 (1H, td, J 8, 1 Hz), 7.80 (1H, dd, J 8, 1 Hz).

Trifluoromethanesulfonic acid 2'-cyanobiphenyl-3-yl ester (0.55 g, 1.66 mmol), potassium acetate (0.49 g, 4.98 mmol) and bis(pinacolato)diboron (0.55 g, 2.16 mmol) were dissolved in 1,4-dioxane (10 ml) and the mixture was degassed with nitrogen for 15 min. Dichloro[1,1'-bis(diphenylphosphino)ferrocene]palladium(II) dichloromethane adduct (41 mg, 0.05 mmol) and 1,1'-bis(diphenylphosphino)ferrocene (28 mg, 0.05 mmol) were then added and the mixture was heated at 85° C. for 18 h. The mixture was cooled to ambient temperature and partitioned between ethyl acetate (150 ml) and water (50 ml). The organic layer was washed with brine (50 ml), dried ($Na_2SO_4$), and evaporated in vacuo to give 0.51 g (100%) of 3'-(4,4,5,5-tetramethyl-[1,3,2]dioxaborolan-2-yl)biphenyl-2-carbonitrile as a black oil. This oil was dissolved in sufficient N,N-dimethylacetamide to give a 0.5 M stock solution.

A stirred 74:26 mixture of 7-bromo-2-methylimidazo[1,2-b][1,2,4]triazine and 7-bromo-3-methylimidazo[1,2-b][1,2,4]triazine (0.2623 g, 1.23 mmol), dried potassium phosphate (0.52 g, 2.46 mmol) and a 0.5 M solution of 3'-(4,4,5,5-tetramethyl-[1,3,2]dioxaborolan-2-yl)-biphenyl-2-carbonitrile in N,N-dimethylacetamide (4.92 ml, 2.46 mmol) was degassed by evacuation and refilling with nitrogen three times. Tetrakis(triphenylphosphine)palladium(0) (70 mg, 0.061 mmol) was then added and the mixture was degassed with two more evacuation-refilling cycles before heating at 80° C. under nitrogen for 24 h. The residue was purified by flash chromatography (silica gel, EtOAc) to give 0.1551 g (41%) of the title compounds as a mixture. These could be separated by preparative HPLC on an ABZ+ plus column (250×21 mm i.d.) eluting with 40% $MeCN/H_2O$ (+0.1% TFA) at 20 ml/min. Data for title compounds:

3'-(2-Methylimidazo[1,2-b][1,2,4]triazin-7-yl)biphenyl-2-carbonitrile: $^1$H NMR (400 MHz, $CDCl_3$) δ 2.72 (3H, s), 7.50 (1H, td, J 7.6, 1.3 Hz), 7.59–7.67 (3H, m), 7.70 (1H, td, J 7.7, 1.4 Hz), 7.82 (1H, dd, J 7.8, 1.0 Hz), 8.14 (1H, dt, J 7.6, 1.6 Hz), 8.29 (2H, m), 8.37 (1H, s); MS ($ES^+$) m/z 312 $[M+H]^+$.

3'-(3-Methylimidazo[1,2-b][1,2,4]triazin-7-yl)biphenyl-2-carbonitrile: mp 211–216° C. ($CH_2Cl_2$-EtOAc-isohexane); $^1$H NMR (400 MHz, $CDCl_3$) δ 2.73 (3H, s), 7.50 (1H, td, J 7.6, 1.3 Hz), 7.59–7.66 (3H, m), 7.70 (1H, td, J 7.7, 1.4 Hz), 7.82 (1H, dd, J 7.8, 1.4 Hz), 8.10 (1H, dt, J 7.6, 1.5 Hz), 8.29 (2H, t, J 1.4 Hz), 8.26 (1H, s), 8.36 (1H, s); MS ($ES^+$) m/z 312 $[M+H]^+$.

EXAMPLE 2

2'-Fluoro-5'-(3-trifluoromethylimidazo[1,2-b][1,2,4]triazin-7-yl)biphenyl-2-carbonitrile a) 3-Amino-5-trifluoromethyl-1,2,4-triazine To a stirred solution of sodium acetate trihydrate (22.62 g, 166.2 mmol) in water (80 ml) was added 1,1-dibromo-3,3,3-trifluoroacetone (21.57 g, 79.9 mmol). The solution was heated at reflux under nitrogen for 30 min, then allowed to cool to room temperature before adding solid aminoguanidine bicarbonate (10.88 g, 79.9 mmol). The resulting pale yellow solution (pH 5) was stirred at room temperature for 3 h, then 4 N aqueous NaOH solution (40 ml, 160 mmol) was added causing a precipitate to appear. The mixture (pH 10) was stirred under nitrogen for a further 39 h. The solid was collected by filtration, washed with water and dried at 60° C. under vacuum to give 6.96 g of a mixture of two isomers in a 28:72 ratio. This was further purified by flash chromatography (silica gel, 30% EtOAc/isohexane), then recrystallised from ethanol to afford 3.53 g (27%) of the title compound: $^1$H NMR (400 MHz, DMSO-$d_6$) δ 8.00 (2H, br s), 9.08 (1H, s).

b) 3-Trifluoromethylimidazo[1,2-b][1,2,4]triazine

A stirred mixture of bromoacetaldehyde diethyl acetal (2.30 ml, 14.8 mmol) in concentrated hydrobromic acid (0.73 ml) and water (0.73 ml) was heated at reflux for 2 h, then poured into ethanol (25 ml). The solution was neutralised to pH 7 with solid sodium hydrogencarbonate, then filtered. To the filtrate was added 3-amino-5-trifluoromethyl-1,2,4-triazine (1.0079 g, 6.14 mmol) and the mixture was stirred at 60° C. for 20 h, then 80° C. for 23 h. The mixture was evaporated in vacuo, and the residue was purified by flash chromatography (silica gel, 35–50% EtOAc/isohexane) to give 0.2593 g (22%) of the title compound: $^1$H NMR (360 MHz, CDCl$_3$) δ 8.20 (1H, d, J 0.8 Hz), 8.30 (1H, d, J 0.9 Hz), 8.73 (1H, s).

c) 7-Bromo-3-trifluoromethylimidazo[1,2-b][1,2,4]triazine

To a solution of 3-trifluoromethylimidazo[1,2-b][1,2,4]triazine (0.2211 g, 1.18 mmol) in acetic acid (6 ml) was added sodium acetate (0.1470 g, 1.79 mmol), then bromine (90.8 μl, 1.76 mmol). The solution was stirred at room temperature for 6 h, then partitioned between saturated aqueous NaHCO$_3$ (100 ml) and ethyl acetate (100 ml). The aqueous layer (pH 9) was further extracted with ethyl acetate (100 ml), and the combined organic extracts were dried (Na$_2$SO$_4$) and evaporated in vacuo. The residue was purified by flash chromatography (silica gel, 25% EtOAc/isohexane) to afford 0.2073 g (66%) of the title compound: $^1$H NMR (360 MHz, CDCl$_3$) δ 8.30 (1H, s), 8.83 (1H, s).

d) 2'-Fluoro-5'-(3-trifluoromethylimidazo[1,2-b][1,2,4]triazin-7-yl)biphenyl-2-carbonitrile A mixture of 2-bromo-1-fluoro-4-nitrobenzene (A. Groweiss, *Org. Process Res. Dev.*, 2000, 4, 30–33) (50.10 g, 0.228 mol), dried potassium acetate (44.70 g, 0.455 mol) and bis(pinacolato)diboron (59.16 g, 0.233 mol) in 1,4-dioxane (539 ml) and dimethylsulfoxide (11 ml) was degassed by bubbling nitrogen through the mixture for 1 h. Dichloro[1,1'-bis(diphenylphosphino)ferrocene]palladium(II) dichloromethane adduct (5.58 g, 6.83 mmol) was added and the mixture was stirred at 90° C. under nitrogen for 18.5 h, adding more bis(pinacolato)diboron (7.34 g, 0.029 mol) after 2.5 h. After allowing to cool, the mixture was filtered through glass fibre paper, and the solid was washed with a little dichloromethane. The combined filtrates were evaporated in vacuo and the residue was partitioned between 2 M aqueous NaOH (800 ml) and diethyl ether (800 ml). The aqueous layer was then acidified to pH 6 with concentrated hydrochloric acid (120 ml), causing a solid to precipitate. After leaving in a fridge for 3 days, the solid was collected by filtration, washed with water and dried under vacuum to leave 54.82 g (90%) of 2-(2-fluoro-5-nitrophenyl)-4,4,5,5-tetramethyl-[1,3,2]dioxaborolane: $^1$H NMR (360 MHz, DMSO-d$_6$) δ 1.33 (12H, s), 7.48 (1H, m), 8.40–8.45 (2H, m).

A mixture of 2-(2-fluoro-5-nitrophenyl)-4,4,5,5-tetramethyl-[1,3,2]dioxaborolane (37.62 g, 0.141 mol), 2-bromobenzonitrile (35.30 g, 0.194 mol) and tetrakis(triphenylphosphine)palladium(0) (5.85 g, 5.06 mmol) in ethylene glycol dimethyl ether (350 ml) and saturated aqueous NaHCO$_3$ (150 ml) was degassed by bubbling nitrogen through the mixture for 30 min. The mixture was then stirred at 90° C. under nitrogen for 15 h. After allowing to cool, the mixture was partitioned between dichloromethane (500 ml) and water (400 ml). The organic layer was washed with brine, dried (MgSO$_4$), then passed through a pad of Florisil®, washing the product through with more dichloromethane. The filtrates were evaporated in vacuo, and the residue was triturated with diethyl ether (100 ml) and isohexane (100 ml). The resulting solid was collected by filtration, washed with 50% Et$_2$O/isohexane and dried under vacuum to give 14.82 g (43%) of 2'-fluoro-5'-nitrobiphenyl-2-carbonitrile as a white solid. The combined filtrates were concentrated in vacuo to approximately 100 ml and the resulting solid was collected by filtration, washed with 20% Et$_2$O/isohexane and dried under vacuum to give another 0.94 g (3%) of the product. The filtrates were evaporated in vacuo, and the residue was purified by flash chromatography (silica gel, 10–15% EtOAc/isohexane) to afford another 3.07 g (9%) of the product: $^1$H NMR (360 MHz, CDCl$_3$) δ 7.40 (1H, t, J 8.5 Hz), 7.53 (1H, d, J 7.8 Hz), 7.59 (1H, td, J 7.7, 1.1 Hz), 7.74 (1H, td, J 7.7, 1.3 Hz), 7.84 (1H, dd, J 7.7, 0.9 Hz), 8.34–8.39 (2H, m).

To a stirred suspension of 2'-fluoro-5'-nitrobiphenyl-2-carbonitrile (18.71 g, 77.2 mmol) in THF (150 ml) and ethanol (150 ml) was added tin(II) chloride dihydrate (52.42 g, 232.4 mmol) and the mixture was stirred at room temperature for 22.5 h. The mixture was evaporated in vacuo and the residue was treated with ice-cold 2 N aqueous NaOH (800 ml). The resulting mixture was stirred for 1.5 h, then extracted with dichloromethane (2×800 ml). The combined organic extracts were washed with saturated aqueous NaCl (200 ml), dried (MgSO$_4$), and evaporated in vacuo. The residue was recrystallised from hot toluene (100 ml) to afford 11.33 g (69%) of 5'-amino-2'-fluorobiphenyl-2-carbonitrile as a white solid: $^1$H NMR (360 MHz, CDCl$_3$) δ 3.65 (2H, br s), 6.67–6.73 (2H, m), 7.00 (1H, t, J 9.0 Hz), 7.46 (1H, td, J 7.6, 1.1 Hz), 7.49 (1H, d, J 7.4 Hz), 7.64 (1H, td, J 7.7, 1.3 Hz), 7.76 (1H, dd, J 7.7, 0.7 Hz).

To a solution of 5'-amino-2'-fluorobiphenyl-2-carbonitrile (11.17 g, 52.6 mmol) in 1,4-dioxane (60 ml) was added 48% hydrobromic acid (250 ml) and the resulting suspension was cooled to 2° C., whilst stirring with an air stirrer. To this was added, dropwise over 20 min, a solution of sodium nitrite (4.18 g, 60.6 mmol) in water (11 ml), keeping the temperature below 5° C. The mixture was then stirred at 2±2° C. for 2 h before adding a cooled (5° C.) solution of freshly purified copper(I) bromide (25.40 g, 177.1 mmol) in 48% hydrobromic acid (75 ml). The mixture was stirred at 1±1° C. for 10 min before heating to 47° C. over 1 h. The mixture was diluted with ice-cold water (1.25 l) and extracted with ethyl acetate (2×500 ml). The combined organic extracts were washed with 1 M aqueous Na$_2$SO$_3$ (100 ml), then saturated aqueous NaCl (100 ml), dried (MgSO$_4$) and evaporated in vacuo to leave 16.08 g of 5'-bromo-2'-fluorobiphenyl-2-carbonitrile as a light brown solid: $^1$H NMR (360 MHz, CDCl$_3$) δ 7.12 (1H, t, J 9.1 Hz), 7.47–7.57 (4H, m), 7.68 (1H, td, J 7.7, 1.3 Hz), 7.79 (1H, d, J 7.8 Hz).

A mixture of the crude 5'-bromo-2'-fluorobiphenyl-2-carbonitrile (16.08 g), dried potassium acetate (10.33 g, 0.105 mol) and bis(pinacolato)diboron (15.37 g, 60.5 mmol) in 1,4-dioxane (123 ml) and dimethylsulfoxide (2.5 ml) was degassed by bubbling nitrogen through the mixture for 1 h. Dichloro[1,1'-bis(diphenylphosphino)ferrocene]-palladium (II) dichloromethane adduct (1.29 g, 1.58 mmol) was added and the mixture was stirred at 90° C. under nitrogen for 15.5 h. After allowing to cool, the mixture was filtered through glass fibre paper, and the solid was washed with a little dichloromethane. The combined filtrates were evaporated in vacuo and the residue was partitioned between 2 M aqueous NaOH (200 ml) and diethyl ether (200 ml). The aqueous layer was washed with more diethyl ether (100 ml), then acidified to pH 6 with concentrated hydrochloric acid (35 ml), causing a solid to precipitate. After leaving in a fridge for 3 days, the solid was collected by filtration, washed with water and dried under vacuum to leave 13.37 g (79% over two steps) of 2'-fluoro-5'-(4,4,5,5-tetramethyl-[1,3,2]dioxaborolan-2-yl)biphenyl-2-carbonitrile: $^1$H NMR (360 MHz, CDCl$_3$) δ 1.35 (12H, s), 7.21 (1H, t, J 9.3 Hz), 7.45–7.51 (2H, m), 7.65 (1H, t, J 7.7 Hz), 7.76 (1H, d, J 7.6 Hz), 7.83 (1H, d, J 7.8 Hz), 7.88 (1H, m).

A stirred mixture of 7-bromo-3-trifluoromethylimidazo[1,2-b][1,2,4]triazine (99.0 mg, 0.371 mmol), dried potassium phosphate (0.1581 g, 0.745 mmol) and 2'-fluoro-5'-(4,4,5,5-tetramethyl-[1,3,2]dioxaborolan-2-yl)biphenyl-2-carbonitrile (0.2402 g, 0.743 mmol) in anhydrous N,N-dimethylacetamide (2 ml) was degassed by evacuation and refilling with nitrogen three times. Tetrakis(triphenylphosphine)palladium(0) (22.1 mg, 0.0191 mmol) was then added and the mixture was degassed with two more evacuation-refilling cycles before heating at 80° C. under nitrogen for 6.5 h. The mixture was diluted with ethyl acetate and filtered through glass fibre paper, washing the solid with more ethyl acetate. The filtrates were washed with brine (15 ml), and the aqueous layer was extracted further with ethyl acetate (25 ml). The combined organic extracts were dried ($Na_2SO_4$) and evaporated in vacuo. The residue was purified by flash chromatography (silica gel, 30% EtOAc/isohexane) to give 76.6 mg (54%) of the title compound: mp 168–174° C. ($CH_2Cl_2$-EtOAc); $^1H$ NMR (400 MHz, $CDCl_3$) δ 7.43 (1H, t, J 9.0 Hz), 7.57 (1H, td, J 7.8, 1.2 Hz), 7.60 (1H, d, J 7.8 Hz), 7.73 (1H, td, J 7.8, 1.3 Hz), 7.85 (1H, dd, J 7.7, 1.1 Hz), 8.16–8.23 (2H, m), 8.62 (1H, s), 8.81 (1H, s); MS ($ES^+$) m/z 384 $[M+H]^+$. Anal. Found: C, 58.31; H, 2.28; N, 17.74%. Required for $C_{19}H_9F_4N_5.0.5H_2O$: C, 58.17; H, 2.57; N, 17.85%.

EXAMPLE 3

3-(1-Fluoro-1-methylethyl)-7-[4-fluoro-3-(pyridin-3-yl)phenyl]imidazo[1,2-b][1,2,4]triazine, Dihydrochloride Salt a) 3-Methyl-3-fluoro-2-butanone This was prepared from 3-bromo-3-methyl-2-butanone as described by Fry and Migron (*Tetrahedron Lett.*, 1979, 3357–3360) to give, after distillation using a Vigreux column, a 47% yield of a 94:6 mixture of the title compound and 3-methyl-3-buten-2-one as a colourless oil: bp 74–6° C.; $^1H$ NMR (360 MHz, $CDCl_3$) δ 1.45 (6H, d, J 21.5 Hz), 2.28 (3H, d, J 5.0 Hz).

b) 1,1-Dibromo-3-fluoro-3-methyl-2-butanone

To a stirred solution of 3-methyl-3-fluoro-2-butanone (0.1031 g, 0.990 mmol) in anhydrous dichloromethane (5 ml) under nitrogen was added solid pyridinium tribromide (0.7035 g, 1.98 mmol) and the mixture was stirred at room temperature for 18 h. The mixture was then diluted with dichloromethane (5 ml), washed with dilute aqueous sodium hydrogensulfite (10 ml), then saturated aqueous NaCl (10 ml), dried ($Na_2SO_4$) and evaporated under low vacuum with no heat. The residue was purified by flash chromatography [silica gel, 5% $Et_2O$/petroleum ether (40–60° C.)] to afford 0.1869 g (72%) of the title compound as a colourless oil: $^1H$ NMR (360 MHz, $CDCl_3$) δ 1.65 (6H, d, J 21.5 Hz), 6.51 (1H, d, J 1.5 Hz).

c) 3-Amino-5-(1-fluoro-1-methylethyl)-1,2,4-triazine

This was prepared in 45% yield as a single isomer by a similar procedure to that described in Example 2, step a, except using 1,1-dibromo-3-fluoro-3-methyl-2-butanone instead of 1,1-dibromo-3,3,3-trifluoroacetone: $^1H$ NMR (360 MHz, DMSO-$d_6$) δ 1.63 (6H, d, J 8.0 Hz), 7.32 (2H, br s), 8.73 (1H, d, J 1.0 Hz); MS ($ES^+$) m/z 157 $[M+H]^+$.

d) 3-(1-Fluoro-1-methylethyl)imidazo[1,2-b][1,2,4]triazine

A stirred mixture of bromoacetaldehyde diethyl acetal (1.20 ml, 7.73 mmol) in concentrated hydrobromic acid (0.38 ml) and water (0.38 ml) was heated at reflux for 40 min, then poured into ethanol (3 ml). The solution was neutralised to pH 7 with solid sodium hydrogencarbonate, then filtered, washing the solid with more ethanol (3 ml). To the filtrate was added 3-amino-5-(1-fluoro-1-methylethyl)-1,2,4-triazine (1.0046 g, 6.43 mmol) and the mixture was stirred at 70–80° C. for 17 h. The mixture was evaporated in vacuo, and the residue was purified by flash chromatography (silica gel, 70% EtOAc/isohexane to 15% MeOH/EtOAc, then 20% EtOAc/$CH_2Cl_2$) to give 0.2000 g (17%) of the title compound as a pale yellow solid: $^1H$ NMR (360 MHz, $CDCl_3$) δ 1.82 (6H, d, J 22.1 Hz), 7.97 (1H, d, J 1.3 Hz), 7.99 (1H, d, J 1.2 Hz), 8.69 (1H, d, J 1.0 Hz).

e) 7-Bromo-3-(1-fluoro-1-methylethyl)imidazo[1,2-b][1,2,4]triazine

This was prepared in 92% yield by a similar procedure to that described in Example 1, step b, except using 3-(1-fluoro-1-methylethyl)imidazo[1,2-b][1,2,4]triazine instead of 3-methylimidazo[1,2-b][1,2,4]triazine: $^1H$ NMR (360 MHz, $CDCl_3$) δ 1.82 (6H, d, J 22.1 Hz), 7.99 (1H, s), 8.81 (1H, d, J 1.1 Hz).

f) 3-(1-Fluoro-1-methylethyl)-7-[4-fluoro-3-(pyridin-3-yl)phenyl]imidazo[1,2-b][1,2,4]triazine, Dihydrochloride Salt To a solution of 2-bromo-1-fluoro-4-nitrobenzene (A. Groweiss, *Org. Process Res. Dev.*, 2000, 4, 30–33) in tetrahydrofuran (75 ml) and ethanol (75 ml) was added tin(II) chloride dihydrate and the mixture left to stir at ambient temperature for 4 h. The solvent was evaporated and the residue was treated with ice-cold 2 N sodium hydroxide solution (200 ml). The resulting slurry was stirred for 30 min then extracted with dichloromethane (3×200 ml). The combined organic phase was washed with water (200 ml) and brine (200 ml), dried ($MgSO_4$), filtered and evaporated to give 3-bromo-4-fluorophenylamine (7.92 g, 92%) as a yellow oil: $^1H$ NMR (360 MHz, $CDCl_3$) δ 3.53 (2H, s), 6.53–6.57 (1H, m), 6.83–6.85 (1H, m), 6.90 (1H, dd, J 9, 9 Hz).

A mixture of 3-bromo-4-fluorophenylamine (7.92 g, 41.7 mmol), diethyl(3-pyridyl)borane (6.74 g, 45.9 mmol), tetrakis(triphenylphosphine)palladium(0) (0.96 g, 0.83 mmol) and potassium carbonate (17.26 g, 125 mmol) in 1,2-dimethoxyethane (30 ml) and water (15 ml) was heated at 80° C. for 20 h. After cooling to ambient temperature the reaction was partitioned between ethyl acetate (500 ml) and water (500 ml). The organics were washed with brine (400 ml), dried ($Na_2SO_4$), filtered and concentrated in vacuo. Purification of the residue by flash chromatography (silica gel, 0%–20% EtOAc/$CH_2Cl_2$) gave 4-fluoro-3-(pyridin-3-yl)phenylamine (3.64 g, 46%) as a colourless oil that solidified on standing to afford a white solid: $^1H$ NMR (360 MHz, $CDCl_3$) δ 3.65 (2H, s), 6.65–6.72 (2H, m), 6.99 (1H, dd, J 9, 9 Hz), 7.33–7.37 (1H, m), 7.84–7.86 (1H, m), 8.58 (1H, d, J 4 Hz), 8.76 (1H, m).

A warm solution of 4-fluoro-3-(pyridin-3-yl)phenylamine (3.64 g, 19.3 mmol) in 1,4-dioxane (10 ml) was treated with a solution of 48% aqueous hydrobromic acid (100 ml). The resulting suspension was cooled to 0° C. before being treated dropwise over 20 min with a solution of sodium nitrite (1.53 g, 22.2 mmol) in water (4 ml). After stirring at 0° C. for 2 h, a cooled (0° C.) solution of copper(I) bromide (8.31 g, 57.9 mmol) in 48% aqueous hydrobromic acid (30 ml) was added to the reaction which was stirred at 0° C. for 10 min then heated at 50° C. for 20 min. The reaction was cooled to ambient temperature, poured onto ice-cold concentrated ammonia (500 ml) and the product was extracted into ethyl acetate (500 ml). The organics were washed with water (300 ml) and brine (300 ml), dried ($Na_2SO_4$), filtered and concentrated in vacuo to give a dark oil. Purification by dry flash column chromatography (silica gel, 10–30% EtOAc/isohexane) gave 3-(5-bromo-2-fluorophenyl)pyridine (3.1 g, 64%) as a white solid: $^1H$ NMR (360 MHz, $CDCl_3$) δ 7.09 (1H, dd, J 9, 1 Hz), 7.37–7.40 (1H, m), 7.46–7.51 (1H, m), 7.56–7.59 (1H, m), 7.83–7.86 (1H, m), 8.63–8.65 (1H, m), 8.77–8.79 (1H, m).

3-(5-Bromo-2-fluorophenyl)pyridine (3.1 g, 12.3 mmol), potassium acetate (3.62 g, 36.9 mmol) and bis(pinacolato) diboron (3.75 g, 14.8 mmol) were dissolved in 1,4-dioxane (40 ml) and dimethylsulfoxide (0.8 ml) and the mixture degassed with $N_2$ for 15 min. Dichloro[1,1'-bis (diphenylphosphino)ferrocene]palladium(II) dichloromethane adduct (300 mg, 0.37 mmol) was added and the mixture heated at 90° C. for 18 h. The mixture was cooled to ambient temperature and partitioned between diethyl ether (200 ml) and 2 N hydrochloric acid (50 ml). The organics were discarded and the aqueous phase adjusted to pH 8 by the addition of 4 N sodium hydroxide solution and extracted with diethyl ether (2×500 ml). The organic layer was washed with brine (50 ml), dried ($Na_2SO_4$), filtered and pre-adsorbed onto silica. Purification by flash column chromatography (silica gel, 25% EtOAc/isohexane) gave 3-[2-fluoro-5-(4,4,5,5-tetramethyl-[1,3,2]dioxaborolan-2-yl) phenyl]pyridine (2.64 g, 72%) as a yellow oil that crystallised on standing: $^1$H NMR (360 MHz, $CDCl_3$) δ 1.35 (12H, s), 7.20 (1H, dd, J 10, 8 Hz), 7.35–7.39 (1H, m), 7.81–7.91 (3H, m), 8.61 (1H, dd, J 5, 2 Hz), 8.82 (1H, s).

A stirred mixture of 7-bromo-3-(1-fluoro-1-methylethyl) imidazo[1,2-b][1,2,4]triazine (0.1059 g, 0.409 mmol) and 3-[2-fluoro-5-(4,4,5,5-tetramethyl-[1,3,2]dioxaborolan-2-yl)phenyl]pyridine (0.1832 g, 0.612 mmol) in 1,2-dimethoxyethane (2 ml) and 2 M aqueous $Na_2CO_3$ (0.613 ml, 1.23 mmol) was degassed by bubbling through nitrogen for 15 min. Tetrakis(triphenylphosphine)palladium(0) (23.4 mg, 0.020 mmol) was then added and the mixture was stirred at 80° C. for 16 h under nitrogen. The mixture was partitioned between ethyl acetate (25 ml) and water (10 ml) and the aqueous phase was extracted further with ethyl acetate (2×25 ml). The organic extracts were combined, dried ($Na_2SO_4$) and evaporated in vacuo. The residue was purified by flash chromatography (silica gel, EtOAc) to yield 0.1047 g (73%) of the title compound as a yellow oil. The hydrochloride salt was prepared in diethyl ether: mp 113–126° C.; $^1$H NMR (400 MHz, DMSO-$d_6$) δ 1.81 (6H, d, J 22.2 Hz), 7.68 (1H, dd, J 10.6, 8.6 Hz), 8.03 (1H, dd, J 7.8, 5.5 Hz), 8.36 (1H, m), 8.43 (1H, dd, J 7.4, 2.3 Hz), 8.63 (1H, dd, J 7.4, 1.2 Hz), 8.67 (1H, s), 8.91 (1H, d, J 4.3 Hz), 9.07 (1H, d, J 0.8 Hz), 9.16 (1H, s); MS ($ES^+$) m/z 352 $[M+H]^+$. Anal. Found: C, 51.65; H, 4.48; N, 15.28%. Required for $C_{19}H_{15}F_2N_5 \cdot 2HCl \cdot 0.07 C_4H_{10}O \cdot H_2O$: C, 51.75; H, 4.44; N, 15.65%.

EXAMPLE 4

4,2'-Difluoro-5'-[3-(1-fluoro-1-methylethyl)imidazo [1,2-b][1,2,4]triazin-7-yl]biphenyl-2-carbonitrile A mixture of 2-bromo-5-fluorobenzonitrile (20 g, 100 mmol), 2-(2-fluoro-5-nitrophenyl)-4,4,5,5-tetramethyl-[1,3,2]dioxaborolane (from Example 2, step d) (34.7 g, 130 mmol) and potassium fluoride (19.2 g, 330 mmol) in tetrahydrofuran (350 ml) and water (20 ml) was degassed with nitrogen for 30 min then treated with tris (dibenzylideneacetone)-dipalladium(0) (1.83 g, 2 mmol) followed by tri-tert-butylphosphine (4 ml of a 0.2 M solution in 1,4-dioxane, 0.8 mmol). This mixture was stirred at ambient temperature for 30 min before heating at 50° C. for 18 h. The resulting dark suspension was cooled to ambient temperature, diluted with 0.5 M sodium hydroxide (2.5 l) and stirred at ambient temperature for 4 h. The solid was collected by filtration, washed with water and dried under suction to afford 4,2'-difluoro-5'-nitrobiphenyl-2-carbonitrile as a black solid (28.1 g, >100%) contaminated with dibenzylideneacetone: $^1$H NMR (360 MHz, $CDCl_3$) δ 7.38–7.56 (4H, m), 8.33–8.40 (2H, m).

A suspension of 4,2'-difluoro-5'-nitrobiphenyl-2-carbonitrile (26 g, 100 mmol) in ethanol (180 ml) and ethyl acetate (180 ml) was treated with platinum(IV) oxide (1.02 g, 4.5 mmol) and then shaken under an atmosphere of hydrogen (40 psi) for 1 h. [The reaction was very exothermic and complete solution is brought about by the increase in temperature]. The catalyst was removed by filtration through glass microfibre filter paper [if any crystalline product is present the filter cake is washed with dichloromethane] and the filtrate evaporated to dryness to afford 5'-amino-4,2'-difluorobiphenyl-2-carbonitrile as a straw-coloured solid (23 g, 100%): $^1$H NMR (360 MHz, $CDCl_3$) δ 3.66 (2H, s), 6.66–6.70 (1H, m), 6.71–6.74 (1H, m), 7.00 (1H, dd, J 9, 9 Hz), 7.33–7.38 (1H, m), 7.44–7.49 (1H, m).

5'-Amino-4,2'-difluorobiphenyl-2-carbonitrile (23 g, 100 mmol) was dissolved in hot 1,4-dioxane (20 ml) then treated with a chilled (5° C.) solution of hydrobromic acid (200 ml of a 48% solution in water). The resulting suspension was cooled to 2° C. (internal temperature) before adding a solution of sodium nitrite (6.9 g, 100 mmol) in water (14 ml) at such a rate that the internal temperature did not exceed 4° C. Once addition was complete the reaction was stirred at <4° C. for 1 h before pouring the reaction into a cooled (5° C.) solution of copper(I) bromide (21.5 g, 150 mmol) in 48% aqueous hydrobromic acid (75 ml). The resulting dark mixture was left to stir at ambient temperature for 15 min then heated at 50° C. for 40 min. After cooling to ambient temperature the mixture was diluted with water (1 l) and then extracted with ethyl acetate (2×400 ml). The organics were combined then washed with 10% ammonium hydroxide (500 ml), water (500 ml), brine (400 ml) and dried ($MgSO_4$). Filtration and evaporation to dryness gave a brown oil, which crystallised on standing. Purification of this residue by dry flash chromatography (silica gel, 2–4% EtOAc/isohexane) furnished 5'-bromo-4,2'-difluorobiphenyl-2-carbonitrile as a white solid (27.5 g, 94%): $^1$H NMR (360 MHz, $CDCl_3$) δ 7.11 (1H, dd, J 9, 9 Hz), 7.37–7.58 (5H, m).

A mixture of 5'-bromo-4,2'-difluorobiphenyl-2-carbonitrile (1.26 g, 4.3 mmol), potassium acetate (1.26 g, 12.8 mmol) and bis(neopentyl glycolato)diboron (1.07 g, 4.7 mmol) in 1,4-dioxane containing 2% v/v dimethylsulfoxide (20 ml) was degassed with nitrogen for 10 min. Dichloro [1,1'-bis(diphenylphosphino)ferrocene]palladium(II) dichloromethane adduct (105 mg, 0.13 mmol) was then added and the mixture heated at 90° C. for 16 h. After cooling to ambient temperature the reaction mixture was filtered to remove inorganics and the filter cake was washed with diethyl ether. The filtrate was evaporated to dryness and the residue stirred with ice-cold 2 N sodium hydroxide solution (50 ml) for 45 min. This basic mixture was washed with diethyl ether and the organics discarded. The pH of the aqueous phase was adjusted to 5 with 36% hydrochloric acid then extracted with diethyl ether (50 ml). The organic phase was washed with brine, dried ($MgSO_4$), filtered and concentrated in vacuo to give 5'-(5,5-dimethyl-[1,3,2] dioxaborinan-2-yl)-4,2'-difluorobiphenyl-2-carbonitrile as a brown oil which crystallised on standing (1.15 g, 82%): $^1$H NMR (360 MHz, $CDCl_3$) δ 1.03 (6H, s), 3.76 (4H, s), 7.20 (1H, dd, J 10, 8 Hz), 7.33–7.38 (1H, m), 7.44–7.50 (2H, m), 7.81 (1H, dd, J 8, 2 Hz), 7.85–7.90 (1H, m).

5'-(5,5-Dimethyl-[1,3,2]dioxaborinan-2-yl)-4,2'-difluorobiphenyl-2-carbonitrile was coupled to 7-bromo-3-(1-fluoro-1-methylethyl)imidazo[1,2-b][1,2,4]triazine in 77% yield using a similar procedure to that described in Example 3, step f, to give a yellow solid: mp 156–159° C. (EtOAc-isohexane); $^1$H NMR (400 MHz, $CDCl_3$) δ 1.84

(6H, d, J 22.0 Hz), 7.36–7.46 (2H, m), 7.54 (1H, dd, J 7.8, 2.7 Hz), 7.57–7.60 (1H, m), 8.10–8.16 (2H, m), 8.30 (1H, s), 8.79 (1H, d, J 1.2 Hz); MS (ES$^+$) m/z 394 [M+H]$^+$. Anal. Found: C, 64.07; H, 3.66; N, 17.60%. Required for $C_{21}H_{14}F_3N_5$: C, 64.12; H, 3.59; N, 17.80%.

EXAMPLE 5

2'-Fluoro-5'-(imidazo[1,2-b][1,2,4]triazin-7-yl) biphenyl-2-carbonitrile a) Imidazo[1,2-b][1,2,4]triazine A stirred mixture of bromoacetaldehyde diethyl acetal (8.88 ml, 57.24 mmol) in concentrated hydrobromic acid (1.7 ml) and water (1.7 ml) was heated at reflux for 20 min, then poured into 1,2-dimethoxyethane (12.5 ml). The solution was neutralised to pH 7 with solid sodium hydrogencarbonate, then filtered. To the filtrate was added [1,2,4]triazin-3-ylamine (5.00 g, 52.03 mmol) and neutralised again with solid sodium hydrogencarbonate. The mixture was stirred at 80° C. for 20 h. After allowing to cool, silica gel was added to the mixture, the solvent was removed in vacuo and the residue was purified by chromatography (silica gel 5% MeOH/CH$_2$Cl$_2$) to give 0.292 g (5%) of the title compound: $^1$H NMR (360 MHz, DMSO-d$_6$) δ 8.01 (1H, d, J 1.4 Hz), 8.38 (1H, d, J 1.4 Hz), 8.59 (1H, d, J 2.1 Hz), 8.68 (1H, d, J 1.8 Hz); MS (ES$^+$) m/z 121 [M+H]$^+$.

b) 7-Bromoimidazo[1,2-b][1,2,4]triazine

To a solution of imidazo[1,2-b][1,2,4]triazine (0.206 g, 1.715 mmol), in acetic acid (5 ml) was added sodium acetate (0.211 g, 2.27 mmol), then, dropwise over 3 min, bromine (114.8 μl, 2.23 mmol). The solution was stirred at room temperature for 30 min, then partitioned between saturated aqueous NaHCO$_3$ (200 ml) and ethyl acetate (200 ml). The organic extracts were dried (Na$_2$SO$_4$), silica gel added and evaporated in vacuo. The residue was purified by chromatography (silica gel, 50% EtOAc/isohexane) to afford 0.3147 g (74%) of the title compound: $^1$H NMR (360 MHz, CDCl$_3$) δ 7.25 (1H, s), 8.05 (1H, s), 8.48–8.50 (1H, m); MS (ES$^+$) m/z 199.

c) 2'-Fluoro-5'-(imidazo[1,2-b][1,2,4]triazin-7-yl)biphenyl-2-carbonitrile

A stirred mixture of 7-bromoimidazo[1,2-b][1,2,4] triazine (0.22 g, 1.105 mmol), dried potassium phosphate (0.425 g, 2.002 mmol) and 2'-fluoro-5'-(4,4,5,5-tetramethyl-[1,3,2]dioxaborolan-2-yl)-biphenyl-2-carbonitrile (0.649 g, 2.008 mmol) in anhydrous N,N-dimethylacetamide (4 ml) was degassed by evacuation and refilling with nitrogen three times. Tetrakis(triphenylphosphine)palladium(0) (0.058 g, 0.05 mmol) was added and the mixture was degassed with two more evacuation-refilling cycles before heating at 80° C. for 4.5 h. The mixture was cooled to ambient temperature, diluted with ethyl acetate and filtered. The filtrate was washed with brine (200 ml), and the aqueous portion extracted with more ethyl acetate. The combined organic extracts were dried (Na$_2$SO$_4$) and evaporated in vacuo. The residue was purified by chromatography (silica gel, EtOAc) then recrystallisation (EtOAc) to give 74 mg (24%) of the title compound: mp 211–215° C.; $^1$H NMR (360 MHz, CDCl$_3$) δ 7.36–7.41 (1H, t, J 7.2 Hz), 7.53–7.61 (2H, m), 7.70–7.74 (1H, m), 7.83 (1H, d, J 7.7 Hz), 8.12–8.16 (2H, m), 8.35 (1H, s), 8.50 (1H, dd, J 2.1, 11.6 Hz); MS (ES$^+$) m/z 316 [M+H]$^+$.

EXAMPLE 6

7-[4-Fluoro-3-(pyridin-2-yl)phenyl]-3-trifluoromethylimidazo[1,2-b][1,2,4]triazine a) 2-(4-Fluoro-3-methoxyphenyl)-4,4,5,5-tetramethyl-[1,3,2]dioxaborolane A mixture of 4-bromo-1-fluoro-2-methoxybenzene (U.S. Pat. No. 4,593,037) (5.00 g, 24.39 mmol), dried potassium acetate (4.79 g, 48.77 mmol) and bis(pinacolato)diboron (7.12 g, 28.05 mmol) in 1,4-dioxane (53.9 ml) was degassed by evacuation and refilling with nitrogen three times. Dichloro[1,1'-bis(diphenylphosphino)ferrocene]palladium (II) dichloromethane adduct (0.59 g, 0.73 mmol) was added and the mixture was stirred at 90° C. under nitrogen for 17 h. After allowing to cool, the mixture was filtered through glass fibre paper, and the solid was washed with a little ethyl acetate. The combined filtrates were evaporated in vacuo and the residue was partitioned between 2 M aqueous NaOH (80 ml) and diethyl ether (80 ml). The aqueous layer was acidified to pH 7 with concentrated hydrochloric acid causing a solid to precipitate. After leaving in a fridge overnight, the solid was collected by filtration, washed with water and dried under a vacuum to leave 5.9 g (96%) of the title compound: $^1$H NMR (360 MHz, DMSO-d$_6$) δ 1.30 (12H, s), 3.85 (3H, s), 7.18–7.33 (3H, m).

b) 7-(4-Fluoro-3-methoxyphenyl)-3-trifluoromethylimidazo[1,2-b][1,2,4]triazine

A mixture of 2-(4-fluoro-3-methoxyphenyl)-4,4,5,5-tetramethyl-[1,3,2]dioxaborolane (0.637 g, 2.528 mmol), 7-bromo-3-trifluoromethylimidazo[1,2-b][1,2,4]triazine (0.5 g, 1.873 mmol) and saturated aqueous NaHCO$_3$ (10 ml) in 1,2-dimethoxyethane (25 ml) was degassed by evacuation and refilling with nitrogen three times. Tetrakis (triphenylphosphine)palladium(0) (0.169 g, 0.078 mmol) was added and the mixture was stirred under nitrogen at 95° C. for 17 h. After allowing to cool to ambient temperature, the mixture was diluted with ethyl acetate then filtered through glass fibre paper. The combined filtrates were partitioned between water (100 ml) and ethyl acetate (100 ml). The organic extracts were dried (MgSO$_4$) and evaporated in vacuo. The residue was purified by flash chromatography (silica gel, 25% EtOAc/isohexane), to give 275 mg (47%) of the title compound: $^1$H NMR (360 MHz, CDCl$_3$) δ 4.00 (3H, s), 7.26 (1H, dd, J 10.9, 8.4 Hz), 7.61–7.64 (1H, m), 7.76 (1H, dd, J 2.1, 8.1 Hz), 8.58 (1H, s), 8.81 (1H, s).

c) 2-Fluoro-5-(3-trifluoromethylimidazo[1,2-b][1,2,4] triazin-7-yl)phenol

To a stirred solution of 7-(4-fluoro-3-methoxyphenyl)-3-trifluoromethylimidazo[1,2-b][1,2,4]triazine (0.123 g, 0.397 mmol) in chloroform (5 ml) was added boron tribromide (1.19 ml, 1.91 mmol) and the mixture was stirred under nitrogen at room temperature for 21 h. 2 M NaOH (5 ml) was added and the mixture was stirred for 5 min producing a solid which was filtered and washed with water. The filtrate was washed with dichloromethane, and the aqueous layer was neutralised with concentrated hydrochloric acid causing a solid to precipitate. The solid was filtered, washed with water and dried under a vacuum to leave 109 mg (93%) of the title compound: $^1$H NMR (360 MHz, DMSO-d$_6$) δ 7.38 (1H, dd, J 8.8, 11.2 Hz), 7.60–7.64 (1H, m), 7.88 (1H, dd, J 1.9, 8.6 Hz), 9.32 (1H, s), 10.26 (1H, s); MS (ES$^+$) m/z 299 [M+H]$^+$.

d) Trifluoromethanesulfonic Acid 2-fluoro-5-(3-trifluoromethylimidazo[1,2-b][1,2,4]triazin-7-yl)phenyl Ester To a stirred solution of 2-fluoro-5-(3-trifluoromethylimidazo[1,2-b][1,2,4]triazin-7-yl)phenol (0.109 g, 0.366 mmol) in dichloromethane (4 ml) was added triethylamine (66.2 μl, 0.476 mmol) and N-phenyltrifluoromethanesulfonimide (0.157 g, 0.439 mmol) in dichloromethane (4 ml). The mixture was stirred at room temperature under nitrogen for 20 h, then partitioned between ammonium chloride (5 ml), sodium chloride (5 ml), water (5 ml) and dichloromethane (10 ml). The organic layer was dried ($Na_2SO_4$) and evaporated in vacuo. The residue was purified by flash chromatography (silica gel, 30% EtOAc/isohexane) to afford 0.158 g (100%) of the title compound: $^1$H NMR (360 MHz, $CDCl_3$) δ 7.48 (1H, t, J 8.9 Hz), 8.05–8.09 (1H, m), 8.27 (1H, dd, J 2.1, 7.0 Hz), 8.62 (1H, s), 8.86 (1H, s); MS ($ES^+$) m/z 431 $[M+H]^+$.

e) 7-[4-Fluoro-3-(pyridin-2-yl)phenyl]-3-trifluoromethylimidazo[1,2-b][1,2,4]triazine A solution of trifluoromethanesulfonic acid 2-fluoro-5-(3-trifluoromethylimidazo[1,2-b][1,2,4]triazin-7-yl)phenyl ester (0.439 g, 1.020 mmol) in 1,4-dioxane (4 ml) was degassed by evacuation and refilling with nitrogen three times before dichloro[1,1'-bis(diphenylphosphino)ferrocene]palladium(II) dichloromethane adduct (0.028 g, 0.051 mmol), 1,1'-bis(diphenylphosphino)ferrocene (0.028 g, 0.05 mmol), potassium acetate (0.300 g, 30.6 mmol) and bis(neopentyl glycolato)diboron (0.253 g, 1.12 mmol) were added. The mixture was degassed again before heating at 80° C. for 12 h. The mixture was evaporated in vacuo then partitioned between 2 M NaOH (15 ml) and diethyl ether (15 ml). The aqueous layer was acidified to pH 6 with concentrated hydrochloric acid producing a solid, which was filtered, washed with water and dried under vacuum to leave 33 mg of 7-[3-(5,5-dimethyl-[1,3,2]dioxaborinan-2-yl)-4-fluorophenyl]-3-trifluoromethylimidazo[1,2-b][1,2,4]triazine.

This was added to 1,2-dimethoxyethane (2 ml), 2-bromopyridine (9 μl, 0.092 mmol), $Na_2CO_3$ (0.018 g, 0.168 mmol) and water (0.5 ml). The mixture was degassed by evacuation and refilling with nitrogen three times before tetrakis(triphenylphosphine)palladium(0) (7.58 mg, 0.0065 mmol) was added and the mixture degassed twice more before heating at 95° C. for 21 h. The mixture was cooled to ambient temperature before filtering and partitioning between water (15 ml) and ethyl acetate (15 ml). The organic extracts were dried ($Na_2SO_4$) and evaporated in vacuo. The residue was purified by chromatography (silica gel, 25% EtOAc/isohexane) then recrystallisation (EtOAc) to give 6.0 mg (23%) of the title compound: mp 128–131° C.; $^1$H NMR (400 MHz, $CDCl_3$) δ 7.32–7.38 (1H, m), 7.39 (1H, d, J 10.6 Hz), 7.80–7.84 (1H, m), 7.88–7.90 (1H, m), 8.15–8.19 (1H, m), 8.67 (1H, s), 8.74–8.79 (2H, m), 8.82 (1H, s); MS ($ES^+$) m/z 359.

EXAMPLE 7

2'-Fluoro-3'-(3-trifluoromethylimidazo[1,2-b][1,2,4]triazin-7-yl)biphenyl-2-carbonitrile a) 2'-Fluorobiphenyl-2-carbonitrile A mixture of 2-bromobenzonitrile (5.1 g, 28 mmol), 2-fluorobenzeneboronic acid (4.9 g, 35 mmol) and potassium fluoride (5.37 g, 92 mmol) in THF (50 ml) was degassed with nitrogen for 10 min. This mixture was then treated with tris(dibenzylideneacetone)dipalladium(0) (510 mg, 0.56 mmol) followed by tri-tert-butylphosphine (5.6 ml of a 0.2 M solution in 1,4-dioxane, 1.12 mmol) and the reaction was stirred at ambient temperature for 15 min. The resulting slurry was then heated at 50° C. for 30 min in order to consume remaining starting materials and then cooled to ambient temperature. The reaction mixture was filtered, washing the filter-cake with tetrahydrofuran (50 ml). The filtrate was evaporated to dryness and the residue partitioned between ethyl acetate and water. The organics were washed with brine, dried over anhydrous magnesium sulfate, filtered and pre-adsorbed onto silica. Purification by chromatography (silica gel, 5–10% EtOAc/isohexane) gave 5.5 g (100%) of the title compound as a pale yellow solid: $^1$H NMR (360 MHz, $CDCl_3$) δ 7.19–7.29 (2H, m), 7.40–7.52 (4H, m), 7.65 (1H, ddd, J 8, 8, 1 Hz), 7.79 (1H, dd, J 8, 1 Hz).

b) 2'-Cyano-2-fluorobiphenyl-3-boronic Acid

A cooled (−78° C.) solution of n-butyllithium (11.7 ml of a 2.5 M solution in hexanes, 29.1 mmol) in THF (100 ml) was treated with 2,2,6,6-tetramethylpiperidine (5.16 ml) and stirring at −78° C. was continued for 15 min. The reaction was then treated with a cooled (0° C.) solution of 2'-fluorobiphenyl-2-carbonitrile (5.50 g) in THF (15 ml) added dropwise over 10 min. This mixture was stirred at −78° C. for 2 h and then treated with trimethyl borate (6.30 ml) added dropwise over 5 min. The reaction was stirred at −78° C. for 10 min then allowed to warm to ambient temperature. 2 N Hydrochloric acid (5 ml) was added and the mixture evaporated to dryness. The residue was stirred with 2 N hydrochloric acid (95 ml) for 30 min and then extracted with diethyl ether (2×100 ml). The organics were combined, extracted with 2 N sodium hydroxide (100 ml) and the organics discarded. The aqueous was cooled to 0° C. and made just acidic (pH 6) with 36% hydrochloric acid. After stirring at 0° C. for 1 h the resulting solid was collected by filtration and dried. Crystallisation from diethyl ether/isohexane afforded 4.50 g (67%) of the title compound as a yellow solid: $^1$H NMR (360 MHz, $CDCl_3$) δ 5.23 (1H, s), 5.25 (1H, s), 7.33 (1H, m), 7.42–7.56 (3H, m), 7.65 (1H, m), 7.77 (1H, m), 7.93 (1H, m).

c) 2'-Fluoro-3'-(3-trifluoromethylimidazo[1,2-b][1,2,4]triazin-7-yl)biphenyl-2-carbonitrile 7-Bromo-3-trifluoromethylimidazo[1,2-b][1,2,4]triazine was coupled with 2'-cyano-2-fluorobiphenyl-3-boronic acid as described in Example 3, step f, to give 21 mg (15%) of the title compound: mp 167–168° C.; $^1$H NMR (360 MHz, $CDCl_3$) δ 7.47–7.60 (4H, m), 7.73 (1H, dd, J 1.4, 7.7 Hz), 7.84 (1H, dd, J 0.7, 7.0 Hz), 8.26–8.30 (1H, m), 8.69 (1H, d, J 2.8 Hz), 8.83 (1H, s); MS ($ES^+$) m/z 384 $[M+H]^+$. Anal. Found: C, 59.14; H, 2.75; N, 18.01%. Required for $C_{19}H_9F_4N_5 \cdot 0.2H_2O$: C, 58.98; H, 2.45; N, 18.10%.

EXAMPLE 8

5,2'-Difluoro-5'-(3-trifluoromethylimidazo[1,2-b][1,2,4]triazin-7-yl)-biphenyl-2-carbonitrile a) 5,2'-Difluoro-5'-nitrobiphenyl-2-carbonitrile A suspension of 2-bromo-4-fluorobenzonitrile (2.50 g, 12.5 mmol), potassium fluoride (2.40 g, 41.3 mmol) and 2-(2-fluoro-5-nitrophenyl)-4,4,5,5-tetramethyl-[1,3,2]dioxaborolane (4.67 g, 17.5 mmol) in tetrahydrofuran (50 ml) was degassed with nitrogen for 30 min. Tris(dibenzylideneacetone)dipalladium(0) and tri-tert-butylphosphine (0.2 M solution in 1,4-dioxane, 3.7 ml) were added and the mixture stirred at ambient temperature for 15 min then at 50° C. for 18 h. After cooling to ambient temperature, the resulting dark suspension was poured onto 0.5 M sodium hydroxide solution (500 ml) and stirred vigorously for 2 h. The dark solid was collected by filtration, washed with water (100 ml) and isohexane (50 ml) and left to air dry which gave the title compound as a brown/black solid: $^1$H NMR (360 MHz, $CDCl_3$) δ 7.25–7.33 (2H, m), 7.40–7.44 (1H, m), 7.86 (1H, dd, J 9, 6 Hz), 8.35–8.42 (2H, m).

b) 5'-Amino-5,2'-difluorobiphenyl-2-carbonitrile 5,2'-Difluoro-5'-nitrobiphenyl-2-carbonitrile (3.25 g, 12.5 mmol) in tetrahydrofuran (20 ml) and ethanol (20 ml) was treated with tin(II) chloride dihydrate (9.86 g, 43.8 mmol) and the mixture left to stir at ambient temperature for 18 h. The solvent was evaporated and the residue stirred with 2 N sodium hydroxide solution (40 ml) for 2 h. The resulting suspension was diluted with water (100 ml) and extracted with dichloromethane (3×200 ml). The combined organics were washed with water (200 ml), brine (200 ml), dried over anhydrous sodium sulfate, filtered and evaporated to give the title compound as a brown solid: $^1$H NMR (360 MHz, CDCl$_3$) δ 3.68 (2H, s), 6.67–6.76 (2H, m), 7.02 (1H, dd, J 9, 9 Hz), 7.12–7.27 (2H, m), 7.78 (1H, dd, J 9, 6 Hz).

c) 5'-Bromo-5,2'-difluorobiphenyl-2-carbonitrile

5'-Amino-5,2'-difluorobiphenyl-2-carbonitrile (2.87 g, 12.5 mmol) was dissolved in hot 1,4-dioxane (4 ml), 48% aqueous hydrobromic acid (40 ml) was added and the mixture cooled to 0° C. before dropwise addition of sodium nitrite (0.86 g, 12.5 mmol) in water (1.5 ml) over 20 min. The resulting mixture was stirred at 0° C. for 1.5 h then poured onto a cooled (0° C.) solution of copper(I) bromide (5.38 g, 37.5 mmol) in 48% hydrobromic acid (10 ml). The solution was stirred at 0° C. for 15 min then heated at 50° C. for 20 min. The mixture was cooled to ambient temperature, diluted with water (500 ml) and extracted with ethyl acetate (2×300 ml). The combined organics were washed with 10% aqueous ammonia solution (200 ml), water (200 ml) and brine (200 ml), dried over anhydrous magnesium sulfate, filtered and evaporated to give a black solid. Purification by chromatography [silica gel, 2–6% EtOAc/isohexane (containing 0.5% methanol)] gave the title compound as a pale brown solid: $^1$H NMR (400 MHz, CDCl$_3$) δ 7.13 (1H, dd, J 9, 9 Hz), 7.19–7.23 (2H, m), 7.52–7.60 (2H, m), 7.81 (1H, dd, J 8, 5 Hz).

d) 5'-(5,5-Dimethyl-[1,3,2]dioxaborinan-2-yl)-5,2'-difluorobiphenyl-2-carbonitrile A mixture of 5'-bromo-5,2'-difluorobiphenyl-2-carbonitrile (2.48 g, 8.43 mmol), potassium acetate (2.48 g, 25.3 mmol) and bis(neopentyl glycolato)diboron (2.48 g, 11.0 mmol) in 1,4-dioxane (40 ml) containing dimethylsulfoxide (0.8 ml) was degassed with nitrogen for 20 min. Dichloro[1,1'-bis(diphenylphosphino)ferrocene]palladium (II) dichloromethane adduct (200 mg, 0.25 mmol) was then added and the reaction heated at 90° C. for 24 h. The mixture was cooled to ambient temperature then partitioned between 2 N sodium hydroxide (75 ml) and diethyl ether (100 ml) and the organics were discarded. The aqueous extract was made acidic (pH 5) with 36% hydrochloric acid and then extracted with diethyl ether (2×75 ml). The organic extract was washed with water (50 ml) and brine (75 ml), dried over anhydrous magnesium sulfate and evaporated to give 5'-(5,5-dimethyl-[1,3,2]dioxaborinan-2-yl)-5,2'-difluorobiphenyl-2-carbonitrile as a brown oil that crystallised on standing: $^1$H NMR (400 MHz, CDCl$_3$) δ 1.03 (6H, s), 3.77 (4H, s), 7.15–7.24 (3H, m), 7.77 (1H, dd, J 9, 6 Hz), 7.83 (1H, dd, J 8, 2 Hz), 7.87–7.91 (1H, m).

7-Bromo-3-trifluoromethylimidazo[1,2-b][1,2,4]triazine was coupled with 5'-(5,5-dimethyl-[1,3,2]dioxaborinan-2-yl)-5,2'-difluorobiphenyl-2-carbonitrile as described in Example 3 to give 68.7 mg (46%) of 5,2'-difluoro-5'-(3-trifluoromethylimidazo[1,2-b][1,2,4]triazin-7-yl)biphenyl-2-carbonitrile as a yellow solid: mp 200–201° C.; $^1$H NMR (360 MHz, CDCl$_3$) δ 7.25–7.34 (2H, m), 7.44 (1H, t, J 8.9 Hz), 7.87 (1H, dd, J 5.4, 8.6 Hz), 8.18–8.26 (2H, m), 8.63 (1H, s), 8.82 (1H, s); MS (ES$^+$) m/z 401. Anal. Found: C, 55.98; H, 2.13; N, 17.49%. Required for C$_{19}$H$_8$F$_5$N$_5$.0.3H$_2$O: C, 56.11; H, 2.13; N, 17.22%.

EXAMPLE 9

2-[2-Fluoro-5-(3-trifluoromethylimidazo[1,2-b]triazin-7-yl)phenyl]-nicotinonitrile a) 2-(2-Fluoro-5-nitrophenyl)nicotinonitrile A mixture of 2-chloronicotinonitrile (2.49 g, 18.02 mmol), 2-(2-fluoro-5-nitrophenyl)-4,4,5,5-tetramethyl-[1,3,2]dioxaborolane (from Example 2, step d) (6.14 g, 23.43 mmol) and potassium fluoride (3.46 g, 59.47 mmol) in tetrahydrofuran (120 ml), was degassed with nitrogen for 30 min then treated with tris(dibenzylideneacetone)dipalladium (0) (0.33 g, 0.360 mmol), followed by tri-tert-butylphosphine (3.6 ml of a 0.2 M solution in 1,4-dioxane, 0.721 mmol). The mixture was degassed again before heating at 50° C. for 18 h. The mixture was cooled to ambient temperature then partitioned between ethyl acetate and water. The organic extracts were dried (Na$_2$SO$_4$), filtered and evaporated in vacuo. The residue was purified by flash chromatography (silica gel, CH$_2$Cl$_2$) to afford 3.759 g (86%) of the title compound: $^1$H NMR (360 MHz, CDCl$_3$) δ 8.97 (1H, dd, J 5, 2 Hz), 8.56 (1H, dd, J 6, 3 Hz), 8.40–8.45 (1H, m), 8.15 (1H, dd, J 8, 2 Hz), 7.55 (1H, dd, J 8, 5 Hz), 7.43 (1H, dd, J 9, 9 Hz); MS (ES$^+$) m/z 244 [M+H]$^+$.

b) 2-(5-Amino-2-fluorophenyl)nicotinonitrile 2-(2-Fluoro-5-nitrophenyl)nicotinonitrile (4.5 g, 18.62 mmol) was reduced by the method described in Example 4. Purification by chromatography (silica gel, 2% MeOH/CH$_2$Cl$_2$ then 50% EtOAc/isohexane) gave 1.47 g (47%) of the title compound as an orange oil: $^1$H NMR (360 MHz, CDCl$_3$) δ 8.88 (1H, dd, J 5, 2 Hz), 8.07 (1H, dd, J 8, 2 Hz), 7.42 (1H, dd, J 8, 5 Hz), 7.04 (1H, dd, J 9, 9 Hz), 6.85 (1H, dd, J 6, 3 Hz), 6.76–6.81 (1H, m); MS (ES$^+$) m/z 214 [M+H]$^+$.

c) 2-(5-Bromo-2-fluorophenyl)nicotinonitrile 2-(5-Amino-2-fluorophenyl)nicotinonitrile (1.47 g, 6.89 mmol) was bromo-deaminated by the method described in Example 4 to give 1.39 g (71%) of the title compound as a white powder: $^1$H NMR (360 MHz, CDCl$_3$) δ 8.92 (1H, dd, J 5, 1 Hz), 8.10 (1H, dd, J 8, 2 Hz), 7.74 (1H, dd, J 6, 2 Hz), 7.59–7.64 (1H, m), 7.48 (1H, dd, J 8, 5 Hz), 7.15 (1H, dd, J 9, 9 Hz).

d) 2-[2-Fluoro-5-(3-trifluoromethyl-imidazo[1,2-b][1,2,4]triazin-7-yl)phenyl]nicotinonitrile 2-[5-(5,5-Dimethyl-[1,3,2]dioxaborinan-2-yl)-2-fluorophenyl]nicotinonitrile was prepared from 2-(5-bromo-2-fluorophenyl)nicotinonitrile (1.36 g, 4.91 mmol) using the method described in Example 2 to give 467 mg (43%) of an approximately 1:1 mixture of 2-[5-(5,5-dimethyl-[1,3,2]dioxaborinan-2-yl)-2-fluorophenyl]nicotinonitrile and 3-(3-cyanopyridin-2-yl)-4-fluorobenzeneboronic acid as a grey solid. This was coupled to 7-bromo-3-trifluoromethylimidazo[1,2-b][1,2,4]triazine in 40% yield using the method described in Example 3 to give the title compound as a yellow solid: mp 209–211° C. (EtOAc); $^1$H NMR (360 MHz, CDCl$_3$) δ 7.46 (1H, s), 7.54 (2H, m), 8.14 (1H, d, J 1.8 Hz), 8.37 (1H, m), 8.64 (1H, s), 8.82 (1H, s), 8.89 (1H, s). Anal. Found: C, 54.97; H, 2.30; N, 21.74%. Required for C$_{18}$H$_8$F4N$_6$.0.5H$_2$O: C, 54.97, H, 2.31; N, 21.37%.

EXAMPLE 10

3-(1,1-Difluoroethyl)-7-[4-fluoro-3-(pyridin-3-yl)phenyl]imidazo[1,2-b][1,2,4]triazine a) 1,1-Dibromo-3,3-difluorobutan-2-one To N,N-diisopropylamine (4.06 ml, 2.93 g, 29.0 mmol) in THF (20 ml) was added n-butyllithium (11.6 ml of a 2.5 M solution in hexanes; 29.0 mmol) dropwise, maintaining the temperature of the mixture below 5° C. throughout the addition. The resulting solution was stirred at 0° C. for 15 min, and was then added dropwise to a solution of 2,2-difluoropropionic acid ethyl ester (prepared according to the procedure described in U.S. Pat. No. 5,859,051) (2.00 g, 14.5 mmol) and dibromomethane (2.02 ml, 5.04 g, 29.0 mmol) in THF (20 ml) over 30 min with stirring, maintaining the temperature of the mixture below −60° C. throughout the addition. The solution was stirred for 15 min at −78° C. under nitrogen, and was then quenched by the addition of 5 N hydrochloric acid (10 ml). The mixture was allowed to warm to room temperature, and was diluted with water (10 ml). The aqueous phase was separated and washed with diethyl ether (2×30 ml). The combined organic layers were dried over magnesium sulfate, and concentrated in vacuo. The residual oil was purified by flash chromatography on silica gel, eluting with 10% to 20% diethyl ether in 40–60 petroleum ether (UV detection), yielding 1,1-dibromo-3,3-difluorobutan-2-one as a yellow oil (1.65 g, 43%): $^1$H NMR (360 MHz, CDCl$_3$) δ 1.90 (3H, t, J 19.2 Hz), 6.39 (1H, s).

b) 3-Amino-5-(1,1-difluoroethyl)-1,2,4-triazine

This was prepared in 47% yield using a similar procedure to that described in Example 2, step a, but using 1,1-dibromo-3,3-difluorobutan-2-one instead of 1,1-dibromo-3,3,3-trifluoroacetone. The product precipitated from solution without any contaminating regioisomer, and required no further purification: $^1$H NMR (400 MHz, CDCl$_3$) δ 1.95 (3H, t, J 18.8 Hz), 5.51 (1H, br s), 8.97 (1H, s). MS (ES$^+$) m/z 161 [M+H$^+$.

c) 3-(1,1-Difluoroethyl)imidazo[1,2-b[]1,2,4]triazine

This was prepared in 16% yield using a similar procedure to that described in Example 2, step b, but using 3-amino-5-(1,1-difluoroethyl)-1,2,4-triazine instead of 3-amino-5-trifluoromethyl-1,2,4-triazine. The condensation step was performed at reflux overnight, rather than at 60° C. for 20 h then 80° C. for 23 h: $^1$H NMR (400 MHz, CDCl$_3$) δ 2.17 (3H, t, J 18.9 Hz), 8.09 (1H, d, J 1.6 Hz), 8.14 (1H, d, J 1.2 Hz), 8.75 (1H, s).

d) 7-Bromo-3-(1,1-difluoroethyl)imidazo[1,2-b][1,2,4]triazine

This was prepared in 83% yield using a similar procedure to that described in Example 2, step c, but using 3-(1,1-difluoroethyl)imidazo[1,2-b][1,2,4]triazine instead of 3-trifluoromethylimidazo[1,2-b][1,2,4]triazine: $^1$H NMR (400 MHz, CDCl$_3$) δ 2.17 (3H, t, J 18.9 Hz), 8.14 (1H, s), 8.85 (1H, s). MS (ES$^+$) m/z 262, 264 [M+H$^+$.

e) 3-(1,1-Difluoroethyl)-7-[4-fluoro-3-(pyridin-3-yl)phenyl]imidazo[1,2-b][1,2,4]triazine This compound was prepared in 44% yield as described in the final paragraph of Example 2, step d, but using 7-bromo-3-(1,1-difluoroethyl)imidazo[1,2-b][1,2,4]triazine instead of 7-bromo-3-trifluoromethylimidazo[1,2-b][1,2,4]triazine, and using 3-[2-fluoro-5-(4,4,5,5-tetramethyl-[1,3,2]dioxaborolan-2-yl)phenyl]pyridine (prepared as described in Example 3, step f) instead of 2'-fluoro-5'-(4,4,5,5-tetramethyl-[1,3,2]dioxaborolan-2-yl)biphenyl-2-carbonitrile: $^1$H NMR (360 MHz, CDCl$_3$) δ 2.19 (3H, t, J 18.8 Hz), 7.36–7.47 (2H, m), 7.98 (1H, m), 8.08 (1H, m), 8.22 (1H, dd, J 2.3, 7.2 Hz), 8.45 (1H, s), 8.78 (1H, d, J 11.2 Hz), 8.85 (1H, s), 8.88 (1H, s); MS (ES$^+$) m/z 356 [M+H]$^+$. Anal. Found: C, 60.85; H, 3.45; N, 19.69%. Required for C$_{18}$H$_{12}$F$_3$N$_5$: C, 60.85; H, 3.40; N, 19.71%.

EXAMPLE 11

3-tert-Butyl-7-[4-fluoro-3-(pyridin-3-yl)phenyl]imidazo[1,2-b][1,2,4]triazine a) 3-Amino-5-tert-butyl-1,2,4-triazine This was prepared in 51% yield using a similar procedure to that described in Example 2, step a, but using dibromopinacolone instead of 1,1-dibromo-3,3,3-trifluoroacetone. The product precipitated from solution without any contaminating regioisomer, and was washed with diethyl ether to remove traces of the starting dibromoketone: $^1$H NMR (400 MHz, CDCl$_3$) δ 1.32 (9H, s), 5.19 (2H, br s), 8.73 (1H, s).

b) 3-tert-Butylimidazo[1,2-b][1,2,4]triazine

This was prepared in 10% yield using a similar procedure to that described in Example 2, step b, but using 3-amino-5-tert-butyl-1,2,4-triazine instead of 3-amino-5-trifluoromethyl-1,2,4-triazine. The condensation step was performed at reflux overnight, rather than at 60° C. for 20 h then 80° C. for 23 h: $^1$H NMR (360 MHz, CDCl$_3$) δ 1.47 (9H, s), 7.86 (1H, d, J 1.2 Hz), 7.89 (1H, d, J 1.2 Hz), 8.46 (1H, s); MS (ES$^+$) m/z 177 [M+H]$^+$.

c) 7-Bromo-3-tert-butylimidazo[1,2-b][1,2,4]triazine

This was prepared in 71% yield using a similar procedure to that described in Example 2, step c, but using 3-tert-butylimidazo[1,2-b][1,2,4]triazine instead of 3-trifluoromethylimidazo[1,2-b][1,2,4]triazine. The product precipitated cleanly from the reaction mixture, was separated by filtration, and used without further purification: $^1$H NMR (360 MHz, CDCl$_3$) δ 1.48 (9H, s), 7.90 (1H, s), 8.59 (1H, s). MS (ES$^+$) m/z 255, 257 [M+H]$^+$.

d) 3-tert-Butyl-7-[4-fluoro-3-(pyridin-3-yl)phenyl]imidazo[1,2-b][1,2,4]triazine This compound was prepared in 48% yield as described in the final paragraph of Example 2, step d, but using 7-bromo-3-tert-butylimidazo[1,2-b][1,2,4]triazine instead of 7-bromo-3-trifluoromethylimidazo[1,2-b][1,2,4]triazine, and using 3-[2-fluoro-5-(4,4,5,5-tetramethyl-[1,3,2]dioxaborolan-2-yl)phenyl]pyridine (prepared as described in Example 3, step f) instead of 2'-fluoro-5'-(4,4,5,5-tetramethyl-[1,3,2]dioxaborolan-2-yl)biphenyl-2-carbonitrile: $^1$H NMR (360 MHz, CDCl$_3$) δ 1.50 (9H, s), 7.34 (1H, m), 7.44 (1H, dd, J 4.9, 8.1 Hz), 7.94–8.02 (2H, m), 8.19 (1H, dd, J 2.5, 7.4 Hz), 8.21 (1H, s), 8.59 (1H, s), 8.66 (1H, d, J 4.82 Hz), 8.88 (1H, s); MS (ES$^+$) m/z 348 [M+H]$^+$. Anal. Found: C, 66.95; H, 5.15; N, 19.00%. Required for C$_{20}$H$_{18}$FN$_5$·0.75H$_2$O: C, 66.56; H, 5.45; N, 19.41%.

EXAMPLE 12

3-tert-Butyl-7-[4-fluoro-3-(pyridin-2-yl)phenyl]imidazo[1,2-b][1,2,4]triazine a) 2-(2-Fluoro-5-nitrophenyl)pyridine A mixture of 2-bromo-1-fluoro-4-nitrobenzene (2.0 g, 9.1 mmol) and 2-(1,1,1-tributylstannyl)pyridine (3.36 g, 9.11 mmol) in THF (80 ml) and DMF (10 ml) was degassed with nitrogen. [1,1'-Bis(diphenylphosphino)ferrocene]dichloropalladium(II) complex with dichloromethane (200 mg, 3 mol %) was added, and the mixture was heated at reflux for 24 h. More 2-bromo-1-fluoro-4-nitrobenzene (0.60 g, 2.7 mmol) and catalyst (100 mg, 1.5 mol %) were added, and the mixture was heated as before for another 24 h. The solvent was removed in vacuo, and the residue was purified by flash chromatography on silica gel, eluting with 50% dichloromethane in isohexane, then 100% dichloromethane, then 100% ethyl acetate (UV detection). 2-(2-Fluoro-5-nitrophenyl)pyridine was isolated as a colourless solid (2.11 g, 100%): $^1$H NMR (400 MHz, CDCl$_3$) δ

7.30–7.37 (2H, m), 7.80–7.87 (2H, m), 8.27 (1H, m), 8.78 (1H, m), 9.01 (1H, dd, J 3.1, 6.7 Hz); MS (ES$^+$) m/z 219 [M+H]$^+$.

b) 4-Fluoro-3-(pyridin-2-yl)aniline

To 2-(2-fluoro-5-nitrophenyl)pyridine (2.11 g, 9.68 mmol) in ethanol (40 ml), stirred in a water bath at 20° C., was added dry tin(II) chloride (7.10 g, 37.3 mmol) portionwise. The mixture was then stirred at room temperature for 18 h. Aqueous ammonia (40 ml of a 25% solution) was added, and the solvent was removed in vacuo, azeotroping with ethanol to remove traces of water. The residue was sequentially boiled in ethyl acetate and filtered three times. The combined filtrates were concentrated in vacuo to yield 4-fluoro-3-(pyridin-2-yl)aniline as a yellow solid (1.54 g, 85%): $^1$H NMR (400 MHz, CDCl$_3$) δ 3.65 (2H, br s), 6.68 (1H, m), 6.98 (1H, dd, J 8.6, 11.0 Hz), 7.22–7.31 (2H, m), 7.71–7.83 (2H, m), 8.70 (1H, m); MS (ES$^+$) m/z 189 [M+H]$^+$.

c) 2-(5-Bromo-2-fluorophenyl)pyridine

To a solution of copper(II) bromide (2.0 g, 8.6 mmol) in anhydrous acetonitrile (30 ml) was added tert-butyl nitrite (1.64 ml, 1.42 g, 13.8 mmol) dropwise with stirring at 4° C. A solution of 4-fluoro-3-(pyridin-2-yl)aniline (1.54 g, 8.2 mmol) in acetonitrile (10 ml) was added dropwise with stirring over 5 min, then the mixture was allowed to warm to room temperature and stirred for 16 h. The mixture was partitioned between ethyl acetate and 25% aqueous ammonia, and the aqueous phase was further extracted with ethyl acetate. The combined organic layers were washed with saturated brine and were concentrated in vacuo. The residual material was purified by flash chromatography (silica gel, dichloromethane) affording 2-(5-bromo-2-fluorophenyl)pyridine (669 mg, 32%): $^1$H NMR (400 MHz, CDCl$_3$) δ 7.07 (1H, dd, J 8.6, 10.6 Hz), 7.29 (1H, m), 7.48 (1H, m), 7.77–7.79 (2H, m), 8.17 (1H, dd, J 2.5, 6.8 Hz), 8.73 (1H, m); MS (ES$^+$) m/z 252/254 [M]$^+$.

d) 4-Fluoro-3-(pyridin-2-yl)phenylboronic Acid

To 2-(5-bromo-2-fluorophenyl)pyridine (544 mg, 2.16 mmol) and bis(neopentyl glycolato)diborane (585 mg, 2.60 mmol) under nitrogen was added dry potassium acetate (450 mg, 4.58 mmol), anhydrous 1,4-dioxane (8 ml) and DMSO (1 ml). The mixture was degassed with nitrogen, and [1,1'-bis(diphenylphosphino)ferrocene]dichloropalladium(II) complex with dichloromethane (50 mg, 3 mol %) was added. After stirring at 85° C. under nitrogen for 15 h, the mixture was cooled to room temperature, and sodium hydroxide solution (20 ml of a 1 M solution) was added. The mixture was stirred for 10 min, and was then extracted twice with diethyl ether. The combined ether extractions were washed with water, then the combined aqueous layers were filtered through a glass fibre filter paper. The pH of the filtrate was adjusted to 6 by the addition of 2 N hydrochloric acid, precipitating a white solid. This was collected by filtration, washed with water and dried in vacuo at 60° C., and was found to be 4-fluoro-3-(pyridin-2-yl)phenylboronic acid (455 mg, 97%): $^1$H NMR (400 MHz, DMSO) δ 7.30 (1H, dd, J 8.2, 11.7 Hz), 7.41 (1H, m), 7.77 (1H, m), 7.90 (2H, m), 8.16 (2H, s), 8.36 (1H, dd, J 1.6, 8.6 Hz), 8.72 (1H, m).

e) 3-tert-Butyl-7-[4-fluoro-3-(pyridin-2-yl)phenyl]imidazo[1,2-b][1,2,4]triazine This compound was prepared in 29% yield as described in the final paragraph of Example 2, step d, but using 7-bromo-3-tert-butylimidazo[1,2-b][1,2,4]triazine instead of 7-bromo-3-trifluoromethylimidazo[1,2-b][1,2,4]triazine, and using 4-fluoro-3-(pyridin-2-yl)phenylboronic acid instead of 2'-fluoro-5'-(4,4,5,5-tetramethyl-[1,3,2]dioxaborolan-2-yl)biphenyl-2-carbonitrile: $^1$H NMR (400 MHz, CDCl$_3$) δ 1.50 (9H, s), 7.29–7.33 (2H, m), 7.80 (1H, m), 7.86 (1H, m), 8.07 (1H, m), 8.25 (1H, s), 8.59 (1H, s), 8.66 (1H, dd, J 2.3, 7.4 Hz), 8.77 (1H, m); MS (ES$^+$) m/z 348 M+H]$^+$. Anal. Found: C, 66.95; H, 5.15; N, 19.00%. Required for C$_{20}$H$_{18}$FN$_5$.0.75H$_2$O: C, 66.56; H, 5.45; N, 19.41%.

EXAMPLE 13

4,2'-Difluoro-5'-[3-(1-hydroxy-1-methylethyl)imidazo[1,2-b][1,2,4]triazin-7-yl]biphenyl-2-carbonitrile a) 1,1-Dibromo-3-hydroxy-3-methylbutan-2-one To a stirred solution of 3-methyl-3-hydroxy-2-butanone (40 g, 0.392 mol) in anhydrous dichloromethane (2.2 l) under nitrogen was added solid pyridinium tribromide (250.4 g, 0.784 mol) in portions and the mixture was stirred at room temperature for 14 h. The mixture was then washed with dilute aqueous sodium hydrogensulfite (500 ml), then saturated aqueous NaCl (500 ml), dried (Na$_2$SO$_4$), and evaporated in vacuo. The residue was purified by flash chromatography (silica gel, CH$_2$Cl$_2$) to afford 31.4 g (31%) of the title compound as a colourless oil: $^1$H NMR (360 MHz, CDCl$_3$) δ 1.54 (6H, s), 2.45 (1H, br s), 6.62 (1H, s).

b) 2-(3-Amino-[1,2,4]triazin-5-yl)propan-2-ol and 2-(3-amino-[1,2,4]triazin-6-yl)propan-2-ol To a stirred solution of sodium acetate trihydrate (32.9 g, 0.342 mol) in water (90 ml) was added 1,1-dibromo-3-hydroxy-3-methylbutan-2-one (29.6 g, 0.114 mol). The solution was heated at reflux under nitrogen for 30 min, then allowed to cool to room temperature before adding solid aminoguanidine bicarbonate (15.54 g, 0.114 mol). The resulting pale yellow solution (pH 5) was stirred at room temperature for 15 min, then 4 N aqueous NaOH solution (56.9 ml, 0.228 mol) was added and the mixture (pH 10) was stirred under nitrogen for a further 14 h. The solution was continuously extracted with warm dichloromethane over a period of 24 h. After this time the solvent was evaporated to leave a residue which was triturated with diethyl ether to give a solid. The solid was collected by filtration and dried at 60° C. under vacuum to give 8.17 g (47%) of a mixture of two isomers in a 60:40 ratio with the required 2-(3-amino-[1,2,4]triazin-5-yl)propan-2-ol being the major product: NMR (360 MHz, DMSO-d$_6$) δ 1.38 (major) and 1.47 (minor) (6H, s), 5.30 (major) and 5.43 (minor) (1H, br s), 7.01 (major) and 7.06 (minor) (2H, br s), 8.43 (major) and 8.80 (minor) (1H, s); MS (ES$^+$) m/z 155 [M+H]$^+$.

c) 2-(Imidazo[1,2-b][1,2,4]triazin-3-yl)propan-2-ol

A stirred mixture of bromoacetaldehyde diethyl acetal (16.5 ml, 0.106 mol) in concentrated hydrobromic acid (4.13 ml) and water (4.13 ml) was heated at reflux for 40 min, then poured into ethanol (175 ml). The solution was neutralised to pH 7 with solid sodium hydrogencarbonate, then filtered, washing the solid with more ethanol (30 ml). To the filtrate was added a 60:40 mixture of 2-(3-amino-[1,2,4]triazin-5-yl)propan-2-ol and 2-(3-amino-[1,2,4]triazin-6-yl)propan-2-ol (8.17 g, 0.053 mol) and the mixture was stirred at reflux temperature for 6 h. The mixture was evaporated in vacuo, and the residue was triturated with hot dichloromethane and filtered. The solid which was collected was triturated with hot acetone and collected by filtration again to leave a white solid (14 g). The solid was dissolved in water (30 ml) and continuously extracted with hot dichloromethane over a period of 24 h. The organic layer was separated and concentrated under vacuum to leave a thick yellow oil (3 g) which favoured the required isomer in a ratio of 4:1. The required product was obtained in pure form by flash chromatography (silica gel, 2% MeOH/CH$_2$Cl$_2$) to give 2.12 g (23%) of the title compound as a pale yellow solid: $^1$H NMR (360 MHz, CDCl$_3$) δ 1.69 (6H, s), 3.69 (1H, br s), 7.93 (2H, s), 8.70 (1H, s).

d) 2-(7-Bromoimidazo[1,2-b][1,2,4]triazin-3-yl)propan-2-ol

This was prepared in 75% yield by a similar procedure to that described in Example 1, step b, except using 2-(imidazo[1,2-b][1,2,4]triazin-3-yl)propan-2-ol instead of 3-methylimidazo[1,2-b][1,2,4]triazine: $^1$H NMR (360 MHz, CDCl$_3$) δ 1.70 (6H, s), 3.12 (1H, br s), 7.95 (1H, s), 8.80 (1H, s).

e) 4,2'-Difluoro-5'-[3-(1-hydroxy-1-methylethyl)imidazo[1,2-b][1,2,4]triazin-7-yl]biphenyl-2-carbonitrile 5'-(5,5-Dimethyl-[1,3,2]dioxaborinan-2-yl)-4,2'-difluorobiphenyl-2-carbonitrile (see Example 4) was coupled to 2-(7-bromoimidazo[1,2-b][1,2,4]triazin-3-yl)propan-2-ol in 54% yield using a similar procedure to that described in Example 3, step f, to give a yellow solid: mp 215° C.; $^1$H NMR (360 MHz, CDCl$_3$) δ 1.71 (6H, s), 3.27 (1H, br s), 7.35–7.59 (4H, m), 8.09–8.15 (2H, m), 8.26 (1H, s), 8.78 (1H, s); MS (ES$^+$) m/z 392 [M+H]$^+$. Anal. Found: C, 64.38; H, 3.88; N, 17.66%. Required for C$_{21}$H$_{15}$F$_2$N$_5$O: C, 64.45; H, 3.86; N, 17.89%.

EXAMPLE 14

2-{7-[4-Fluoro-3-(pyridin-3-yl)phenyl]imidazo[1,2-b][1,2,4]triazin-3-yl}propan-2-ol This was prepared from 2-(7-bromoimidazo[1,2-b][1,2,4]triazin-3-yl)propan-2-ol in 79% yield by a similar procedure to that described in Example 3, step f, except using 2-(7-bromoimidazo[1,2-b][1,2,4]triazin-3-yl)propan-2-ol instead of 7-bromo-3-(1-fluoro-1-methylethyl)imidazo[1,2-b][1,2,4]triazine, to afford a yellow solid: mp 199–200° C. (EtOAc-CH$_2$Cl$_2$); $^1$H NMR (400 MHz, DMSO-d$_6$) δ 1.57 (6H, s), 5.77 (1H, s), 7.55–7.60 (2H, m), 8.08 (1H, m), 8.25 (1H, m), 8.32 (1H, dd, J 7.4, 2.3 Hz), 8.53 (1H, s), 8.67 (1H, dd, J 4.7, 1.6 Hz), 8.86 (1H, s), 9.04 (1H, s); Anal. Found: C, 64.80; H, 4.56; N, 19.64%. Required for C$_{19}$H$_{16}$FN$_5$O.0.2H$_2$O: C, 64.65; H, 4.68; N, 19.84%.

EXAMPLE 15

2-{7-[4-Fluoro-3-(pyridin-4-yl)phenyl]imidazo[1,2-b][1,2,4]triazin-3-yl}propan-2-ol To a degassed solution of 2-bromo-1-fluoro-4-nitrobenzene (A. Groweiss, *Org. Process Res. Dev.*, 2000, 4, 30–33) (6.44 g, 29.3 mmol), 4-tri-n-butylstannylpyridine (14.0 g, 38.0 mmol), lithium chloride (12.4 g, 293 mmol) and copper(I) iodide (0.56 g, 2.93 mmol) in N,N-dimethylacetamide (40 ml) was added tetrakis(triphenylphosphine)palladium(0) (1.69 g, 1.46 mmol) and the reaction heated at 80° C. for 18 h. After cooling to ambient temperature the solvent was evaporated and the residue was diluted with dichloromethane (800 ml) and the mixture stirred vigorously for 30 min then filtered. The organics were washed with water (500 ml) and brine (300 ml), dried (MgSO$_4$), filtered and evaporated to give a black oil. The residue was purified by chromatography [silica gel, 20–50% EtOAc/isohexane (containing 1% methanol and 1% triethylamine)] to give 4-(2-fluoro-5-nitrophenyl)pyridine as an off-white solid (5.60 g, 88%): $^1$H NMR (360 MHz, CDCl$_3$) δ 7.38 (1H, t, J 9 Hz), 7.50–7.53 (2H, m), 8.30–8.35 (1H, m), 8.41–8.44 (1H, m), 8.76–8.78 (2H, m).

To a solution of 4-(2-fluoro-5-nitrophenyl)pyridine (1.0 g, 5.58 mmol) in ethanol (30 ml) and ethyl acetate (10 ml) was added platinum(IV) oxide (52 mg) and the mixture stirred for 35 min under hydrogen (40 psi). The reaction was filtered through glass microfibre filter paper and the filtrate evaporated to dryness to give 4-fluoro-3-(pyridin-4-yl)phenylamine (862 mg, 100%) as a white solid: $^1$H NMR (360 MHz, CDCl$_3$) δ 3.49 (2H, s), 6.66–6.70 (1H, m), 6.71–6.76 (1H, m), 6.99 (1H, t, J 9 Hz), 7.44–7.46 (2H, m), 8.66 (2H, d, J 5 Hz).

4-Fluoro-3-(pyridin-4-yl)phenylamine (0.58 g, 3.08 mmol) was bromo-deaminated following the procedure described in Example 3, step f (for 4-fluoro-3-(pyridin-3-yl)phenylamine), to give 4-(5-bromo-2-fluorophenyl)pyridine (464 mg, 60%) as a white solid: $^1$H NMR (360 MHz, CDCl$_3$) δ 7.38 (1H, t, J 9 Hz), 7.59–7.62 (2H, m), 7.68–7.73 (1H, m), 7.84 (1H, dd, J 7, 3 Hz), 8.68 (2H, dd, J 5, 3 Hz).

A mixture of 4-(5-bromo-2-fluorophenyl)pyridine (3.8 g, 15.1 mmol), potassium acetate (2.96 g, 30.1 mmol) and bis(pinacolato)diboron (4.21 g, 16.6 mmol) in 1,4-dioxane (50 ml) and dimethylsulfoxide (1 ml) was degassed with nitrogen for 1 h. Dichloro[1,1'-bis(diphenylphosphino)ferrocene]palladium(II) dichloromethane adduct (370 mg, 0.5 mmol) was added and the mixture heated at 90° C. for 18 h. The reaction was cooled to ambient temperature, filtered and the filter-cake washed with diethyl ether. The filtrate was evaporated to dryness and the residue stirred with ice-cold 2 N sodium hydroxide (100 ml) for 20 min. The aqueous mixture was filtered and the filtrate washed with diethyl ether (2×75 ml). The organics were discarded and the aqueous phase cooled to 0° C. before lowering the pH to 8 by addition of 36% hydrochloric acid. The resulting solid was collected by filtration and triturated with diethyl ether to afford 4-fluoro-3-(pyridin-4-yl)benzeneboronic acid as a buff-coloured solid (1.51 g, 46%): $^1$H NMR (360 MHz, DMSO-d$_6$) δ 7.34 (1H, dd, J 11, 8 Hz), 7.61 (2H, d, J 5 Hz), 7.88–7.92 (1H, m), 8.05 (1H, dd, J 8, 1 Hz), 8.26 (2H, s), 8.70 (2H, d, J 5 Hz); MS (ES$^+$) m/z 218 [M+H]$^+$. The aqueous filtrate was extracted with diethyl ether. The organic phase was washed with water, brine, dried (MgSO$_4$), filtered and evaporated to afford 4-[2-fluoro-5-(4,4,5,5-tetramethyl-[1,3,2]dioxaborolan-2-yl)phenyl]pyridine as a dark oil (1.28 g, 29%) that solidified on standing for a few days: $^1$H NMR (360 MHz, CDCl$_3$) δ 1.36 (12H, s), 7.19 (1H, dd, J 11, 8 Hz), 7.50–7.53 (2H, m), 7.82–7.87 (1H, m), 7.93 (1H, dd, J 8, 1 Hz), 8.67 (2H, dd, J 4, 1 Hz); MS (ES$^+$) m/z 300 [M+H]$^+$.

4-Fluoro-3-(pyridin-4-yl)benzeneboronic acid was coupled with 2-(7-bromoimidazo[1,2-b][1,2,4]triazin-3-yl)propan-2-ol in 80% yield by a similar procedure to that described in Example 3, step f, to afford the title compound as a yellow solid: mp 233–237° C. (CH$_2$Cl$_2$-EtOAc-MeOH); $^1$H NMR (400 MHz, DMSO-d$_6$) δ 1.57 (6H, s), 5.78 (1H, s), 7.60 (1H, dd, J 11.0, 8.6 Hz), 7.68–7.70 (2H, m), 8.27 (1H, m), 8.35 (1H, dd, J 7.4, 2.3 Hz), 8.53 (1H, s), 8.73 (2H, m), 9.04 (1H, s); MS (ES$^+$) m/z 350 [M+H]$^+$. Anal. Found: C, 64.87; H, 4.58; N, 19.79%. Required for C$_{19}$H$_{16}$FN$_5$O.0.1H$_2$O: C, 64.98; H, 4.65; N, 19.94%.

EXAMPLE 16

2'-Fluoro-5'-[3-(1-hydroxy-1-methylethyl)imidazo[1,2-b][1,2,4]triazin-7-yl]biphenyl-2-carbonitrile 2'-Fluoro-5'-(4,4,5,5-tetramethyl-[1,3,2]dioxaborolan-2-yl)biphenyl-2-carbonitrile was coupled to 2-(7-bromoimidazo[1,2-b][1,2,4]triazin-3-yl)-propan-2-ol in 29% yield using a similar procedure to that described in Example 3, step f, to give a yellow solid: mp 187° C.; $^1$H NMR (360 MHz, CDCl$_3$) δ 1.71 (6H, s), 3.25 (1H, br s), 7.36–7.84 (5H, m), 8.09–8.16 (2H, m), 8.26 (1H, s), 8.76 (1H, s); MS (ES$^+$) m/z 374 [M+H]$^+$. Anal. Found: C, 67.34; H, 4.30, N. 18.47%. Required for C$_{21}$H$_{16}$FN$_5$O: C, 67.55; H, 4.32; N, 18.76%.

EXAMPLE 17

4-Fluoro-3'-[3-(1-hydroxy-1-methylethyl)imidazo[1,2-b][1,2,4]triazin-7-yl]-biphenyl-2-carbonitrile 2-Bromo-5-fluorobenzonitrile and 3-nitrophenylboronic acid were coupled following the procedure in Example 4 to afford 4-fluoro-3'-nitrobiphenyl-2-carbonitrile as a black solid: $^1$H NMR (360 MHz, CDCl$_3$) δ 7.39–7.48 (2H, m), 7.52–7.64 (1H, m), 7.71 (1H, dd, J 8, 8 Hz), 7.89 (1H, d, J 8 Hz), 8.33–8.37 (2H, m).

4-Fluoro-3'-nitrobiphenyl-2-carbonitrile was reduced following the procedure in Example 4 to give 3'-amino-4-fluorobiphenyl-2-carbonitrile as a brown solid: $^1$H NMR (400 MHz, CDCl$_3$) δ 6.76 (1H, ddd, J 8, 2, 2 Hz), 6.80 (1H, dd, J 2, 2 Hz), 6.87 (1H, ddd, J 8, 1, 1 Hz), 7.27 (1H, dd, J 8, 8 Hz), 7.35 (1H, ddd, J 8, 8, 3 Hz), 7.41–7.51 (2H, m).

3'-Amino-4-fluorobiphenyl-2-carbonitrile was bromo-deaminated following the procedure in Example 4 to give 3'-bromo-4-fluorobiphenyl-2-carbonitrile as a white solid: $^1$H NMR (400 MHz, CDCl$_3$) δ 7.35–7.40 (2H, m), 7.46–7.50 (3H, m), 7.59 (1H, dd, J 2, 1 Hz), 7.64 (1H, dd, J 2, 2 Hz).

3'-Bromo-4-fluorobiphenyl-2-carbonitrile was converted to 4-fluoro-3'-(4,4,5,5-tetramethyl-[1,3,2]dioxaborolan-2-yl)biphenyl-2-carbonitrile following the procedure in Example 4, affording a brown oil that crystallised on standing: $^1$H NMR (400 MHz, CDCl$_3$) δ 1.36 (12H, s), 7.32–7.37 (1H, m), 7.43–7.54 (3H, m), 7.63–7.68 (1H, m), 7.88–7.90 (2H, m).

4-Fluoro-3'-(4,4,5,5-tetramethyl-[1,3,2]dioxaborolan-2-yl)biphenyl-2-carbonitrile was coupled to 2-(7-bromoimidazol-1,2-b) 1,2,4]triazin-3-yl)-propan-2-ol in 32% yield using a similar procedure to that described in Example 3, step f, to give a yellow solid: mp 175° C.; $^1$H NMR (360 MHz, CDCl$_3$) δ 1.71 (6H, s), 3.25 (1H, br s), 7.41–7.67 (5H, m), 8.01 (1H, m), 8.24 (1H, m), 8.31 (1H, s), 8.78 (1H, s); MS (ES$^+$) m/z 374 [M+H]$^+$. Anal. Found: C, 67.38; H, 4.27; N, 18.51%. Required for C$_{21}$H$_{16}$FN$_5$O: C, 67.55; H, 4.32; N, 18.76%.

EXAMPLE 18

6,2'-Difluoro-5'-[3-(1-hydroxy-1-methylethyl)imidazo[1,2-b][1,2,4]triazin-7-yl]biphenyl-2-carbonitrile A mixture of 2,3-difluorobenzonitrile (19.0 g, 137 mmol) and ethanol (200 ml) pre-saturated with ammonia gas was heated at 140° C. in an autoclave for 8 h (terminal pressure 200 psi). The mixture was allowed to cool to ambient temperature and evaporated to dryness. The residue was dissolved in water (400 ml) and extracted with diethyl ether (2×300 ml). The combined organics were washed with water (300 ml) and brine (250 ml), dried over anhydrous magnesium sulfate, filtered and evaporated. Trituration with isohexane (150 ml) afforded 2-amino-3-fluorobenzonitrile (9.8 g, 50%) as an off-white solid: $^1$H NMR (360 MHz, CDCl$_3$) δ 4.47 (2H, s), 6.65–6.71 (1H, m), 7.14–7.20 (2H, m).

2-Amino-3-fluorobenzonitrile (9.8 g, 71.9 mmol) was bromo-deaminated as described in Example 4 to afford 2-bromo-3-fluorobenzonitrile as a pale brown solid: $^1$H NMR (360 MHz, CDCl$_3$) δ 7.62–7.68 (1H, m), 7.74–7.85 (1H, ddd, J 9, 9, 1 Hz), 7.74–7.85 (1H, ddd, J 8, 1, 1 Hz).

2-Bromo-3-fluorobenzonitrile (2.50 g, 12.5 mmol) was coupled to 2-(2-fluoro-5-nitrophenyl)-4,4,5,5-tetramethyl-[1,3,2]dioxaborolane as described in Example 4 to give 6,2'-difluoro-5'-nitrobiphenyl-2-carbonitrile as a black solid: $^1$H NMR (360 MHz, CDCl$_3$) δ 7.40–7.44 (1H, m), 7.47–7.52 (1H, m), 7.59–7.67 (2H, m), 8.37–8.44 (2H, m).

6,2'-Difluoro-5'-nitrobiphenyl-2-carbonitrile (3.25 g, 12.5 mmol) was reduced using the procedure described in Example 4 to give 5'-amino-6,2'-difluorobiphenyl-2-carbonitrile as a brown oil: $^1$H NMR (360 MHz, CDCl$_3$) δ 3.74 (2H, s), 6.68 (1H, m), 6.73–6.77 (1H, m), 7.02 (1H, dd, J 9, 9 Hz), 7.37–7.49 (2H, m), 7.56–7.65 (1H, m).

5'-Amino-6,2'-difluorobiphenyl-2-carbonitrile was bromo-deaminated as described in Example 4 to furnish 5'-bromo-6,2'-difluorobiphenyl-2-carbonitrile as a pale brown solid: $^1$H NMR (360 MHz, CDCl$_3$) δ 7.13 (1H, dd, J 9, 9 Hz), 7.37–7.49 (2H, ddd, J 9, 9, 1 Hz), 7.57–7.62 (4H, m).

5'-Bromo-6,2'-difluorobiphenyl-2-carbonitrile was converted to 6,2'-difluoro-5'-(4,4,5,5-tetramethyl-[1,3,2]dioxaborolan-2-yl)biphenyl-2-carbonitrile using the procedure described in Example 4. This gave a brown oil that crystallised on standing: $^1$H NMR (360 MHz, CDCl$_3$) δ 1.34 (12H, s), 7.21 (1H, dd, J 8, 2 Hz), 7.38–7.51 (2H, m), 7.57–7.59 (1H, m), 7.85 (1H, dd, J 8, 2 Hz), 7.90–7.94 (1H, m).

6,2'-Difluoro-5'-(4,4,5,5-tetramethyl-[1,3,2]dioxaborolan-2-yl)-biphenyl-2-carbonitrile was coupled to 2-(7-bromoimidazo[1,2-b][1,2,4]triazin-3-yl)propan-2-ol in 32% yield using a similar procedure to that described in Example 3, step f, to give a yellow solid: mp 206° C.; $^1$H NMR (360 MHz, CDCl$_3$) δ 1.71 (6H, s), 3.28 (1H, br s), 7.37–7.66 (4H, m), 8.15 (2H, m), 8.26 (1H, s), 8.78 (1H, s); MS (ES$^+$) m/z 392 [M+H]$^+$. Anal. Found: C, 64.66; H, 3.93, N, 17.71%. Required for C$_{21}$H$_{15}$F$_2$N$_5$O: C, 64.45; H, 3.86; N, 17.89%.

EXAMPLE 19

2-{7-[2-Fluoro-3-(pyridin-4-yl)phenyl]imidazo[1,2-b][1,2,4]triazin-3-yl}propan-2-ol A mixture of 4-bromopyridine hydrochloride (7.5 g, 38.6 mmol) and 2-fluorobenzeneboronic acid (6.75 g, 48 mmol) in tetrahydrofuran (80 ml) and 2 M sodium carbonate (58 ml) was degassed with nitrogen for 20 min then tetrakis (triphenylphosphine)palladium(0) (1.34 g, 1.2 mmol) was added and the reaction heated at reflux for 24 h. The mixture was cooled to ambient temperature then partitioned between ethyl acetate and 10% sodium carbonate. The organic layer was washed with water, then saturated sodium hydrogencarbonate, dried over anhydrous magnesium sulfate, filtered and pre-adsorbed onto silica. Purification by chromatography [silica gel, 20–40% EtOAc/isohexane (containing 0.5% triethylamine)] afforded 4-(2-fluorophenyl)pyridine as a yellow oil that crystallised on standing (6.26 g, 94%): $^1$H NMR (400 MHz, CDCl$_3$) δ 7.17–7.22 (1H, m), 7.26 (1H, ddd, J 8, 8, 1 Hz), 7.38–7.44 (1H, m), 7.47–7.50 (3H, m), 8.68 (2H, d, J 4 Hz); MS (ES$^+$) m/z 174 [M+H]$^+$.

A cooled (−78° C.) solution of n-butyllithium (15.2 ml of a 2.5 M solution in hexanes, 38.0 mmol) in tetrahydrofuran (100 ml) was treated with 2,2,6,6-tetramethylpiperidine (6.69 ml, 39.8 mmol) and stirring at −78° C. was continued for 15 min. The reaction was then treated with a cooled (0°

C.) solution of 4-(2-fluorophenyl)pyridine (6.26 g, 36.1 mmol) in tetrahydrofuran (20 ml) added dropwise over 10 min. This mixture was stirred at −78° C. for 2 h and then treated with trimethyl borate (8.16 ml, 72.3 mmol) added dropwise over 5 min. The reaction was stirred at −78° C. for 10 min then allowed to warm to ambient temperature. Next, 2 N hydrochloric acid (10 ml) was added and the mixture stirred for 30 min, then evaporated to dryness. The residue was stirred with 2 N hydrochloric acid (100 ml) for 1 h and then taken to pH 14 with 2 N sodium hydroxide (ca. 150 ml). This was washed with diethyl ether and the aqueous layer was cooled to 0° C. and adjusted to pH 8 with 36% hydrochloric acid. After stirring at 0° C. for 1 h the resulting solid was collected by filtration and dried to afford 5.20 g (66%) of 2-fluoro-3-(pyridin-4-yl)benzeneboronic acid as a white solid: MS (ES$^+$) m/z 218 [M+H]$^+$.

2-Fluoro-3-(pyridin-4-yl)benzeneboronic acid was coupled with 2-(7-bromoimidazo[1,2-b][1,2,4]triazin-3-yl)propan-2-ol in 70% yield by a similar procedure to that described in Example 3, step f, to afford the title compound as a yellow solid: mp 221–223° C. (CH$_2$Cl$_2$-EtOAc-MeOH); $^1$H NMR (400 MHz, DMSO-d$_6$) δ 1.57 (6H, s), 5.79 (1H, s), 7.55 (1H, t, J 7.8 Hz), 7.66 (2H, m), 7.73 (1H, m), 8.15 (1H, m), 8.29 (1H, d, J 2.3 Hz), 8.71 (2H, m), 9.02 (1H, s); MS (ES$^+$) m/z 350 [M+H]$^+$. Anal. Found: C, 65.06; H, 4.62; N, 19.91%. Required for C$_{19}$H$_{16}$FN$_5$O: C, 65.32; H, 4.62; N, 20.05%.

EXAMPLE 20

2-{2-Fluoro-5-[3-(1-hydroxy-1-methylethyl)imidazo[1,2-b][1,2,4]triazin-7-yl]phenyl}nicotinonitrile A degassed solution of 2-chloronicotinonitrile (2.0 g, 14.4 mmol), 2-(2-fluoro-5-nitrophenyl)-4,4,5,5-tetramethyl-[1,3,2]dioxaborolane (5 g, 18.7 mmol) and potassium fluoride (2.8 g, 47.5 mmol) was formed in tetrahydrofuran (150 ml) with water (5 ml). This mixture was then treated with tris(dibenzylideneacetone)dipalladium(0) (264 mg, 0.29 mmol) followed by tri-tert-butylphosphine (2.9 ml of a 0.2 M solution in 1,4-dioxane, 0.58 mmol) and the reaction was heated at 60° C. for 20 h and then cooled to ambient temperature. The reaction mixture was poured into water (300 ml) and extracted with ethyl acetate (3×200 ml). The organic extracts were dried over anhydrous magnesium sulfate, filtered and evaporated to a brown solid. Purification by chromatography on silica gel eluting with dichloromethane gave 2-(2-fluoro-5-nitrophenyl)-nicotinonitrile as a yellow solid: $^1$H NMR (360 MHz, CDCl$_3$) δ 8.97 (1H, dd, J 2, 5 Hz), 8.56 (1H, dd, J 3, 6 Hz), 8.40–8.45 (1H, m), 8.15 (1H, dd, J 2, 8 Hz), 7.55 (1H, dd, J 5, 8 Hz), 7.43 (1H, t, J 9 Hz); MS (ES$^+$) m/z 244 [M+H]$^+$.

A solution of 2-(2-fluoro-5-nitrophenyl)nicotinonitrile (1.2 g, 4.9 mmol) and platinum(IV) oxide in ethanol (50 ml) with ethyl acetate (50 ml) was reduced under 40 psi hydrogen for 30 minutes then filtered and the solvent removed to give an orange oil. Purification by chromatography (silica gel, 1% MeOH/CH$_2$Cl$_2$) gave 2-(5-amino-2-fluorophenyl)-nicotinonitrile as an orange oil: $^1$H NMR (360 MHz, CDCl$_3$) δ 8.88 (1H, dd, J 2, 5 Hz), 8.07 (1H, dd, J 2, 8 Hz), 7.42 (1H, dd, J 5, 8 Hz), 7.04 (1H, t, J 9 Hz), 6.85 (1H, dd, J 3, 6 Hz), 6.76–6.81 (1H, m); MS (ES$^+$) m/z 214 [M+H]$^+$.

A solution of 2-(5-amino-2-fluorophenyl)nicotinonitrile (3.5 g, 16.4 mmol) was formed in 48% hydrobromic acid (80 ml) and cooled to 3° C. (internal temperature). A solution of sodium nitrite (1.3 g, 18.9 mmol) in water (3 ml) was then added dropwise keeping the internal temperature <5° C. Stirring at <5° C. was continued for 1 h. A solution of copper(I) bromide (8.23 g, 57 mmol) in 48% hydrobromic acid (10 ml) was added dropwise and the mixture stirred at 5° C. for 10 min then warmed to 50° C. for 1 h. The reaction mixture was cooled to 0° C. and carefully neutralised with aqueous sodium hydroxide (4 N). Aqueous ammonia solution (10 ml, 33%) was then added and the blue solution extracted with ethyl acetate (3×100 ml). The organic extracts were combined, dried over anhydrous magnesium sulfate, filtered and evaporated to a brown solid. Purification by chromatography (silica gel, CH$_2$Cl$_2$) gave 2-(5-bromo-2-fluorophenyl)-nicotinonitrile as a white solid: $^1$H NMR (360 MHz, CDCl$_3$) δ 8.92 (1H, dd, J 5, 1 Hz), 8.10 (1H, dd, J 2, 8 Hz), 7.74 (1H, dd, J 2, 6 Hz), 7.59–7.64 (1H, m), 7.48 (1H, dd, J 5, 8 Hz), 7.15 (1H, t, J 9 Hz).

A degassed solution of 2-(5-bromo-2-fluorophenyl) nicotinonitrile (1.53 g, 5.5 mmol) and bis(neopentyl glycolato)diboron (1.37 g, 6.1 mmol) was formed in 1,4-dioxane (50 ml) with dimethylsulphoxide (1 ml). Potassium acetate (1.08 g, 11.0 mmol) and dichloro[1,1'-bis(diphenylphosphino)ferrocene]palladium(II) dichloromethane adduct (60 mg, 0.1 mmol) were added and the mixture was stirred at 80° C. for 18 h. The reaction was allowed to cool to ambient temperature and the solvent removed under reduced pressure. The residue was dissolved in 2 N sodium hydroxide solution (50 ml) and filtered. The filtrate was washed with diethyl ether (3×50 ml) then cooled to 0° C. and neutralised with concentrated hydrochloric acid. The resulting precipitate was filtered and dried over phosphorus pentoxide to give 4-fluoro-3-(2-nicotinonitrile)-phenylboronic acid as a white solid: MS (ES$^+$) m/z 242 [M+H]$^+$.

A degassed solution of 4-fluoro-3-(2-nicotinonitrile)phenylboronic acid (50 mg, 0.21 mmol) and 2-(7-bromoimidazo[1,2-b][1,2,4]triazin-3-yl)-propan-2-ol (51 mg, 0.20 mmol) was formed in ethylene glycol dimethyl ether (3 ml) with aqueous sodium carbonate (1 ml, 2 M). Tetrakis(triphenylphosphine)palladium(0) (50 mg, 0.05 mmol) was added and the mixture stirred at 65° C. for 18 h. The reaction was allowed to cool to room temperature then poured into water (20 ml) and extracted with ethyl acetate (3×20 ml). The organic phases were combined, dried over anhydrous magnesium sulphate, filtered and evaporated to an orange solid. Purification by chromatography (silica gel, 3% MeOH/CH$_2$Cl$_2$) gave the title compound as a yellow solid: $^1$H NMR (400 MHz, CDCl$_3$) δ 1.71 (6H, s), 3.33 (1H, s), 7.41 (1H, t, J 9 Hz), 7.51 (1H, dd, J 8, 5 Hz), 8.14 (1H, dd, J 8, 2 Hz), 8.18–8.22 (1H, m), 8.28 (1H, s), 8.31 (1H, dd, J 7, 2 Hz), 8.79 (1H, s), 8.96 (1H, dd, J 5, 2 Hz); MS (ES$^+$) m/z 375 [M+H]$^+$.

EXAMPLE 21

7-[6-Fluoro-2'-(methanesulfonyl)biphenyl-3-yl]-3-trifluoromethylimidazo[1,2-b][1,2,4]triazine a) 2-Fluoro-2'-methylthio-5-nitrobiphenyl A mixture of 2-bromo-1-fluoro-4-nitrobenzene (5.89 g, 26.8 mmol), 2-(methylthio)benzeneboronic acid (5.62 g, 33.5 mmol) and potassium fluoride (5.13 g, 88.3 mmol) in THF (70 ml) was degassed with nitrogen for 30 min. This mixture was then treated with tris(dibenzylideneacetone)dipalladium(0) (496 mg, 0.541 mmol) followed by tri-tert-butylphosphine (5.35 ml of a 0.2 M solution in 1,4-dioxane, 1.07 mmol) and the reaction was degassed for a further 10 min. The resulting slurry was then heated at 50° C. for 16 h under nitrogen. After cooling, the reaction mixture was partitioned between ethyl acetate (300 ml) and water (300 ml). The organic layer was washed with saturated aqueous NaCl (200 ml), dried (Na$_2$SO$_4$), and evaporated. Purification by chromatography (silica gel, 5–10% EtOAc/isohexane) gave 6.95 g (99%) of the title compound as a pale yellow solid: $^1$H NMR (360 MHz, CDCl$_3$) δ 2.42 (3H, s), 7.21–7.32 (3H, m), 7.37 (1H, d, J 7.4 Hz), 7.44 (1H, td, J 7.7, 1.6 Hz), 8.27–8.31 (2H, m).

b) 6-Fluoro-2'-(methylthio)biphenyl-3-ylamine

A solution of 2-fluoro-2'-methylthio-5-nitrobiphenyl (6.00 g, 22.8 mmol) in tetrahydrofuran (50 ml) and ethanol (50 ml) was treated with tin(II) chloride dihydrate (25.70 g, 113.9 mmol) and the mixture was stirred at ambient temperature for 25 h. The solvent was evaporated and the residue stirred with 2 N sodium hydroxide solution (240 ml) for 18 h. The resulting suspension was extracted with dichloromethane (3×200 ml). The combined organic extracts were dried (MgSO$_4$) and evaporated. The residue was purified by flash chromatography (silica gel, 35% EtOAc/isohexane) to give 5.20 g (98%) of the title compound as a white solid: $^1$H NMR (360 MHz, CDCl$_3$) δ 2.39 (3H, s), 6.60 (1H, dd, J 2.8, 6.0 Hz), 6.646.68 (1H, m), 6.94 (1H, t, J 8.9 Hz), 7.19–7.20 (2H, m), 7.30 (1H, d, J 7.7 Hz), 7.33–7.37 (1H, m).

c) 5-Bromo-2-fluoro-2'-(methylthio)biphenyl

To a solution of 6-fluoro-2'-(methylthio)biphenyl-3-ylamine (0.3969 g, 1.70 mmol) in 1,4-dioxane (2.1 ml) was added 48% aqueous hydrobromic acid (8 ml) and the mixture was cooled to 3° C. before the dropwise addition of sodium nitrite (0.1365 g, 1.98 mmol) in water (0.5 ml) over 5 min, while the temperature was kept below 5° C. The resulting mixture was stirred at 4±1° C. for 2 h 40 min then more sodium nitrite (0.0255 g, 0.37 mmol) in water (0.1 ml) was added dropwise and the mixture was stirred at 3° C. for 50 min. A cooled (3° C.) solution of copper(I) bromide (0.7443 g, 5.19 mmol) in 48% hydrobromic acid (2.4 ml) was added and the mixture was stirred at 3° C. for 15 min then heated to 50° C. for 1 h. The mixture was cooled to ambient temperature, diluted with water (50 ml) and extracted with ethyl acetate (4×35 ml). The combined organics were washed with 1 M aqueous Na$_2$SO$_3$ solution (30 ml), then saturated aqueous NH$_4$Cl solution (30 ml), dried (MgSO$_4$), and evaporated to give a brown oil. Purification by chromatography (silica gel, 0–2% EtOAc/isohexane) gave 0.2868 g (57%) of the title compound as a white solid: $^1$H NMR (360 MHz, CDCl$_3$) δ 2.40 (3H, s), 7.04 (1H, t, J 8.8 Hz), 7.16–7.24 (2H, m), 7.32 (1H, d, J 7.7 Hz), 7.36–7.51 (4H, m).

d) 5-Bromo-2-fluoro-2'-(methanesulfonyl)biphenyl

To a solution of 5-bromo-2-fluoro-2'-(methylthio) biphenyl (0.1165 g, 0.392 mmol) in anhydrous dichloromethane (7 ml) under nitrogen, cooled in an ice-water bath, was added portionwise, over 5 min, 3-chloroperoxybenzoic acid (55%, 0.3086 g, 0.984 mmol). The mixture was stirred for 30 min, the cooling bath was removed and stirring was continued for a further 6 h. The mixture was diluted with dichloromethane (20 ml) and washed with 5% aqueous NaHCO$_3$ (2×20 ml), then saturated aqueous NaCl (10 ml), dried (MgSO$_4$), and evaporated. The residue was purified by flash chromatography (silica gel, 30% EtOAc/isohexane) to afford 99.7 mg (77%) of the title compound as a colourless oil: $^1$H NMR (360 MHz, CDCl$_3$) δ 2.90 (3H, s), 7.05 (1H, t, J 8.9 Hz), 7.37 (1H, dd, J 7.4, 1.4 Hz), 7.49 (1H, dd, J 6.5, 2.5 Hz), 7.51–7.55 (1H, m), 7.64 (1H, td, J 7.6, 1.5 Hz), 7.69 (1H, td, J 7.5, 1.5 Hz), 8.21 (1H, dd, J 7.7, 1.4 Hz).

e) 2-(6-Fluoro-2'-(methanesulfonyl)biphenyl-3-yl)-4,4,5,5-tetramethyl-[1,3,2]dioxaborolane A mixture of 5-bromo-2-fluoro-2'-(methanesulfonyl) biphenyl (0.7013 g, 2.13 mmol), dried potassium acetate (0.4182 g, 4.26 mmol) and bis(pinacolato)diboron (0.6223 g, 2.45 mmol) in 1,4-dioxane (4.9 ml) and dimethylsulfoxide (0.1 ml) was degassed by bubbling nitrogen through the mixture for 45 min. Dichloro[1,1'-bis(diphenylphosphino) ferrocene]-palladium(II) dichloromethane adduct (52.2 mg, 0.0639 mmol) was added and the mixture was stirred at 90° C. under nitrogen for 16 h. After allowing to cool, the mixture was filtered through glass fibre paper, and the solid was washed with a little dichloromethane. The combined filtrates were evaporated in vacuo and the residue was partitioned between 2 M aqueous NaOH (10 ml) and diethyl ether (10 ml). The aqueous layer was washed with more diethyl ether (10 ml), then acidified to pH 6 with concentrated hydrochloric acid, while cooling in an ice bath, causing a solid to precipitate. After leaving in a fridge overnight, the solid was collected by filtration, washed with water and dried under vacuum to leave 0.8088 g (100%) of the title compound as a pale grey solid: $^1$H NMR (360 MHz, CDCl$_3$) δ 1.33 (12H, s), 2.87 (3H, s), 7.16 (1H, dd, J 8.4, 9.8 Hz), 7.38 (1H, dd, J 1.2, 7.2 Hz), 7.60 (1H, m), 7.66 (1H, m), 7.78 (1H, dd, J 1.4, 8.1 Hz), 7.85–7.89 (1H, m), 8.20 (1H, dd, J 1.1, 7.7 Hz).

f) 7-[6-Fluoro-2'-(methanesulfonyl)biphenyl-3-yl]-3-trifluoromethylimidazo[1,2-b][1,2,4]triazine This was prepared in 89% yield by a similar procedure to that described in Example 3, step f, except using 7-bromo-3-trifluoromethylimidazo[1,2-b][1,2,4]triazine and 2-(6-fluoro-2'-(methanesulfonyl)biphenyl-3-yl)-4,4,5,5-tetramethyl-[1,3,2]dioxaborolane instead of 7-bromo-3-(1-fluoro-1-methylethyl)imidazo[1,2-b][1,2,4]triazine and 3-[2-fluoro-5-(4,4,5,5-tetramethyl-[1,3,2]dioxaborolan-2-yl)phenyl]pyridine: $^1$H NMR (360 MHz, CDCl$_3$) δ 2.93 (3H, s), 7.37 (1H, td, J 1.6, 7.5 Hz), 7.47 (1H, dd, J 1.2, 7.4 Hz), 7.69 (1H, td, J 1.5, 7.8 Hz), 7.75 (1H, td, J 1.5, 7.4 Hz), 8.17–8.21 (2H, m), 8.27 (1H, dd, J 1.4, 8.0 Hz), 8.61 (1H, s), 8.78 (1H, s); MS (ES$^+$) m/z 437 [M+H]$^+$. Anal. Found: C, 52.15; H, 2.85; N, 12.74%. Required for C$_{19}$H$_{12}$F$_4$N$_4$O$_2$S: C, 52.29; H, 2.77; N, 12.84%.

EXAMPLE 22

3'-[3-(1-Hydroxy-1-methylethyl)imidazo[1,2-b][1,2,4]triazin-7-yl]biphenyl-2-carbonitrile 3'-(4,4,5,5-Tetramethyl-[1,3,2]dioxaborolan-2-yl) biphenyl-2-carbonitrile (see Example 1, step c) was coupled to 2-(7-bromoimidazo[1,2-b][1,2,4]triazin-3-yl)propan-2-ol in 29% yield using a similar procedure to that described in Example 3, step f, to give a yellow solid: mp 166° C.; $^1$H NMR (360 MHz, CDCl$_3$) δ 1.71 (6H, s), 3.50 (1H, br s), 7.49–7.71 (5H, m), 7.83 (1H, m), 8.10 (1H, m), 8.27 (1H, s), 8.31 (1H, m), 8.79 (1H, s); MS (ES$^+$) m/z 356 [M+H]$^+$.

EXAMPLE 23

2-{7-[3-(3,5-Difluoropyridin-2-yl)-4-fluorophenyl]imidazo[1,2-b][1,2,4]triazin-3-yl}propan-2-ol To a degassed mixture of 2,4,6-tribromo-3,5-difluoropyridine (4.26 g, 12.1 mmol), 2-(2-fluoro-5-nitrophenyl)-4,4,5,5-tetramethyl-[1,3,2]dioxaborolane (2.80 g, 10.4 mmol), aqueous sodium carbonate (10 ml of a 2 M solution), and tetrahydrofuran (40 ml) was added tetrakis (triphenylphosphine)palladium(0) (0.67 g). The mixture was then stirred at 55° C. for 48 h under an atmosphere of nitrogen. The reaction mixture was then partitioned between water and ethyl acetate. The organic layer was separated and evaporated, and the residue chromatographed (silica gel, 20–40% $CH_2Cl_2$/isohexane) to afford 1.209 g of 2,4-dibromo-3,5-difluoro-6-(2-fluoro-5-nitrophenyl)pyridine as a solid: $^1$H NMR (400 MHz, $CDCl_3$) δ 7.37 (1H, t, J 8.8 Hz), 8.38 (1H, m), 8.55 (1H, dd, J 2.9, 6.1 Hz).

To 2,4-dibromo-3,5-difluoro-6-(2-fluoro-5-nitrophenyl)pyridine (1.20 g, 2.91 mmol) dissolved in dichloromethane (30 ml) was added triethylamine (3 ml) and ethanol (80 ml), followed by 10% palladium on carbon (0.536 g). The mixture was then shaken under an atmosphere of hydrogen gas at 45 psi until complete reaction was indicated by TLC (0.25 to 3.5 h). The catalyst was then removed by filtration, and the solvent was stripped at reduced pressure to afford 3-(3,5-difluoropyridin-2-yl)-4-fluorophenylamine, which was used subsequently without further purification: MS ($ES^+$) m/z 225 $[M+H]^+$.

To 3-(3,5-difluoropyridin-2-yl)-4-fluorophenylamine was added 1,4-dioxane (5 ml) and 48% aqueous hydrogen bromide (15 ml). The solution was cooled to −10° C., and a solution of sodium nitrite (0.252 g) in water (1 ml) was added dropwise with stirring to maintain an internal temperature below −5° C. The mixture was then stirred for a further 1 h at 0 to −5° C., then a solution of copper(I) bromide (1.283 g) in 48% aqueous hydrogen bromide (5 ml) was added slowly with stirring to maintain a reaction temperature below 10° C. The mixture was then stirred at 10° C. for 1 h, room temperature for a further hour, and then heated at 35° C. for 0.5 h. The reaction mixture was then cooled in an ice bath and 4 N aqueous sodium hydroxide (41 ml) was added slowly with stirring, followed by 30% aqueous ammonia (15 ml). The resulting mixture was extracted with ethyl acetate. The organic extracts were evaporated and the residue subjected to chromatography (silica gel, 10% $Et_2O$/isohexane) to afford 2-(5-bromo-2-fluorophenyl)-3,5-difluoropyridine (0.48 g) as a colourless solid: MS ($ES^+$) m/z 288, 290 $[M+H]^+$.

To 2-(5-bromo-2-fluorophenyl)-3,5-difluoropyridine (0.746 g, 2.59 mmol) and bis(neopentyl glycolato)diboron (0.704 g) was added dry 1,4-dioxane (9 ml) and dry dimethylsulfoxide (1.1 ml), followed by dry potassium acetate (0.542 g) and dichloro[1,1'-bis(diphenylphosphino)ferrocene]palladium(II) dichloromethane adduct (0.080 g). The mixture was thoroughly degassed with nitrogen, and then stirred at 85° C. for 24 h. On cooling to room temperature, 1 N aqueous sodium hydroxide (24 ml) was added, and the mixture stirred for 0.5 h. Diethyl ether was added and the aqueous phase was separated and washed with diethyl ether. The organic extracts were washed with water, and the combined aqueous phases were filtered, then acidified to pH 5 by addition of 2 N aqueous hydrochloric acid (12 ml). The resulting solid was collected by filtration, washed with water, and dried in vacuo at 60° C. to afford 0.618 g of 4-fluoro-3-(3,5-difluoropyridin-2-yl)phenylboronic acid as a colourless solid: $^1$H NMR (400 MHz, DMSO-$d_6$) δ 8.69 (1H, d, J 2.3 Hz), 8.21 (2H, s), 7.94–8.14 (3H, m), 7.34 (1H, dd, J 8.2, 10.6 Hz).

To 4-fluoro-3-(3,5-difluoropyridin-2-yl)phenylboronic acid (0.40 g) and 2-(7-bromoimidazo[1,2-b][1,2,4]triazin-3-yl)propan-2-ol (0.391 g) was added tetrahydrofuran (5 ml) and 2 N aqueous sodium carbonate (1.5 ml). Tetrakis(triphenylphosphine)palladium(0) (0.07 g) was added, the mixture was thoroughly degassed with nitrogen, and then stirred at 60° C. for 24 h. On cooling to room temperature, the reaction was partitioned between water and ethyl acetate. The organic extracts were evaporated, and the residue was subjected to chromatography (silica gel, 35% EtOAc/$CH_2Cl_2$). The product was crystallised from dichloromethane/isohexane, and the resulting pale yellow solid was collected by filtration and dried in vacuo at 60° C. to afford the title compound: $^1$H NMR (400 MHz, DMSO-$d_6$) δ 1.56 (6H, s), 5.76 (1H, s), 7.58 (1H, dd, J 8.8, 10 Hz), 8.17 (1H, m), 8.29–8.36 (2H, m), 8.48 (1H, s), 8.74 (1H, d, J 2.3 Hz), 9.02 (1H, s); MS ($ES^+$) m/z 386 $[M+H]^+$.

EXAMPLE 24

4-{2-Fluoro-5-[3-(1-hydroxy-1-methylethyl)imidazo[1,2-b][1,2,4]triazin-7-yl]phenyl}nicotinonitrile 4-Bromonicotinaldehyde was prepared using the method of Kelly et al. (*Tetrahedron Lett.*, 1993, 34, 6173–6176).

4-Bromonicotinonitrile was prepared from 4-bromonicotinaldehyde by the method of D. B. Reitz et al. (*Bioorg. Med. Chem. Lett.*, 1994, 4, 99–104).

A mixture of 4-bromonicotinonitrile (1.00 g, 5.46 mmol), 2-(2-fluoro-5-nitrophenyl)-4,4,5,5-tetramethyl-[1,3,2]dioxaborolane (1.90 g, 7.10 mmol) and potassium fluoride (1.05 g, 18.03-mmol) in tetrahydrofuran (50 ml) was degassed with nitrogen for 30 min then treated with tris(dibenzylideneacetone)dipalladium(0) (0.05 g, 0.05 mmol) followed by tri-tert-butylphosphine (0.60 ml of a 0.2 M solution in 1,4-dioxane, 0.11 mmol) and then the reaction was stirred at ambient temperature for 30 min before heating at 50° C. for 1 h to complete the coupling. The slurry-like reaction mixture was then diluted with water (100 ml) and stirred at ambient temperature for 90 min. The resulting solid was collected by filtration, washed with water then with isohexane, and finally dried under vacuum over phosphorus pentoxide, to afford 4-(2-fluoro-5-nitrophenyl)-nicotinonitrile as a white solid: $^1$H NMR (400 MHz, $CDCl_3$) δ 7.44–7.52 (2H, m), 8.38–8.47 (2H, m), 8.95 (1H, d, J 5 Hz), 9.06 (1H, s).

A cooled (0° C.) suspension of 4-(2-fluoro-5-nitrophenyl)-nicotinonitrile (1.28 g, 5.26 mmol) in ethanol (25 ml) and tetrahydrofuran (25 ml) was treated with tin(II) chloride dihydrate (4.0 g, 190 mmol) and the mixture was stirred to ambient temperature over 12 h. The solvent was removed in vacuo and the residue treated with ice-cold 2 N sodium hydroxide (40 ml). The resulting slurry was stirred for 60 min then extracted with dichloromethane (2×30 ml). The organics were combined, washed with water, brine, dried over anhydrous magnesium sulfate, filtered and concentrated to give a yellow solid: $^1$H NMR (400 MHz, $CDCl_3$) δ 3.70 (2H, br s), 6.70 (1H, dd, J 6,13 Hz), 6.75–6.80 (1H, m), 7.04 (1H, t, J 9 Hz), 7.45–7.47 (1H, m), 8.81 (1H, d, J 5 Hz), 8.96 (1H, s).

4-(5-Amino-2-fluorophenyl)nicotinonitrile (0.65 g, 3.05 mmol) was treated with 48% hydrobromic acid (25 ml) and the resulting suspension stirred and cooled to 3° C. (internal temperature). A solution of sodium nitrite (0.24 g, 3.5 mmol) in water (1 ml) was then added dropwise over 20 min keeping the internal temperature <5° C. Stirring at <5° C. was continued for 2 h before pouring the reaction into a cooled (5° C.) solution of freshly purified copper(I) bromide (1.53 g, 10.7 mmol) in 48% hydrobromic acid (10 ml). The resulting purple reaction mixture was stirred at 5° C. for 10 min then warmed to 50° C. for 20 min. The reaction was diluted with ice-cold water (50 ml) and extracted with ethyl acetate (2×25 ml). The organic extracts were combined, washed with 5% aqueous sodium sulfite and saturated aqueous ammonium chloride, dried over anhydrous magnesium sulfate, filtered and pre-adsorbed onto silica. Purification by chromatography (silica gel, $CH_2Cl_2$) afforded 4-(5-bromo-2-fluorophenyl)-nicotinonitrile as a white solid: $^1$H NMR (400 MHz, CDCl$_3$) δ 7.17 (1H, t, J 9 Hz), 7.44–7.46 (1H, m), 7.57 (1H, dd, J 6, 2 Hz), 7.61–7.66 (1H, m), 8.87 (1H, d, J 5), 9.00 (1H, d, J 1 Hz).

A mixture of 4-(5-bromo-2-fluorophenyl)nicotinonitrile (0.94 g, 3.4 mmol), potassium acetate (0.67 g, 6.8 mmol) and bis(pinacolato)diboron (0.85 g, 3.8 mmol) was dissolved in 1,4-dioxane containing 1% v/v dimethylsulfoxide (35 ml) and this solution was degassed with nitrogen for 5 min. Dichloro[1,1'-bis(diphenylphosphino)ferrocene] palladium(II) dichloromethane adduct (28 mg, 0.03 mmol) was then added and the mixture was heated at 90° C. for 16 h. After cooling to ambient temperature the reaction was partitioned between ethyl acetate and water. The organic phase was washed with brine, dried over anhydrous magnesium sulfate, filtered and dried under reduced pressure to give 4-fluoro-3-(4-nicotinonitrile)phenylboronic acid as a white solid: $^1$H NMR (400 MHz, DMSO-d6) δ 7.43 (1H, dd, J 8, 10 Hz), 7.72 (1H, d, J 5 Hz), 7.95 (1H, d, J 8 Hz), 8.00–8.04 (1H, m), 8.29 (2H, s), 8.96 (1H, d, J 5 Hz), 9.16 (1H, s).

2-(7-Bromoimidazo[1,2-b][1,2,4]triazin-3-yl)propan-2-ol (150 mg, 0.584 mmol) (from Example 13), sodium carbonate (2 N aqueous solution, 0.93 ml, 1.87 mmol) and 4-fluoro-3-(4-nicotinonitrile)phenylboronic acid (226 mg, 0.93 mmol) in N,N-dimethylacetamide (3 ml) was degassed with nitrogen for 15 min. Tetrakis(triphenylphosphine)palladium(0) (34 mg, 0.05 mmol) was added and the mixture heated at 80° C. for 18 h. The mixture was allowed to cool to ambient temperature, diluted with water (50 ml) and saturated sodium hydrogencarbonate solution (20 ml), then extracted with ethyl acetate (2×75 ml). The combined organic fractions were dried over anhydrous sodium sulfate and evaporated to dryness. The resulting oil was purified by chromatography (silica gel, EtOAc) to give the title compound as a white powder: $^1$H NMR (360 MHz, CDCl$_3$) δ 1.71 (6H, s), 7.42 (1H, t, J 9.8 Hz), 7.57 (1H, d, J 7.2 Hz), 8.14–8.17 (1H, m), 8.24 (1H, d, J 2.2 Hz), 9.80 (1H, s), 8.90 (1H, s), 9.04 (1H, s).

EXAMPLE 25

6,2'-Difluoro-5'-[3-(1-fluoro-1-methylethyl)imidazo[1,2-b][1,2,4]triazin-7-yl]biphenyl-2-carbonitrile This was prepared in 85% yield by a similar procedure to that described in Example 3, step f, except using 6,2'-difluoro-5'-(4,4,5,5-tetramethyl-[1,3,2]dioxaborolan-2-yl)biphenyl-2-carbonitrile instead of 3-[2-fluoro-5-(4,4,5,5-tetramethyl-[1,3,2]dioxaborolan-2-yl)phenyl]pyridine: mp 187–188° C. (CH$_2$Cl$_2$-EtOAc-isohexane); $^1$H NMR (360 MHz, CDCl$_3$) δ 1.84 (6H, d, J 22.1 Hz), 7.40 (1H, t, J 9.3 Hz), 7.48 (1H, td, J 8.6, 1.2 Hz), 7.56 (1H, td, J 7.8, 5.1 Hz), 7.65 (1H, dd, J 7.8, 0.9 Hz), 8.15–8.20 (2H, m), 8.31 (1H, s), 8.80 (1H, d, J 1.2 Hz); MS (ES$^+$) m/z 394 [M+H]$^+$.

EXAMPLE 26

7-[3-(3,5-Difluoropyridin-2-yl)-4-fluorophenyl]-3-(1-fluoro-1-methylethyl)-imidazo[1,2-b][1,2,4]triazine To 4-fluoro-3-(3,5-difluoropyridin-2-yl)phenylboronic acid (0.08 g) and 7-bromo-3-(1-fluoro-1-methylethyl)imidazo[1,2-b][1,2,4]triazine (0.06 g, 0.23 mmol) was added dry potassium phosphate (0.3 g), dichloro[1,1'-bis(diphenylphosphino)ferrocene]palladium(II) dichloromethane adduct (0.04 g) and dry N,N-dimethylformamide (3 ml). The mixture was degassed, then stirred for 24 h at 80° C. under an atmosphere of dry nitrogen. The reaction was cooled to ambient temperature, and the solvent was stripped at reduced pressure. The residue was boiled with toluene (25 ml), and filtered hot. The filtrate was evaporated and the residue subjected to preparative thin layer chromatography (silica gel; 2.5% MeOH/CH$_2$Cl$_2$). The recovered product was crystallised from hot toluene/isohexane to afford the title compound as a yellow solid: $^1$H NMR (400 MHz, DMSO-d$_6$) δ 1.80 (6H, d, J 22.1 Hz), 7.60 (1H, dd, J 8.8, 9.8 Hz), 8.18 (1H, m), 8.32 (1H, m), 8.37 (1H, m), 8.59 (1H, s), 8.74 (1H, d, J 2.3 Hz), 9.03 (1H, s); MS (ES$^+$) m/z 388 [M+H]$^+$.

EXAMPLE 27

4,6,2'-Trifluoro-5'-[3-(1-fluoro-1-methylethyl)imidazo[1,2-b][1,2,4]triazin-7-yl]biphenyl-2-carbonitrile a) 2-Amino-3,5-difluorobenzonitrile A mixture of 2,3,5-trifluorobenzonitrile (25.0 g, 159 mmol) and ethanol (300 ml) pre-saturated with ammonia gas was heated at 120° C. in an autoclave for 8 h. The mixture was allowed to cool to ambient temperature and evaporated to dryness. The residue was partitioned between water (1 l) and ethyl acetate (1 l). The organic layer was dried over anhydrous magnesium sulfate, filtered and evaporated. The residue was purified by flash chromatography (silica gel, CH$_2$Cl$_2$) to afford 3.7 g (15%) of the title compound as a cream solid: $^1$H NMR (360 MHz, CDCl$_3$) δ 4.08 (2H, s), 6.60–6.64 (1H, m), 6.67–6.72 (1H, m).

b) 2-Bromo-3,5-difluorobenzonitrile

This was prepared in 77% yield by a similar procedure to that described in Example 4, but using 2-amino-3,5-difluorobenzonitrile instead of 5'-amino-4,2'-difluorobiphenyl-2-carbonitrile to afford a pale white solid: $^1$H NMR (360 MHz, CDCl$_3$) δ 7.17 (1H, td, J 8.1, 2.8 Hz), 7.28 (1H, ddd, J 7.4, 2.8, 1.6 Hz).

c) 4,6,2'-Trifluoro-5'-nitrobiphenyl-2-carbonitrile

This was prepared in 79% yield by a similar procedure to that described in Example 9, step a, but using 2-bromo-3,5-difluorobenzonitrile instead of 2-chloronicotinonitrile to give, after flash chromatography (silica gel, 10% EtOAc/isohexane then 30% CH$_2$Cl$_2$/isohexane), a solid: $^1$H NMR (360 MHz, CDCl$_3$) δ 7.27 (1H, m), 7.39–7.45 (2H, m), 8.36 (1H, dd, J 6.0, 2.8 Hz), 8.43 (1H, ddd, J 9.0, 4.3, 2.8 Hz).

d) 5'-Amino-4,6,2'-trifluorobiphenyl-2-carbonitrile

This was prepared in 74% yield by a similar procedure to that described in Example 21, step b, but using 4,6,2'-trifluoro-5'-nitrobiphenyl-2-carbonitrile instead of 2-fluoro-2'-methylthio-5-nitrobiphenyl to afford an off-white solid: $^1$H NMR (360 MHz, CDCl$_3$) δ 3.67 (2H, s), 6.64 (1H, dd, J 5.6, 2.8 Hz), 6.76 (1H, ddd, J 8.7, 4.1, 3.0 Hz), 7.02 (1H, t, J 9.0 Hz), 7.17 (1H, td, J 8.6, 2.5 Hz), 7.32 (1H, ddd, J 7.6, 2.5, 1.4 Hz).

e) 5'-Bromo-4,6,2'-trifluorobiphenyl-2-carbonitrile

This was prepared in 52% yield by a similar procedure to that described in Example 4, but using 5'-amino-4,6,2'-trifluorobiphenyl-2-carbonitrile instead of 5'-amino-4,2'-difluorobiphenyl-2-carbonitrile to furnish a yellow solid: $^1$H NMR (360 MHz, CDCl$_3$) δ 7.14 (1H, t, J 9.0 Hz), 7.21 (1H, ddd, J 9.0, 8.3, 2.5 Hz), 7.35 (1H, ddd, J 7.5, 2.5, 1.4 Hz), 7.51 (1H, dd, J 6.3, 2.5 Hz), 7.61 (1H, ddd, J 8.9, 4.6, 2.5 Hz).

f) 5'-(5,5-Dimethyl-[1,3,2]dioxaborinan-2-yl)-4,6,2'-trifluorobiphenyl-2-carbonitrile This was prepared in 73% yield by a similar procedure to that described in Example 4, but using 5'-bromo-4,6,2'-trifluorobiphenyl-2-carbonitrile instead of 5'-bromo-4,2'- difluorobiphenyl-2-carbonitrile, to give a brown solid: $^1$H NMR (360 MHz, CDCl$_3$) δ 1.03 (6H, s), 3.76 (4H, s), 7.15–7.22 (2H, m), 7.32 (1H, ddd, J 7.6, 2.5, 1.5 Hz), 7.81 (1H, dd, J 7.7, 1.5 Hz), 7.85 (1H, ddd, J 8.4, 5.6, 1.4 Hz).
g) 4,6,2'-Trifluoro-5'-[3-(1-fluoro-1-methylethyl)imidazo[1,2-b][1,2,4]triazin-7-yl]biphenyl-2-carbonitrile This was prepared in 4% yield by a similar procedure to that described in Example 3, step f, except using 5'-(5,5-dimethyl-[1,3,2]dioxaborinan-2-yl)-4,6,2'-trifluorobiphenyl-2-carbonitrile instead of 3-[2-fluoro-5-(4,4,5,5-tetramethyl-[1,3,2]dioxaborolan-2-yl)phenyl]pyridine to afford a yellow solid: $^1$H NMR (400 MHz, CDCl$_3$) δ 1.84 (6H, d, J 22.1 Hz), 7.23–7.28 (1H, m), 7.38–7.43 (2H, m), 8.14–8.19 (2H, m), 8.37 (1H, m), 8.30 (1H, s), 8.80 (1H, d, J 1.2 Hz); MS (ES$^+$) m/z 412 [M+H]$^+$.

EXAMPLE 28

2-{7-[4-Fluoro-3-(3-fluoropyridin-2-yl)phenyl] imidazo[1,2-b][1,2,4 triazin-3-yl}propan-2-ol To 2-bromo-3-fluoropyridine (1.198 g, 6.807 mmol), prepared according to the procedure of Queguiner et al. (*Tetrahedron*, 1983, 39, 2009–21), and 2-(2-fluoro-5-nitrophenyl)-4,4,5,5-tetramethyl-[1,3,2]dioxaborolane (2.72 g, 10.2 mmol), in dry tetrahydrofuran (20 ml) under an atmosphere of nitrogen, was added potassium fluoride (2.0 g), water (1.0 ml) and tris(dibenzylideneacetone) dipalladium(0) (0.139 g). The mixture was thoroughly degassed, then a solution of tri-tert-butylphosphine (3.05 ml of a 0.1 M solution in 1,4-dioxane) was added. The mixture was stirred at 35° C. for 18 h. The reaction was partitioned between dichloromethane and water, the organic phase separated, evaporated, and the residue chromatographed (silica gel; CH$_2$Cl$_2$) to afford 3-fluoro-2-(2-fluoro-5-nitrophenyl)pyridine as a white solid (1.485 g): MS (ES$^+$) m/z 236 M+H]$^+$.

3-Fluoro-2-(2-fluoro-5-nitrophenyl)pyridine (1.0 g) was dissolved in dichloromethane (25 ml) and diluted with ethanol (50 ml). Platinum oxide (0.1 g) was added, and the mixture shaken on a Parr hydrogenation apparatus under an atmosphere of hydrogen at 45 psi for 4 h. The reaction was filtered and the filtrate evaporated, to afford 4-fluoro-3-(3-fluoropyridin-2-yl)phenylamine, which was used without further purification: $^{19}$F NMR (400 MHz, CDCl$_3$) δ 128.48 (1F, d, J 36 Hz), 122.66 (1F, d, J 36 Hz).

4-Fluoro-3-(3-fluoropyridin-2-yl)phenylamine was subjected to reaction with sodium nitrite, in hydrobromic acid in the presence of copper(I) bromide, according to the method of Example 23. 2-(5-Bromo-2-fluorophenyl)-3-fluoropyridine was obtained by chromatography (silica gel, CH$_2$Cl$_2$) as a pink solid: MS (ES$^+$) m/z 270, 272 [M+H]$^+$.

2-(5-Bromo-2-fluorophenyl)-3-fluoropyridine was then transformed into 4-fluoro-3-(3-fluoropyridin-2-yl) phenylboronic acid by the method of Example 23: $^1$H NMR (400 MHz, DMSO-d$_6$) δ 8.58 (1H, m), 8.19 (2H, s), 8.04 (1H, dd, J 1.8, 8 Hz), 7.95 (1H, m), 7.86 (1H, m), 7.57 (1H, m), 7.31 (1H, dd, J 8.2, 10.6 Hz).

4-Fluoro-3-(3-fluoropyridin-2-yl)phenylboronic acid (50 mg, 0.21 mmol) was coupled to 2-(7-bromoimidazo[1,2-b][1,2,4]triazin-3-yl)propan-2-ol (52 mg, 0.20 mmol) using the method of Example 20. Purification by chromatography (silica gel, 3% MeOH(CH$_2$Cl$_2$) gave the title compound as a yellow solid: $^1$H NMR (400 MHz, CDCl$_3$) δ 1.71 (6H, s), 3.34 (1H, s), 7.34 (1H, t, J 9 Hz), 7.39–7.43 (1H, m), 7.54–7.59 (1H, m), 8.13–8.17 (1H, m), 8.27 (1H, s), 8.30 (1H, dd, J 7, 2 Hz), 8.58–8.61 (1H, m), 8.77 (1H, s); MS (ES$^+$) m/z 368 [M+H]$^+$.

EXAMPLE 29

2-{7-[4-Fluoro-3-(5-fluoropyridin-2-yl)phenyl] imidazo[1,2-b][1,2,4]triazin-3-yl}propan-2-ol This compound was made in the same way as described for Example 28, substituting 2-bromo-5-fluoropyridine for 2-bromo-3-fluoropyridine in the first step, to give the title compound as a yellow solid: mp 222° C.; $^1$H NMR (360 MHz, CDCl$_3$) δ 1.72 (6H, s), 3.33 (1H, br s), 7.29–7.55 (2H, m), 7.86–7.81 (2H, m), 8.29 (1H, s), 8.62–8.65 (2H, m), 8.78 (1H, s); MS (ES$^+$) m/z 368 [M+H]$^+$. Anal. Found: C, 61.98; H, 4.15; N, 18.71%. Required for C$_{19}$H$_{15}$F$_2$N$_5$O: C, 62.12; H, 4.12; N, 19.06%.

EXAMPLE 30

2-[7-(4-Fluoro-3-(pyridin-2-yl)phenyl)imidazo[1,2-b][1,2,4]triazin-3-yl]-propan-2-ol 4-Fluoro-3-(pyridin-2-yl)phenylboronic acid (38 mg, 0.18 mmol) was coupled to 2-(3-bromoimidazo[1,2-b][1,2,4]triazin-7-yl)propan-2-ol (43 mg, 0.17 mmol) using the method described in Example 20. Purification by chromatography (silica gel, 3% MeOH/CH$_2$Cl$_2$) gave the title compound as a yellow solid: $^1$H NMR (400 MHz, CDCl$_3$) δ 1.71 (6H, s), 3.33 (1H, s), 7.30–7.35 (2H, m), 7.80 (1H, td, J 8, 2 Hz), 7.85–7.89 (1H, m), 8.07–8.11 (1H, m), 8.30 (1H, s), 8.66 (1H, dd, J 7, 2 Hz), 8.76–8.79 (2H, m); MS (ES$^+$) m/z 350 [M+H]$^+$.

EXAMPLE 31

2-[7-(4-Fluoro-3-(pyridazin-3-yl)phenyl)imidazo[1,2-b][1,2,4]triazin-3-yl]-propan-2-ol A degassed solution of 3-chloropyridazine (1.96 g, 17 mmol) (prepared according to Wermuth et al. in *J. Med. Chem.*, 1997, 30, 239–249) and 2-(2-fluoro-5-nitrophenyl)-4,4,5,5-tetramethyl-[1,3,2]dioxaborolane (6.86 g, 25 mmol) was formed in 1,4-dioxane (20 ml). Potassium phosphate (16 g, 76 mmol) and dichloro[1,1'-bis(diphenylphosphino) ferrocene]palladium(II) dichloromethane adduct (700 mg, 0.9 mmol) were added and the mixture stirred at 50° C. for 72 h. The reaction mixture was adsorbed onto silica gel and purified by chromatography over silica gel using ethyl acetate as eluent. Further purification by chromatography (silica gel, CH$_2$Cl$_2$), then crystallisation from toluene/ isohexane, gave 3-(2-fluoro-5-nitrophenyl)pyridazine as a white solid: $^1$H NMR (400 MHz, CDCl$_3$) δ 9.27 (1H, dd, J 5, 2 Hz), 9.18 (1H, dd, J 7, 3 Hz), 8.36–8.41 (1H, m), 8.00–8.04 (1H, m), 7.63 (1H, dd, J 9, 5 Hz), 7.39 (1H, dd, J 10, 9 Hz).

3-(2-Fluoro-5-nitrophenyl)pyridazine (348 mg, 1.6 mmol) was reduced by the method of Example 20 over 8 h to give 4-fluoro-3-(pyridazin-3-yl)phenylamine as an oil: MS (ES$^+$) m/z 301 [M+H]$^+$.

4-Fluoro-3-(pyridazin-3-yl)phenylamine (226 mg, 1.2 mmol) was bromo-deaminated by the method of Example 20 to give 3-(5-bromo-2-fluorophenyl)pyridazine as an off-white solid: $^1$H NMR (400 MHz, CDCl$_3$) δ 9.20 (1H, dd, J 1, 5 Hz), 8.37 (1H, dd, J 3, 7 Hz), 7.94–7.98 (1H, m), 7.54–7.60 (2H, m), 7.11 (1H, dd, J 9, 11 Hz).

3-(5-Bromo-2-fluorophenyl)pyridazine (304 mg, 1.20 mmol) was reacted with bis(neopentyl glycolato)diboron (298 mg, 1.32 mmol) using the method of Example 20 to give 4-fluoro-3-(pyridazin-3-yl)phenylboronic acid as a white solid: MS (ES$^+$) m/z 219 [M+H]$^+$.

4-Fluoro-3-(pyridazin-3-yl)phenylboronic acid (50 mg, 0.23 mmol) was coupled to 2-(7-bromoimidazo[1,2-b][1,2, 4]triazin-3-yl)propan-2-ol (56 mg, 0.22 mmol) using the method of Example 20. Purification by chromatography (silica gel, 3% MeOH/CH$_2$Cl$_2$) gave the title compound as a yellow solid: $^1$H NMR (400 MHz, CDCl$_3$) δ 1.72 (6H, s), 7.37 (1H, dd, J 11, 9 Hz), 7.60 (1H, dd, J 9, 5 Hz), 8.04 (1H, dt, J 9, 2 Hz), 8.14–8.19 (1H, m), 8.31 (1H, s), 8.82 (1H, s), 8.90 (1H, dd, J 7, 2 Hz), 9.22 (1H, dd, J 5, 2 Hz); MS (ES$^+$) m/z 351 [M+H]$^+$.

EXAMPLE 32

2-[7-(4-Fluoro-3-(pyrimidin-4-yl)phenyl)imidazo[1,2-b][1,2,4]triazin-3-yl]-propan-2-ol 2,4-Dichloropyrimidine (2.0 g, 13 mmol) was coupled to 2-(2-fluoro-5-nitrophenyl)-4,4,5,5-tetramethyl-[1,3,2]dioxaborolane (3.9 g, 15 mmol) using the method of Example 20. Purification by chromatography (silica gel, 20% isohexane/CH$_2$Cl$_2$) gave 2-chloro-4-(2-fluoro-5-nitrophenyl)-pyrimidine as a white solid: $^1$H NMR (400 MHz, CDCl$_3$) δ 7.40 (1H, dd, J 10, 9 Hz), 7.85 (1H, dd, J 5, 2 Hz), 8.38–8.43 (1H, m), 8.77 (1H, d, J 6), 9.16 (1H, q, J 3 Hz).

A solution of 2-chloro-4-(2-fluoro-5-nitrophenyl)pyrimidine (800 mg, 3.2 mmol) in ethanol (300 ml) was reduced under 40 psi hydrogen with platinum(IV) oxide (100 mg) for 30 minutes then filtered to give a solution of 3-(2-chloropyrimidin-4-yl)-4-fluorophenylamine: MS (ES$^+$) m/z 224 [M+H]$^+$.

To the solution of 3-(2-chloropyrimidin-4-yl)-4-fluorophenylamine from above was added triethylamine (0.48 ml, 3.15 mmol) and palladium on active carbon (100 mg, 10% palladium) and the mixture was reduced under 40 psi hydrogen for 30 minutes. The mixture was filtered and the solvent removed to give 4-fluoro-3-(pyrimidin-4-yl)phenylamine as a yellow solid: MS (ES$^+$) m/z 190 [M+H]$^+$.

4-Fluoro-3-(pyrimidin-4-yl)phenylamine (1.0 g, 5.3 mmol) was bromo-deaminated using the method of Example 20 to give 4-(5-bromo-2-fluorophenyl)pyrimidine as a white solid: $^1$H NMR (400 MHz, CDCl$_3$) δ 7.10 (1H, dd, J 11, 9 Hz), 7.56–7.60 (1H, m), 7.83–7.85 (1H, m), 8.36 (1H, dd, J 7, 3 Hz), 8.81 (1H, d, J 6 Hz), 9.32 (1H, d, J 1 Hz).

4-(5-Bromo-2-fluorophenyl)pyrimidine (503 mg, 2.0 mmol) was reacted with bis(neopentyl glycolato)diboron (494 mg, 2.2 mmol) using the method of Example 20 to give 4-fluoro-3-(pyrimidin-4-yl)phenylboronic acid as a tan solid: MS (ES$^+$) m/z 219 [M+H]$^+$.

4-Fluoro-3-(pyrimidin-4-yl)phenylboronic acid (50 mg, 0.23 mmol) was coupled to 2-(7-bromoimidazo[1,2-b][1,2,4]triazin-3-yl)propan-2-ol (56 mg, 0.22 mmol) using the method of Example 20. Purification by chromatography (silica gel, 3% MeOH/CH$_2$Cl$_2$) then recrystallisation from hot toluene gave the title compound as a yellow solid: $^1$H NMR (400 MHz, DMSO-d$_6$) δ 1.57 (6H, s), 5.77 (1H, s), 7.62 (1H, dd, J 11, 9 Hz), 7.98–8.01 (1H, m), 8.28–8.33 (1H, m), 8.49 (1H, s), 8.80 (1H, dd, J 7, 2 Hz), 8.97 (1H, d, J 5 Hz), 9.05 (1H, s), 9.38 (1H, d, J 1 Hz); MS (ES$^+$) m/z 351 [M+H]$^+$.

EXAMPLE 33

2-[7-(4-Fluoro-3-(pyridazin-4-yl)phenyl)imidazo[1,2-b][1,2,4]triazin-3-yl]-propan-2-ol To a solution of 3-bromo-4-fluoronitrobenzene (2 g, 9.1 mmol) in tetrahydrofuran (30 ml) was added triethylamine (1.9 ml, 13.6 mmol), trimethylsilylacetylene (1.9 ml, 13.6 mmol), triphenylphosphine (60 mg, 0.23 mmol) and dichlorobis(triphenylphosphine)palladium(II) (319 mg, 0.46 mmol). After stirring at room temperature for 20 minutes copper(I) iodide (17 mg, 0.09 mmol) was added and the mixture left to stir for 18 h at room temperature. The reaction mixture was quenched into isohexane (150 ml) and filtered through a plug of silica using isohexane as eluent. The solvent was removed in vacuo to leave (2-fluoro-5-nitrophenylethynyl)trimethylsilane as a brown solid: $^1$H NMR (360 MHz, CDCl$_3$) δ 0.10 (9H, s), 7.02 (1H, dd, J 8, 1 Hz), 7.97–8.02 (1H, m), 8.17 (1H, dd, J 6, 3 Hz).

A solution of 1,2,4,5-tetrazine (0.53 M in dichloromethane) was prepared by the method of H. C. van der Plas et al. (*J. Heterocycl. Chem.*, 1987, 24, 545–548). (2-Fluoro-5-nitrophenylethynyl)trimethylsilane (8.8 g, 37.1 mmol) and 1,4-dioxane were added to a solution of 1,2,4,5-tetrazine (35 ml, 18.6 mmol, 0.53 M in dichloromethane). The dichloromethane was distilled off and the dioxane solution was stirred at reflux for 36 h. The solvent was removed to leave a brown oil. Purification by chromatography (silica gel, 0–1% MeOH/CH$_2$Cl$_2$) gave 4-(2-fluoro-5-nitrophenyl)-5-trimethylsilanylpyridazine as a brown oil: MS (ES$^+$) m/z 292 [M+H]$^+$ and 249 [M–3CH$_2$]$^+$.

A solution of 4(2-fluoro-5-nitrophenyl)-5-trimethylsilanylpyridazine (5.25 g, 18.0 mmol) was formed in N,N-dimethylformamide (50 ml) with water (1 ml). Potassium fluoride (2.10 g, 36.1 mmol) was added and the mixture stirred at room temperature for 18 h. The reaction mixture was added to ethyl acetate (100 ml) and washed with water (4×100 ml) then brine (50 ml). The organic phase was dried over magnesium sulphate, filtered and the solvent removed to leave an orange brown solid. Purification by chromatography (silica gel, 50% EtOAc/isohexane) then recrystallisation from dichloromethane with isohexane gave 4-(2-fluoro-5-nitrophenyl)pyridazine as light brown crystals: $^1$H NMR (360 MHz, CDCl$_3$) δ 7.45 (1H, t, J 9 Hz), 7.70–7.74 (1H, m), 8.38–8.43 (1H, m), 8.49 (1H, dd, J 6, 3 Hz), 9.37 (1H, dd, J 5, 1 Hz), 9.46–9.48 (1H, m).

4-(2-Fluoro-5-nitrophenyl)pyridazine (1.67 g, 7.62 mmol) was reduced using the method of Example 20 to give 4-fluoro-3-(pyridazin-4-yl)phenylamine as an orange solid: MS (ES$^+$) m/z 190 [M+H]$^+$.

4-Fluoro-3-(pyridazin-4-yl)phenylamine (500 mg, 2.64 mmol) was bromo-deaminated using the method of Example 20 to give 4-(5-bromo-2-fluorophenyl)pyridazine as a white solid: $^1$H NMR (360 MHz, CDCl$_3$) δ 7.16 (1H, dd, J 9, 1 Hz), 7.57–7.62 (1H, m), 7.63–7.66 (2H, m), 9.29 (1H, dd, J 5, 1 Hz), 9.39–9.41 (1H, m).

4-(5-Bromo-2-fluorophenyl)pyridazine (1.0 g, 3.95 mmol) was reacted with bis(neopentyl glycolato)diboron (982 mg, 4.35 mmol) using the method of Example 20 to give 4-fluoro-3-(pyridazin-4-yl)phenylboronic acid: MS (ES$^+$) m/z 219 [M+H]$^+$.

4-Fluoro-3-(pyridazin-4-yl)phenylboronic acid (300 mg, 1.38 mmol) was coupled to 2-(7-bromoimidazo[1,2-b][1,2,4]triazin-3-yl)propan-2-ol (100 mg, 0.39 mmol) using the method of Example 20. Purification by chromatography (silica gel, 3% MeOH/CH$_2$Cl$_2$) then dissolving in toluene and washing with water followed by recrystallisation from hot toluene with isohexane gave the title compound as a yellow solid: $^1$H NMR (400 MHz, CDCl$_3$) δ 1.73 (6H, s), 3.23 (1H, s), 7.41 (1H, dd, J 10, 9 Hz), 7.75–7.78 (1H, m), 8.08–8.13 (1H, m), 8.28 (1H, s), 8.31 (1H, dd, J 7, 2 Hz), 8.83 (1H, s), 9.32 (1H, dd, J 5, 1 Hz), 9.50–9.52 (1H, m); MS (ES$^+$) m/z 351 [M+H]$^+$.

EXAMPLE 34

4-{2-Fluoro-5-[3-(1-hydroxy-1-methylethyl)imidazo[1,2-b][1,2,4]triazin-7-yl]phenyl}pyrimidine-5-carbonitrile A solution of 4-chloropyrimidine-5-carbonitrile in diethyl ether (8.3 mmol in 250 ml) was formed by the method of H.

Bredereck, *Chem. Ber.,* 1967, 100, 3664–3670. 1,4-Dioxane (50 ml) was added and the diethyl ether was distilled off under reduced pressure. 2-(2-Fluoro-5-nitrophenyl)-4,4,5,5-tetramethyl-[1,3,2]dioxaborolane (2.4 g, 9.1 mmol) and caesium carbonate (5.4 g, 16.6 mmol) were added and the mixture was degassed. Dichloro[1,1'-bis(diphenylphosphino)ferrocene]palladium(II) dichloromethane adduct (50 mg, 0.06 mmol) was added and the mixture stirred at 85° C. for 18 h. The solvent was removed under reduced pressure. Purification by chromatography (silica gel, 50–100% $CH_2Cl_2$/isohexane) then recrystallisation from dichloromethane/isohexane gave 4-(2-fluoro-5-nitrophenyl)pyrimidine-5-carbonitrile as a pink solid: $^1$H NMR (400 MHz, $CDCl_3$) δ 7.49 (1H, t, J 9 Hz), 8.48–8.53 (1H, m), 8.65 (1H, dd, J 6, 3 Hz), 9.16 (1H, s), 9.53 (1H, s).

4-(2-Fluoro-5-nitrophenyl)pyrimidine-5-carbonitrile (250 mg, 1 mmol) was reduced using the method of Example 20 to give 4-(5-amino-2-fluorophenyl)pyrimidine-5-carbonitrile as an orange solid: MS ($ES^+$) m/z 215 $[M+H]^+$.

4-(5-Amino-2-fluorophenyl)pyrimidine-5-carbonitrile (219 mg, 1 mmol) was bromo-deaminated using the method of Example 20 to give 4-(5-bromo-2-fluorophenyl)pyrimidine-5-carbonitrile as a white solid: $^1$H NMR (360 MHz, $CDCl_3$) δ 7.20 (1H, t, J 9 Hz), 7.68–7.73 (1H, m), 7.82 (1H, dd, J 6, 2 Hz), 9.10 (1H, s), 9.47 (1H, s).

4-(5-Bromo-2-fluorophenyl)pyrimidine-5-carbonitrile (150 mg, 0.5 mmol) was reacted with bis(neopentyl glycolato)diboron (134 mg, 0.6 mmol) using the method of Example 20 to give 4-(5-boronic acid-2-fluorophenyl)pyrimidine-5-carboxylic acid amide as a tan solid: MS ($ES^+$) m/z 262 $[M+H]^+$.

4-(5-Boronic acid-2-fluorophenyl)pyrimidine-5-carboxylic acid amide (163 mg, 0.6 mmol) was coupled to 2-(7-bromoimidazo[1,2-b][1,2,4]triazin-3-yl)propan-2-ol (161 mg, 0.6 mmol) using the method of Example 20. Purification by chromatography (silica gel, 10% MeOH/$CH_2Cl_2$) gave 4-{2-fluoro-5-[3-(1-hydroxy-1-methylethyl)imidazo[1,2-b][1,2,4]triazin-7-yl]phenyl}pyrimidine-5-carboxylic acid amide as a yellow solid: $^1$H NMR (400 MHz, DMSO-$d_6$) δ 1.56 (6H, s), 5.77 (1H, s), 7.49 (1H, dd, J 9, 1 Hz), 7.70 (1H, s), 8.19 (1H, s), 8.26–8.30 (1H, m), 8.39 (1H, dd, J 7, 2 Hz), 8.46 (1H, s), 9.02 (1H, s), 9.03 (1H, s), 9.40 (1H, s); MS ($ES^+$) m/z 394 $[M+H]^+$.

A suspension of 4-{2-fluoro-5-[3-(1-hydroxy-1-methylethyl)-imidazo[1,2-b][1,2,4]triazin-7-yl]phenyl}pyrimidine-5-carboxylic acid amide (50 mg, 0.13 mmol) was formed in dry toluene (50 ml). Dibutyltin oxide (6 mg, 0.03 mmol) was added and the mixture heated at reflux for 18 h. The solvent was removed under reduced pressure then purification by chromatography (silica gel, 3% MeOH/$CH_2Cl_2$) gave the title compound as a yellow solid: $^1$H NMR (400 MHz, $CDCl_3$) δ 1.72 (6H, s), 3.23 (1H, s), 7.45 (1H, dd, J 9, 1 Hz), 8.24–8.29 (1H, m), 8.30 (1H, s), 8.42 (1H, dd, J 7, 2 Hz), 8.81 (1H, s), 9.14 (1H, s), 9.51 (1H, s); MS ($ES^+$) m/z 376 $[M+H]^+$.

EXAMPLE 35

2-{7-[3-(3,5-Difluoropyridin-2-yl)phenyl]imidazo[1,2-b][1,2,4]triazin-3-yl}-propan-2-ol A degassed solution of 3-nitrophenylboronic acid (0.47 g, 2.8 mmol) and 3,5-difluoro-2,4,6-tribromopyridine (2 g, 5.7 mmol) was formed in tetrahydrofuran (30 ml) with aqueous sodium carbonate (3 ml, 2 M). Tetrakis(triphenylphosphine)palladium(0) (100 mg, 0.09 mmol) was added and the mixture stirred at 65° C. for 48 hours. The reaction was allowed to cool to room temperature then poured into water (50 ml) and extracted with ethyl acetate (3×30 ml). The organic phases were combined, dried over anhydrous magnesium sulphate, filtered and evaporated to a brown solid. Purification by chromatography (silica gel, 33% $CH_2Cl_2$/isohexane) gave 2,4-dibromo-3,5-difluoro-6-(3-nitrophenyl)pyridine as a white solid: $^1$H NMR (400 MHz, $CDCl_3$) δ 7.70 (1H, t, J 7 Hz), 8.28–8.36 (2H, m), 8.83 (1H, s).

A solution of 2,4-dibromo-3,5-difluoro-6-(3-nitrophenyl)pyridine (190 mg, 0.48 mmol) was formed in ethanol (150 ml). Triethylamine (0.13 ml, 0.97 mmol) and palladium on activated carbon (10%, 80 mg) were added and the mixture reduced under 40 psi hydrogen for 30 minutes. The mixture was then filtered and the solvent removed under reduced pressure to give crude 3-(3,5-difluoropyridin-2-yl)phenylamine as a white solid: MS ($ES^+$) m/z 207 $[M+H]^+$.

3-(3,5-Difluoropyridin-2-yl)phenylamine (126 mg, 0.61 mmol) was bromo-deaminated using the method of Example 20 to give 2-(3-bromophenyl)-3,5-difluoropyridine as a white solid: MS ($ES^+$) m/z 270 and 272 $[M+H]^+$.

2-(3-Bromophenyl)-3,5-difluoropyridine (80 mg, 0.30 mmol) was reacted with bis(neopentyl glycolato)diboron (74 mg, 0.33 mmol) using the method of Example 20 to give 3-(3,5-difluoropyridin-2-yl)phenylboronic acid as a tan solid: MS ($ES^+$) m/z 236 $[M+H]^+$.

3-(3,5-Difluoropyridin-2-yl)phenylboronic acid (25 mg, 0.11 mmol) was coupled to 2-(7-bromoimidazo[1,2-b][1,2,4]triazin-3-yl)propan-2-ol (27 mg, 0.11 mmol) using the method of Example 20. Purification by chromatography (silica gel, 3% MeOH/$CH_2Cl_2$) gave impure product as a yellow solid. The product was then dissolved in hydrochloric acid (2 N, 50 ml), filtered and washed with diethyl ether (2×20 ml). The acid solution was cooled to 0° C. and neutralised with saturated aqueous sodium hydrogencarbonate and extracted with ethyl acetate (3×20 ml). The combined organic phases were dried over anhydrous magnesium sulphate, filtered and evaporated to give the title compound as a yellow solid: $^1$H. NMR (400 MHz, $CDCl_3$) δ 1.72 (6H, s), 3.35 (1H, s), 7.32–7.38 (1H, m), 7.64 (1H, t, J 8 Hz), 7.95–7.98 (1H, m), 8.10–8.13 (1H, m), 8.33 (1H, 8), 8.48 (1H, d, J 3 Hz), 8.60–8.61 (1H, m), 8.79 (1H, s); MS ($ES^+$) m/z 368 $[M+H]^+$.

EXAMPLE 36

7-[3-(1-Methyl-1H-pyrazol-3-yl)phenyl]-3-trifluoromethylimidazo[1,2-b][1,2,4]triazine To a solution of 3-(3-bromophenyl)pyrazole (1.0 g, 4.4 mmol) in DMF (10 ml) at 0° C. was added sodium hydride (240 mg of a 60% dispersion in mineral oil, 7.0 mmol). After stirring for 15 min at 0° C. the mixture was warmed to 25° C. and stirred for a further 15 min. Methyl iodide (0.38 ml, 6.1 mmol) was added and the solution stirred at 25° C. for 3 h. After this time the solvent was removed in vacuo and the residue was partitioned between ethyl acetate (20 ml) and water (20 ml). The organic layer was separated, dried ($MgSO_4$) and evaporated. The residue was chromatographed (silica gel, 5% EtOAc/$CH_2Cl_2$) to give two products. The less polar product was isolated as a colourless oil (0.822 g, 79%) and identified as 3-(3-bromophenyl)-1-methyl-1H-pyrazole: $^1$H NMR (360 MHz, $CDCl_3$) δ 3.95 (3H, s), 6.52 (1H, d, J 2.2 Hz), 7.25 (1H, t, J 7.9 Hz), 7.37–7.42 (2H, m), 7.70. (1H, d, J 7.7 Hz), 7.95 (1H, t, J 1.7 Hz); MS ($ES^+$) m/z 237/239 $[M+H]^+$. The more polar isomer was isolated as a colourless oil (0.172 g, 16%) and identified as 5-(3-bromophenyl)-1-methyl-1N-pyrazole: $^1$H NMR (360 MHz, CDCl$_3$) δ 3.89 (3H, s), 6.31 (1H, d, J 1.9 Hz), 7.32–7.35 (2H, m), 7.51–7.58 (3H, m); MS (ES$^+$) m/z 237/239 [M+H]$^+$.

A mixture of 3-(3-bromophenyl)-1-methyl-1H-pyrazole (403 mg, 1.7 mmol), bis(neopentyl glycolato)diboron (0.4 g, 1.78 mmol) and potassium acetate (0.5 g, 5.1 mmol) in 1,4-dioxane (20 ml) was degassed with nitrogen for 15 min. After this time [1,1'-bis(diphenylphosphino)-ferrocene] dichloropalladium(II) (69 mg, 0.085 mmol) was added and the mixture was heated at reflux for 18 h. The solvent was evaporated in vacuo and the resultant 3-[3-(5,5-dimethyl-[1,3,2]dioxaborinan-2-yl)phenyl]-1-methyl-1H-pyrazole was used without further purification.

A mixture of 3-[3-(5,5-dimethyl-[1,3,2]dioxaborinan-2-yl)phenyl]-1-methyl-1H-pyrazole (from above), 7-bromo-3-trifluoromethylimidazo[1,2-b][1,2,4]triazine (300 mg, 1.1 mmol) and sodium carbonate (1.7 ml of a 2 N solution, 3.4 ml) in THF (7 ml) was degassed with nitrogen for 15 min. After this time tetrakis(triphenylphosphine)palladium(0) (130 mg, 0.11 mmol) was added and the mixture heated at reflux for 18 h. The solvent was evaporated in vacuo and the residue partitioned between ethyl acetate (30 ml) and 1 N NaOH (2×30 ml). The organic phase was separated and washed with brine (30 ml), dried (MgSO$_4$) and evaporated. The residue was chromatographed (silica gel, 2.5% MeOH/CH$_2$Cl$_2$) and the fractions containing the desired product were combined and evaporated. The residue was triturated with diethyl ether twice to afford the title compound (140 mg, 36%) as a colourless solid: $^1$H NMR (400 MHz, CDCl$_3$) δ 3.99 (3H, s), 6.62 (1H, d, J 2.2 Hz), 7.43 (1H, d, J 2.2 Hz), 7.58 (1H, t, J 7.8 Hz), 7.89 (1H, dd, J 7.8, 1.2 Hz), 8.03 (1H, d, J 7.9 Hz), 8.51 (1H, t, J 1.5 Hz), 8.68 (1H, s), 8.80 (1H, s); MS (ES$^+$) m/z 345 [M+H]$^+$.

EXAMPLE 37

7-[4-Chloro-3-(pyridin-3-yl)phenyl]-3-trifluoromethylimidazo[1,2-b][1,2,4]-triazine a) 3-(2-Chloro-5-nitrophenyl)pyridine A mixture of 3-bromo-4-chloronitrobenzene (5.17 g, 21.9 mmol) and pyridine-3-boronic acid 1,3-propanediol cyclic ester (4.27 g, 26.2 mmol) in ethanol (30 ml) and toluene (30 ml) together with 2 N Na$_2$CO$_3$ solution (13.9 ml) was degassed with a stream of nitrogen for 10 min. Tetrakis(triphenylphosphine)palladium(0) (0.3 g, 0.26 mmol) was added and the reaction was heated at reflux for over 24 h. The mixture was concentrated under reduced pressure to remove the organic solvents and water (100 ml) was added. This was extracted with ethyl acetate (200 ml) and then washed with brine (75 ml), dried (MgSO$_4$), and concentrated under reduced pressure while dry loading onto silica. The resulting crude residue was purified by column chromatography (silica gel, 50% Et$_2$O/CH$_2$Cl$_2$), to yield the title compound (3.53 g, 69%): $^1$H NMR (360 MHz, CDCl$_3$) δ 7.42–7.48 (1H, m), 7.70 (1H, d, J 8.7 Hz), 7.81 (1H, dt, J 8.0, 1.8 Hz), 8.17–8.27 (2H, m), 8.68–8.77 (2H, m).

b) 4-Chloro-3-(pyridin-3-yl)aniline

Tin(II) chloride (11.87 g, 62.6 mmol) was added portionwise over 5 min to a stirred mixture of 3-(2-chloro-5-nitrophenyl)pyridine (3.53 g, 15.1 mmol) in ethanol (100 ml) and 1,4-dioxane (100 ml) at 0° C. The mixture was then stirred overnight, gradually warming to room temperature, and then concentrated under reduced pressure. 20% Aqueous ammonia solution (200 ml) and ethanol (300 ml) were added and again the mixture concentrated under reduced pressure. Ethyl acetate (300 ml) was added and the mixture heated to reflux, the solids were filtered off and the process repeated twice more. The combined organic filtrates were concentrated under reduced pressure to yield the title compound (2.69 g, 87%): $^1$H NMR (360 MHz, CDCl$_3$) δ 6.65–6.70 (2H, m), 7.26 (1H, dt, J 8.5, 1.1 Hz), 7.33 (1H, dd, J 7.8, 4.8 Hz), 7.77 (1H, dt, J 7.8, 1.9 Hz), 8.59 (1H, dd, J 4.8, 1.6 Hz), 8.66 (1H, d, J 1.8 Hz); MS (ES$^+$) m/z 205, 207 (3:1) [M+H]$^+$.

c) 3-(5-Bromo-2-chlorophenyl)pyridine tert-Butyl nitrite (3.9 ml, 32.9 mmol) was added dropwise to a stirred mixture of 4-chloro-3-(pyridin-3-yl)aniline (2.69 g, 13.2 mmol) and copper(II) bromide (3.23 g, 14.5 mmol) in acetonitrile (150 ml) and dichloromethane (30 ml) at −10° C. Upon complete addition the reaction was warmed to room temperature and stirred overnight. The mixture was concentrated under reduced pressure while dry loading onto silica and the resulting crude residue was purified by column chromatography (silica gel, CH$_2$Cl$_2$). The combined fractions were washed with 10% aqueous ammonia solution (2×100 ml), water (100 ml) and brine (100 ml), dried (MgSO$_4$) and concentrated to yield the title compound (1.60 g, 45%): $^1$H NMR (360 MHz, CDCl$_3$) δ 7.30–7.50 (4H, m), 7.77 (1H, dt, J 7.9, 1.9 Hz), 8.60–8.70 (2H, m); MS (ES$^+$) m/z 268, 270 (1:1) [M]$^+$.

d) 3-[2-Chloro-5-(5,5-dimethyl-[1,3,2]dioxaborinan-2-yl)phenyl]pyridine

A mixture of 3-(5-bromo-2-chlorophenyl)pyridine (0.60 g, 2.3 mmol), bis(neopentyl glycolato)diboron (0.56 g, 2.5 mmol), potassium acetate (1.03 g, 10.5 mmol) and [1,1'-bis(diphenylphosphino)ferrocene]-dichloropalladium(II) (143 mg, 5 mol %) in 1,4-dioxane (30 ml) was degassed with a stream of nitrogen for 10 min and then heated at 110° C. for 16 h. The reaction mixture was concentrated under reduced pressure and water (100 ml) was added. This was extracted with diethyl ether (2×75 ml). The combined ethereal extracts were extracted with 4 N NaOH (3×50 ml). These combined basic extracts were neutralised with concentrated hydrochloric acid and then back-extracted with dichloromethane (3×100 ml). The combined organic filtrates were washed with brine (50 ml) and dried (MgSO$_4$) to give the title compound (830 mg, 99%): $^1$H NMR (400 MHz, CDCl$_3$) δ 1.02 (6H, s), 3.79 (4H, s), 7.30–7.43 (2H, m), 7.48 (1H, d, J 7.8 Hz), 7.70–7.87 (2H, m), 8.56–8.63 (1H, m), 8.69 (1H, d, J 1.8 Hz); MS (ES$^+$) m/z 302, 304 (3:1) [M+H]$^+$.

e) 7-[4-Chloro-3-(pyridin-3-yl)phenyl]-3-trifluoromethylimidazo[1,2-b][1,2,4]triazine A mixture of 7-bromo-3-trifluoromethylimidazo[1,2-b][1,2,4]triazine (0.05 g, 0.19 mmol), 3-[2-chloro-5-(5,5-dimethyl-[1,3,2]dioxaborinan-2-yl)phenyl]pyridine (84 mg, 0.28 mmol) and 2 M Na$_2$CO$_3$ (0.28 ml) in 1,2-dimethoxyethane (2 ml) was degassed for 10 min with a stream of nitrogen. Tetrakis(triphenylphosphine)palladium (0) (0.011 g) was added and the mixture was stirred under nitrogen at 80° C. for 12 h. After allowing to cool to ambient temperature, the mixture was diluted with ethyl acetate then partitioned between water (100 ml) and ethyl acetate (100 ml). The organic extracts were dried (MgSO$_4$) and evaporated in vacuo. The residue was purified by flash chromatography (silica gel, 3% MeOH/CH$_2$Cl$_2$), to give 75 mg (61%) of the title compound: $^1$H NMR (400 MHz, CDCl$_3$) δ 7.42–7.45 (1H, m), 7.71 (1H, d, J 8.6 Hz), 7.86–7.89 (1H, m), 8.08 (1H, dd, J 8.6, 2.5 Hz), 8.14 (1H, d, J 2.5 Hz), 8.64 (1H, s), 8.70 (1H, dd, J 4.9, 2.3 Hz), 8.68 (1H, s), 8.82 (1H, dd, J 2.3, 1.0 Hz); MS (ES$^+$) m/z 376.

EXAMPLE 38

7-[3-(Pyridin-3-yl)-phenyl]-3-trifluoromethylimidazo[1,2-b][1,2,4]triazine a) 3-(3-Bromophenyl)pyridine This reaction was carried out as described in Example 37, step a, using 1,3-dibromobenzene (8.7 g, 36.8 mmol) and pyridine-3-boronic acid 1,3-propanediol cyclic ester (4.0 g, 24.5 mmol) in ethanol (60 ml) for 14 h. The resulting crude residue was purified by column chromatography (silica gel, 80% Et$_2$O/hexane) to yield the title compound (3.66 g, 64%): $^1$H NMR (360 MHz, CDCl$_3$) δ 7.30–7.42 (2H, m), 7.47–7.60 (2H, m), 7.72 (1H, s), 7.84 (1H, dt, J 8.0, 2.0 Hz), 8.62 (1H, dd, J 4.8, 1.5 Hz), 8.83 (1H, s).

b) 3-[3-(5,5-Dimethyl-[1,3,2]dioxaborinan-2-yl)phenyl]pyridine

This reaction was carried out as described in Example 37, step d, using 3-(3-bromophenyl)pyridine (1.65 g, 7.1 mmol), bis(neopentyl glycolato)diboron (1.75 g, 7.8 mmol), potassium acetate (2.1 g, 21.2 mmol) and [1,1'-bis(diphenylphosphino)ferrocene]dichloropalladium(II) (288 mg, 5 mol %) in 1,4-dioxane (60 ml) to yield the title compound (1.63 mg, 87%): $^1$H NMR (360 MHz, CDCl$_3$) δ 1.04 (6H, s), 3.80 (4H, s), 7.38 (1H, dd, J 7.8, 4.9 Hz), 7.47 (1H, t, J 7.8 Hz), 7.60–7.68 (1H, m), 7.84 (1H, d, J 7.4 Hz), 7.96 (1H, dt, J 7.8, 2.0 Hz), 8.03 (1H, s), 8.58 (1H, dd, J 4.9, 1.5 Hz), 8.85 (1H, s); MS (ES$^+$) m/z 267 [M+H]$^+$.

c) 7-[3-(Pyridin-3-yl)phenyl]-3-trifluoromethylimidazo[1,2-b][1,2,4]triazine

This reaction was carried out as described in Example 37, step e, using 3-[3-(5,5-dimethyl-[1,3,2]dioxaborinan-2-yl)phenyl]pyridine (150 mg, 0.56 mmol), 7-bromo-3-trifluoromethylimidazo[1,2-b][1,2,4]triazine (0.1 g, 0.375 mmol), 2 M Na$_2$CO$_3$ (0.56 ml) and tetrakis(triphenylphosphine)-palladium(0) (0.022 g) in 1,2-dimethoxyethane (2 ml). The crude residue was purified by flash chromatography (silica gel, 5% MeOH(CH$_2$Cl$_2$) to yield the title compound (56 mg, 44%): $^1$H NMR (400 MHz, CDCl$_3$) δ 7.42–7.45 (1H, m), 7.68–7.70 (2H, m), 7.95–7.98 (1H, m), 8.09–8.12 (1H, m), 8.34–8.35 (1H, m), 8.67 (1H, dd, J 4.7, 1.8 Hz), 8.68 (1H, s), 8.84 (1H, s), 8.93 (1H, dd, J 2.5, 0.8 Hz); MS (ES$^+$) m/z 342 [M+H]$^+$.

EXAMPLE 39

7-[3-([1,2,4]Triazol-1-yl)phenyl]-3-trifluoromethylimidazo[1,2-b][1,2,4]triazine a) 1-(3-Bromophenyl)-1H-[1,2,4]triazole A suspension of 3-bromophenylhydrazine hydrochloride (3.78 g, 17 mmol) in formamide (15 ml) was heated at 140° C. for 16 h. The reaction mixture was cooled to ambient temperature, diluted into dichloromethane (100 ml) and washed with water (2×100 ml). The organic phase was dried over anhydrous magnesium sulphate, filtered and evaporated to dryness to give 1-(3-bromophenyl)-1H-[1,2,4]triazole (3.44 g) as a tan solid: $^1$H NMR (400 MHz, CDCl$_3$) δ 8.57 (1H, s), 8.11 (1H, s), 7.90 (1H, t, J 2 Hz), 7.62–7.64 (1H, m), 7.53–7.55 (1H, m), 7.38 (1H, t, J 8 Hz).

b) 1-[3-(5,5-Dimethyl-[1,3,2]dioxaborinan-2-yl)phenyl]-1H-[1,2,4]triazole

This reaction was carried out as described in Example 37, step e, using 1-(3-bromophenyl)-1H-[1,2,4]triazole (0.7 g, 3.12 mmol), bis(neopentyl glycolato)diboron (0.776 g, 3.44 mmol), potassium acetate (0.919 g, 9.36 mmol) and [1,1'-bis(diphenylphosphino)ferrocene]-dichloropalladium(II) (127 mg, 5 mol %) in 1,4-dioxane (28 ml) to yield the title compound (0.34 g, 43%): $^1$H NMR (360 MHz, CDCl$_3$) δ 1.04 (6H, s), 3.80 (4H, s), 7.49 (1H, t, J 7.7 Hz), 7.73–7.78 (1H, m), 7.83 (1H, d, J 7.4 Hz), 8.05 (1H, d, J 1.8 Hz), 8.10 (1H, s), 8.62 (1H, s); MS (ES$^+$) m/z 190.

c) 7-[3-([1,2,4]Triazol-1-yl)phenyl]-3-trifluoromethylimidazo[1,2-b][1,2,4]triazine This reaction was carried out as described in Example 37, step e, using 1-[3-(5,5-dimethyl-[1,3,2]dioxaborinan-2-yl)phenyl]-1H-[1,2,4]triazole (192 mg, 0.75 mmol), 7-bromo-3-trifluoromethylimidazo[1,2-b][1,2,4]triazine (0.1 g, 0.375 mmol), 2 M Na$_2$CO$_3$ (0.75 ml) and tetrakis(triphenylphosphine)palladium(0) (0.022 g) in 1,2-dimethoxyethane (2 ml). The crude residue was purified by flash chromatography (silica gel, 5% MeOH/CH$_2$Cl$_2$) and triturated with Et$_2$O to yield the title compound (68 mg, 55%): $^1$H NMR (360 MHz, CDCl$_3$) δ 7.72 (1H, t, J 7.8 Hz), 7.76–7.80 (1H, m), 8.09–8.13 (1H, dt, J 7.8, 1.3 Hz), 8.17 (1H, s), 8.57 (1H, t, J 1.9 Hz), 8.67 (1H, s), 8.71 (1H, s), 8.87 (1H, s); MS (ES$^+$) m/z 332 [M+H]$^+$.

EXAMPLE 40

7-[3-(2-Methyl-2H-[1,2,3]triazol-4-yl)phenyl]-3-trifluoromethylimidazo[1,2-b][1,2,4]triazine a) 5-(3-Bromophenyl)-1-(2-trimethylsilanylethoxymethyl)-1H-[1,2,3]triazole A solution of butyllithium (5.0 mmol) in hexanes (1.6 M, 3.13 ml) was added to a stirred solution of 1-(2-trimethylsilanylethoxymethyl)-1H-[1,2,3]triazole (1.0 g, 5.0 mmol) in THF (50 ml) at −78° C. under nitrogen. The resulting mixture was stirred at −78° C. for 30 min and then warmed to room temperature and re-cooled to −78° C. A solution of zinc chloride (685 mg, 5.0 mmol) in THF (10 ml) was then added and the reaction mixture was warmed to room temperature. 3-Iodobromobenzene (640 μl, 5.0 mmol) and dichlorobis(triphenylphosphine)palladium(II) (176 mg, 5 mol %) were added and the resulting solution was heated at reflux for 14 h. The reaction mixture was poured into 1 N HCl solution (50 ml) and then extracted with diethyl ether (2×50 ml). The combined organic extracts were washed with brine (50 ml), dried (MgSO$_4$) and concentrated under reduced pressure. The crude residue was then purified by column chromatography (silica gel, 50% Et$_2$O/isohexane) to yield the substituted triazole (480 mg, 27%): $^1$H NMR (360 MHz, CDCl$_3$) δ 7.99 (2H, s), 7.65–7.55 (2H, m), 7.34 (1H, t, J 7.8 Hz), 5.66 (2H, s), 3.77 (2H, t, J 8.1 Hz), 0.94 (2H, m), 0.00 (9H, s).

b) 5-(3-Bromophenyl)-1H-[1,2,3]triazole

A mixture of 5-(3-bromophenyl)-1-(2-trimethylsilanylethoxymethyl)-1H-[1,2,3]triazole (1.27 g, 3.6 mmol), 2 N HCl (30 ml) and ethanol (30 ml) was heated at 60° C. for 3 h. The reaction mixture was cooled to room temperature and concentrated to approximately 5 ml under reduced pressure. The resulting solid was filtered off and dried under vacuum to yield the title compound (776 mg, 97%): $^1$H NMR (360 MHz, DMSO-d$_6$) δ 8.46 (1H, s), 8.07 (1H, s), 7.89 (1H, d, J 7.8 Hz), 7.55 (1H, d, J 7.8 Hz), 7.42 (1H, t, J 7.8 Hz).

c) 5-(3-Bromophenyl)-1-methyl-1H-[1,2,3]triazole, 4-(3-bromophenyl)-2-methyl-2H-[1,2,3]triazole and 4-(3-bromophenyl)-1-methyl-1H-[1,2,3]triazole Methyl iodide (323 μl, 5.2 mmol) was added to a stirred mixture of 5-(3-bromophenyl)-1H-[1,2,3]triazole (776 mg, 3.46 mmol) and potassium carbonate (1.19 g, 8.6 mmol) in DMF (20 ml) at room temperature under nitrogen. The reaction mixture was stirred overnight and then concentrated under reduced pressure. Water (50 ml) was added and then the mixture was extracted with ethyl acetate (3×50 ml). The combined organic extracts were concentrated under reduced pressure while dry loading onto silica gel. The residue was purified by column chromatography (silica gel, 50% Et₂O/isohexane) to yield first 4-(3-bromophenyl)-2-methyl-2H-[1,2,3]triazole (344 mg, 42%), the solvent polarity was increased to 80% Et₂O/isohexanes to yield 5-(3-bromophenyl)-1-methyl-1H-[1,2,3]triazole (15 mg, 2%), and then the solvent polarity was increased to 100% Et₂O to yield 4-(3-bromophenyl)-1-methyl-1H-[1,2,3]triazole (147 mg, 18%).

4-(3-Bromophenyl)-2-methyl-2H-[1,2,3]triazole: $^1$H NMR (400 MHz, CDCl₃) δ 7.94 (1H, s), 7.81 (1H, s), 7.68 (1H, d, J 7.0 Hz), 7.47 (1H, d, J 7.1 Hz), 7.29 (1H, t, J 7.1 Hz), 4.24 (3H, s).

5-(3-Bromophenyl)-1-methyl-1H-[1,2,3]triazole: $^1$H NMR (400 MHz, CDCl₃) δ 7.73 (1H, s), 7.68–7.57 (2H, m), 7.43–7.33 (2H, m), 4.08 (3H, s).

4-(3-Bromophenyl)-1-methyl-1H-[1,2,3]triazole: $^1$H NMR (400 MHz, CDCl₃) δ 7.98 (1H, s), 7.80–7.73 (2H, m), 7.45 (1H, d, J 7.9 Hz), 7.29 (1H, t, J 7.9 Hz), 4.16 (3H, s).

d) 4-[3-(5,5-Dimethyl-[1,3,2]dioxaborinan-2-yl)phenyl]-2-methyl-2H-[1,2,3]triazole A mixture of 4-(3-bromophenyl)-2-methyl-2H-[1,2,3]triazole (344 mg, 1.45 mmol), bis(neopentyl glycolato)diboron (343 mg, 1.52 mmol), potassium acetate (425 mg, 4.33 mmol) and [1,1'-bis(diphenylphosphino)ferrocene]dichloropalladium(II) (59 mg, 5 mol %) in 1,4-dioxane (20 ml) was degassed with a stream of nitrogen for 10 min and then heated at 110° C. for 16 h. The reaction mixture was divided into two portions, then concentrated under reduced pressure and used without further purification: MS (ES⁺) m/z 272 [M+H]⁺.

e) 7-[3-(2-Methyl-2H-[1,2,3]triazol-4-yl)phenyl]-3-trifluoromethylimidazo[1,2-b][1,2,4]triazine This reaction was carried out as described in Example 37, step e, using 4-[3-(5,5-dimethyl-[1,3,2]dioxaborinan-2-yl)phenyl]-2-methyl-2H-[1,2,3]triazole (190 mg, 0.7 mmol), 7-bromo-3-trifluoromethylimidazo[1,2-b][1,2,4]triazine (0.156 g, 0.585 mmol), 2 M Na₂CO₃ (0.70 ml) and tetrakis(triphenylphosphine)palladium(0) (0.034 g) in 1,2-dimethoxyethane (2 ml). The crude residue was purified by flash chromatography (silica gel, 50% Et₂O/toluene) and crystallized from toluene to yield the title compound (68 mg, 34%): $^1$H NMR (400 MHz, CDCl₃) δ 4.28 (3H, s), 7.63 (1H, t, J 7.8 Hz), 7.87 (1H, dt, J 7.8, 1.4 Hz), 7.91 (1H, s), 8.05–8.09 (1H, m), 8.52 (1H, t, J 1.4 Hz), 8.68 (1H, s), 8.85 (1H, s); MS (ES⁺) m/z 346 [M+H]⁺.

EXAMPLE 41

7-[3-(1-Methyl-1H-[1,2,4]triazol-3-yl)phenyl]-3-trifluoromethylimidazo[1,2-b][1,2,4]triazine a) 5-(3-Bromophenyl)-1-(2-trimethylsilanylethoxymethyl)-1H-[1,2,4]triazole This reaction was carried out as described in Example 40, step a, using 1-(2-trimethylsilanylethoxymethyl)-1H-[1,2,4]triazole (5.34 g, 26.8 mmol), butyllithium (26.8 mmol, 1.6 M in hexanes, 16.8 ml), zinc chloride (3.65 g, 26.8 mmol), 3-iodobromobenzene (3.42 ml, 26.8 mmol) and dichlorobis(triphenylphosphine)palladium(II) (942 mg, 5 mol %) to yield the title compound (2.98 g, 31%): $^1$H NMR (360 MHz, CDCl₃) δ 8.11 (1H, s), 7.94 (1H, s), 7.86 (1H, d, J 7.7 Hz), 7.62 (1H, d, J 7.8 Hz), 7.37 (1H, t, J 7.8 Hz), 5.49 (2H, s), 3.79 (2H, t, J 8.3 Hz), 0.97 (2H, t, J 8.3 Hz), 0.00 (9H, s).

b) 5-(3-Bromophenyl)-1H-[1,2,4]triazole

This reaction was carried out as described in Example 40, step b, using 5-(3-bromophenyl)-1-(2-trimethylsilanylethoxymethyl)-1H-[1,2,4]triazole (2.88 g, 8.1 mmol), 2 N HCl (50 ml) and ethanol (50 ml) to yield the title compound (1.62 g, 89%): $^1$H NMR (360 MHz, DMSO-d₆) δ 8.70 (1H, s), 8.16 (1H, s), 8.01 (1H, d, J 7.8 Hz), 7.63 (1H, d, J 7.8 Hz), 7.46 (1H, t, J 7.8 Hz).

c) 5-(3-Bromophenyl)-1-methyl-1H-[1,2,4]triazole and 3-(3-bromophenyl)-1-methyl-1H-[1,2,4]triazole This reaction was carried out as described in Example 40, step c, using 5-(3-bromophenyl)-1H-[1,2,4]triazole (1.60 g, 7.2 mmol), K₂CO₃ (2.47 g, 17.8 mmol) and MeI (667 μl, 10.7 mmol). The residue was purified by column chromatography (silica gel, 80% Et₂O/isohexane) to yield first 5-(3-bromophenyl)-1-methyl-1H-[1,2,4]triazole (190 mg, 11%), and then the solvent polarity was increased to 100% EtOAc to yield 3-(3-bromophenyl)-1-methyl-1H-[1,2,4]triazole (935 mg, 55%).

5-(3-Bromophenyl)-1-methyl-1H-[1,2,4]triazole: $^1$H NMR (400 MHz, CDCl₃) δ 7.95 (1H, s), 7.86 (1H, s), 7.68–7.58 (2H, m), 7.39 (1H, t, J 7.9 Hz), 4.01 (3H, s).

3-(3-Bromophenyl)-1-methyl-1H-[1,2,4]triazole: $^1$H NMR (400 MHz, CDCl₃) δ 8.26 (1H, s), 8.05 (1H, s), 8.02 (1H, d, J 7.8 Hz), 7.51 (1H, d, J 7.8 Hz), 7.30 (1H, t, J 7.8 Hz), 3.97 (3H, s).

d) 3-[3-(5,5-Dimethyl-[1,3,2]dioxaborinan-2-yl)phenyl-1-methyl-1H-[1,2,4]triazole A mixture of 3-(3-bromophenyl)-1-methyl-1H-[1,2,4]triazole (935 mg, 3.93 mmol), bis(neopentyl glycolato)diboron (932 mg, 4.13 mmol), potassium acetate (1.16 g, 11.8 mmol) and [1,1'-bis(diphenylphosphino)ferrocene]dichloropalladium(II) (160 mg, 5 mol %) in 1,4-dioxane (40 ml) was degassed with a stream of nitrogen for 10 min and then heated at 110° C. for 12 h. The reaction mixture was concentrated under reduced pressure and water (50 ml) was added; this was extracted with ethyl acetate (2×50 ml). The combined extracts were washed with brine (25 ml), dried (MgSO₄) and concentrated to give the title compound (106 mg, 99%): $^1$H NMR (400 MHz, CDCl₃) δ 8.55 (1H, s), 8.13 (1H, d, J 7.8 Hz), 8.07 (1H, s), 7.83 (1H, d, J 7.8 Hz), 7.42 (1H, t, J 7.8 Hz), 3.97 (1H, s), 3.77 (4H, s), 1.02 (6H, s); MS (ES⁺) m/z 204 (ArB(OH)₂, [M+H]⁺).

e) 7-[3-(1-Methyl-1H-[1,2,4]triazol-3-yl)phenyl-3-trifluoromethylimidazo[1,2-b][1,2,4]triazine This reaction was carried out as described in Example 37, step e, using 3-[3-(5,5-dimethyl-[1,3,2]dioxaborinan-2-yl)phenyl]-1-methyl-1H-[1,2,4]triazole (515 mg, 1.9 mmol), 7-bromo-3-trifluoromethylimidazo[1,2-b][1,2,4]triazine (0.461 g, 1.73 mmol), 2 M Na₂CO₃ (1.9 ml) and tetrakis(triphenylphosphine)palladium(0) (0.1 g) in 1,2-dimethoxyethane (4 ml). The crude residue was purified by flash chromatography (silica gel, 5% MeOH/CH₂Cl₂) and triturated with Et₂O to yield the title compound (346 mg, 58%). $^1$H NMR (360 MHz, CDCl₃) δ 4.02 (3H, s), 7.64 (1H, t, J 7.9 Hz), 8.11 (1H, s), 8.16 (1H, dt, J 8.2, 1.6 Hz), 8.21 (1H, dt, J 8.2, 1.6 Hz), 8.71 (1H, s), 8.81 (1H, t, J 1.4 Hz), 8.84 (1H, s); MS (ES⁺) m/z 346 [M+H]⁺.

EXAMPLE 42

7-[4-Fluoro-3-(imidazol-1-yl)phenyl]-3-trifluoromethylimidazo[1,2-b][1,2,4]triazine a) 1-(2-Fluoro-5-nitrolphenyl)-1H-imidazole 2-Fluoro-5-nitroaniline (4.0 g, 25.6 mmol) was treated with triethyl orthoformate (9.37 ml, 56.3 mmol) and the resulting mixture was heated at 120° C. for 45 min whilst allowing the ethanol produced to distil off. The reaction mixture was cooled to room temperature and methanol (50 ml) was added, followed by aminoacetaldehyde dimethyl acetal (9.49 ml, 87.1 mmol). The reaction mixture was then heated at 80° C. for 3.5 h before being cooled to room temperature, and the solvent removed under reduced pressure. 1,2-Dimethoxyethane (80 ml) was added and a solution of titanium(IV) chloride (35.9 ml) in dichloromethane (1.0 M, 50.2 mmol), was added dropwise over 10 min [N.B. exothermic]. The resulting mixture was stirred at room temperature for 30 min and then heated at reflux for 7 h. After cooling to room temperature the mixture was poured into 10% NaOH solution (200 ml) and chloroform (600 ml) added. The organics were separated and the aqueous extracted with CHCl$_3$ (2×150 ml). The combined organic extracts were washed with brine (150 ml), dried (MgSO$_4$) and concentrated under reduced pressure while loading onto silica. This was then purified by column chromatography (silica gel, EtOAc) to yield the title compound (300 mg, 6%): $^1$H NMR (400 MHz, CDCl$_3$) δ 8.37–8.32 (1H, m), 8.30–8.22 (1H, m), 7.92 (1H, s), 7.48 (1H, t, J 9.3 Hz), 7.34 (1H, s), 7.28 (1H, d, J 4.0 Hz); MS (ES$^+$) m/z 208 [M+H]$^+$.

b) 4-Fluoro-3-(imidazol-1-yl)phenylamine 1-(2-Fluoro-5-nitrophenyl)-1H-imidazole (300 mg, 1.45 mmol) was reduced as described in Example 37, step b, using tin(II) chloride (1.14 g, 6.0 mmol) in ethanol (10 ml) to yield the title compound (158 mg, 62%): $^1$H NMR (360 MHz, CDCl$_3$) δ 7.81 (1H, s), 7.22 (1H, s), 7.18 (1H, s), 7.02 (1H, dd, J 10.2, 8.8 Hz), 6.68–6.54 (2H, m); MS (ES$^+$) m/z 178 [M+H]$^+$.

c) 1-(5-Bromo-2-fluorophenyl)-1H-imidazole

4-Fluoro-3-(imidazol-1-yl)phenylamine (158 mg, 0.89 mmol) was treated with copper(II) bromide (219 mg, 0.98 mmol) and tert-butyl nitrite (265 μl, 2.22 mol) in acetonitrile (20 ml) as described in Example 37, step c, to yield, after column chromatography (silica gel, 5% MeOH/CH$_2$Cl$_2$+1% Et$_3$N) the title compound (162 mg, 75%): $^1$H NMR (400 MHz, CDCl$_3$) δ 7.82 (1H, s), 7.55 (1H, dd, J 6.8, 2.4 Hz), 7.49–7.42 (1H, m), 7.26–7.12 (3H, m); MS (ES$^+$) m/z 241, 243 (1:1, [M+H]$^+$).

d) 1-[5-(5,5-Dimethyl-[1,3,2]dioxaborinan-2-yl)-2-fluorophenyl]-1H-imidazole

This reaction was carried out as described in Example 37, step d, using 1-(5-bromo-2-fluorophenyl)-1H-imidazole (0.2 g, 0.83 mmol), bis(neopentyl glycolato)diboron (0.21 g, 0.91 mmol), potassium acetate (0.25 g, 2.5 mmol) and [1,1'-bis(diphenylphosphino)ferrocene]-dichloropalladium (II) (34 mg, 5 mol %) in 1,4-dioxane (15 ml) to yield the desired boronate ester (quantitative): MS (ES$^+$) m/z 206.

e) 7-[4-Fluoro-3-(imidazol-1-yl)phenyl]-3-trifluoromethylimidazo[1,2-b][1,2,4]triazine This reaction was carried out as described in Example 37, step e, using 1-[5-(5,5-dimethyl-[1,3,2]dioxaborinan-2-yl)-2-fluorophenyl]-1H-imidazole (344 mg, 1.67 mmol), 7-bromo-3-trifluoromethylimidazo[1,2-b][1,2,4]triazine (0.446 g, 1.67 mmol), 2 M Na$_2$CO$_3$ (1.67 ml) and tetrakis(triphenylphosphine)palladium(0) (0.096 g) in 1,2-dimethoxyethane (6 ml). The crude residue was purified by flash chromatography (silica gel, 3% MeOH(CH$_2$Cl$_2$) and triturated with Et$_2$O to yield the title compound (77 mg, 13%): $^1$H NMR (360 MHz, CDCl$_3$) δ 7.29 (1H, s), 7.35 (1H, d, J 1.4 Hz), 7.50 (1H, t, J 9.1 Hz), 7.92 (1H, s), 8.04–8.08 (1H, m), 8.30 (1H, dd, J 7.0, 2.1 Hz), 8.64 (1H, s), 8.84 (1H, s); MS (ES$^+$) m/z 349 [M+H]$^+$.

EXAMPLE 43

7-[4-Fluoro-3-(pyridin-3-yl)phenyl]-3-trifluoromethylimidazo[1,2-b][1,2,4]triazine a) 3-[2-Fluoro-5-(4,4,5,5-tetramethyl-[1,3,2]dioxaborolan-2-yl)phenyl]pyridine 2-Bromo-1-fluoro-4-nitrobenzene was dissolved in tetrahydrofuran (75 ml) and ethanol (75 ml) and tin(II) chloride dihydrate added and the mixture left to stir at ambient temperature for 4 h. The solvent was evaporated and the residue was treated with ice-cold 2 N sodium hydroxide solution (200 ml). The resulting slurry was stirred for 30 min then extracted with dichloromethane (3×200 ml). The combined organic phase was washed with water (200 ml) and brine (200 ml), dried over anhydrous magnesium sulfate, filtered and evaporated to give 3-bromo-4-fluorophenylamine (7.92 g, 92%) as a yellow oil: $^1$H NMR (360 MHz, CDCl$_3$) δ 3.53 (2H, s), 6.53–6.57 (1H, m), 6.83–6.85 (1H, m), 6.90 (1H, dd, J 9, 9 Hz).

A mixture of 3-bromo-4-fluorophenylamine (7.92 g, 41.7 mmol), diethyl(3-pyridyl)borane (6.74 g, 45.9 mmol), tetrakis(triphenylphosphine)palladium(0) (0.96 g, 0.83 mmol) and potassium carbonate (17.26 g, 125 mmol) in 1,2-dimethoxyethane (30 ml) and water (15 ml) was heated at 80° C. for 20 h. After cooling to ambient temperature the reaction was partitioned between ethyl acetate (500 ml) and water (500 ml). The organics were washed with brine (400 ml), dried over anhydrous sodium sulfate, filtered and concentrated in vacuo. Purification of the residue by flash chromatography (silica gel, 0–20% EtOAc/CH$_2$Cl$_2$) gave 4-fluoro-3-(pyridin-3-yl)phenylamine (3.64 g, 46%) as a colourless oil that solidified on standing to afford a white solid: $^1$H NMR (360 MHz, CDCl$_3$) δ 3.65 (2H, s), 6.65–6.72 (2H, m), 6.99 (1H, dd, J 9, 9 Hz), 7.33–7.37 (1H, m), 7.84–7.86 (1H, m), 8.58 (1H, d, J 4 Hz), 8.76 (1H, m).

A warm solution of 4-fluoro-3-(pyridin-3-yl)phenylamine (3.64 g, 19.3 mmol) in 1,4-dioxane (10 ml) was treated with a solution of 48% aqueous hydrobromic acid (100 ml). The resulting suspension was cooled to 0° C. before being treated dropwise over 20 min with a solution of sodium nitrite (1.53 g, 22.2 mmol) in water (4 ml). After stirring at 0° C. for 2 h, a cooled (0° C.) solution of copper(I) bromide (8.31 g, 57.9 mmol) in 48% aqueous hydrobromic acid (30 ml) was added to the reaction, which was stirred at 0° C. for 10 min then heated at 50° C. for 20 min. The reaction was cooled to ambient temperature, poured onto ice-cold concentrated ammonia (500 ml) and the product was extracted into ethyl acetate (500 ml). The organic extract was washed with water (300 ml) and brine (300 ml), dried over anhydrous sodium sulfate, filtered and concentrated in vacuo to give a dark oil. Purification by dry flash column chromatography (silica gel, 10–30% EtOAc/isohexane) gave 3-(5-bromo-2-fluorophenyl)pyridine (3.1 g, 64%) as a white solid: $^1$H NMR (360 MHz, CDCl$_3$) δ 7.09 (1H, dd, J 9, 1 Hz), 7.37–7.40 (1H, m), 7.46–7.51 (1H, m), 7.56–7.59 (1H, m), 7.83–7.86 (1H, m), 8.63–8.65 (1H, m), 8.77–8.79 (1H, m).

3-(5-Bromo-2-fluorophenyl)pyridine (3.1 g, 12.3 mmol), potassium acetate (3.62 g, 36.9 mmol) and bis(pinacolato)diboron (3.75 g, 14.8 mmol) were dissolved in 1,4-dioxane (40 ml) and dimethylsulfoxide (0.8 ml) and the mixture degassed with N$_2$ for 15 min. Dichloro[1,1'-bis(diphenylphosphino)ferrocene]palladium(II) dichloromethane adduct (300 mg, 0.37 mmol) was added and the mixture heated at 90° C. for 18 h. The mixture was cooled to ambient temperature and partitioned between diethyl ether (200 ml) and 1 N hydrochloric acid (50 ml). The organics were discarded and the aqueous phase adjusted to pH 8 by the addition of 4 N sodium hydroxide solution and extracted with diethyl ether (2×500 ml). The organic layer was washed with brine (50 ml), dried over anhydrous sodium sulfate, filtered and pre-adsorbed onto silica. Purification by flash column chromatography (silica gel, 25% EtOAc/isohexane) gave 3-[2-fluoro-5-(4,4,5,5-tetramethyl-[1,3,2]dioxaborolan-2-yl)phenyl]pyridine (2.64 g, 72%) as a yellow oil that crystallised on standing: $^1$H NMR (360 MHz, CDCl$_3$) δ 1.35 (12H, s), 7.20 (1H, dd, J 10, 8 Hz), 7.35–7.39 (1H, m), 7.81–7.91 (3H, m), 8.61 (1H, dd, J 5, 2 Hz), 8.82 (1H, s).

b) 7-[4-Fluoro-3-(pyridin-3-yl)phenyl]-3-trifluoromethylimidazo[1,2-b][1,2,4]triazine 3-[2-Fluoro-5-(4,4,5,5-tetramethyl-[1,3,2]dioxaborolan-2-yl)phenyl]pyridine (151 mg, 0.51 mmol) was coupled to 7-bromo-3-trifluoromethylimidazo[1,2-b][1,2,4]triazine (0.09 g, 0.34 mmol) as described in Example 37, step e, using 2 M $Na_2CO_3$ (0.51 ml) and tetrakis(triphenylphosphine)palladium(0) (0.019 g) in 1,2-dimethoxyethane (2 ml). The crude residue was purified by flash chromatography (silica gel, 2.5% $MeOH/CH_2Cl_2$) and triturated with $Et_2O$ to yield the title compound (54 mg, 45%): $^1H$ NMR (400 MHz, $CDCl_3$) δ 7.38–7.47 (2H, m), 7.94–7.97 (1H, m), 8.08–8.12 (1H, m), 8.24 (1H, dd, J 7.0, 2.3 Hz), 8.62 (1H, s), 8.69 (1H, dd, J 4.8, 1.6 Hz), 8.82 (1H, s), 8.88 (1H, s); MS ($ES^+$) m/z 359, 360.

EXAMPLE 44

7-[4-Fluoro-3-(5-fluoropyridin-2-yl)phenyl]-3-trifluoromethylimidazo[1,2-b][1,2,4]triazine a) 4-Fluoro-3-(5-fluoropyridin-2-yl)phenylboronic Acid To a degassed mixture of 2-bromo-5-fluoropyridine (1.88 g, 10.7 mmol), 2-(2-fluoro-5-nitrophenyl)-4,4,5,5-tetramethyl-[1,3,2]dioxaborolane (3.13 g, 11.6 mmol) and potassium phosphate (8.2 g, 38.6 mmol) in 1,4-dioxane (40 ml) was added dichloro[1,1'-bis(diphenylphosphino) ferrocene]-palladium(II) dichloromethane adduct (189 mg) and the mixture stirred for 24 h at 90° C. The reaction was cooled to ambient temperature, poured into water (100 ml) and extracted with ethyl acetate (4×50 ml). The combined organic phases were dried over anhydrous sodium sulfate, filtered and evaporated to dryness. Purification by chromatography (silica gel, $CH_2Cl_2$) and then crystallisation from isohexane gave 5-fluoro-2-(2-fluoro-5-nitrophenyl)pyridine (1.23 g, 44%): MS ($ES^+$) m/z 237.

To a solution of 5-fluoro-2-(2-fluoro-5-nitrophenyl) pyridine (1.23 g) in ethanol (70 ml) and dichloromethane (30 ml) was added platinum(IV) oxide (150 mg) and the mixture shaken on a Parr hydrogenation apparatus under an atmosphere of hydrogen at 45 psi for 1 h. Filtration and evaporation of the filtrate afforded 4-fluoro-3-(5-fluoropyridin-2-yl)phenylamine: MS ($ES^+$) m/z 207.

4-Fluoro-3-(5-fluoropyridin-2-yl)phenylamine (1.2 g) was dissolved in 1,4-dioxane (4 ml) and 48% aqueous hydrobromic acid (30 ml). The solution was cooled to 0° C. A solution of sodium nitrite (478 mg) in water (6 ml) was added dropwise with stirring to maintain an internal temperature below 4° C. The mixture was then aged a further 1 h at 4° C. A solution of copper(I) bromide (2.58 g) in 48% aqueous hydrobromic acid (10 ml) was then added slowly to retain a reaction temperature below 5° C. The resulting mixture was then stirred at 5–10° C. for 1 h, ambient temperature for 0.5 h and then heated at 50° C. for 0.5 h. The mixture was then cooled to 4° C., and made basic by addition of 4 N aqueous sodium hydroxide (106 ml), followed by 30% aqueous ammonium hydroxide (40 ml). The mixture was extracted with ethyl acetate, the organic phase dried over anhydrous sodium sulfate, filtered and evaporated to dryness. The residue was chromatographed (silica gel, 70% $CH_2Cl_2$/isohexane) to afford 2-(5-bromo-2-fluorophenyl)-5-fluoropyridine: $^1H$ NMR (400 MHz, DMSO) δ 8.74 (1H, dd, J 2, 1 Hz), 8.05 (1H, dd, J 7, 3 Hz), 7.90 (2H, m), 7.69 (1H, m), 7.38 (1H, dd, J 11, 9 Hz); MS ($ES^+$) m/z 270, 272.

To 2-(5-bromo-2-fluorophenyl)-5-fluoropyridine (0.94 g, 3.48 mmol) and bis(neopentyl glycolato)diboron (0.943 g) in 1,4-dioxane (12 ml) and dimethylsulfoxide (1.5 ml) was added potassium acetate (0.725 g) and dichloro[1,1'-bis (diphenylphosphino)ferrocene]palladium(II) dichloromethane adduct (100 mg). The mixture was degassed with nitrogen and then stirred at 85° C. for 15 h. On cooling to ambient temperature, 1 N aqueous sodium hydroxide (32 ml) was added and the mixture stirred for 20 min. Diethyl ether was added and the aqueous phase separated and washed with diethyl ether. The organic extracts were washed with water and the combined aqueous phases filtered then acidified to pH 5 by addition of 2 N aqueous hydrochloric acid (18 ml). The resulting white solid was collected by filtration, washed with water and dried in vacuo to afford 4-fluoro-3-(5-fluoropyridin-2-yl)phenylboronic acid: $^1H$ NMR (400 MHz, DMSO-$d_6$) δ68.73 (1H, dd, J 2 and 1), 8.33 (1H, dd, J 9 and 2), 8.17 (2H, s), 7.87 (3H, m), 7.31 (1H, dd, J 12 and 8).

b) 7-[4-Fluoro-3-(5-fluoropyridin-2-yl)phenyl]-3-trifluoromethylimidazo[1,2-b][1,2,4]triazine 4-Fluoro-3-(5-fluoropyridin-2-yl)phenylboronic acid (61 mg, 0.25 mmol) was coupled to 7-bromo-3-trifluoromethylimidazo[1,2-b][1,2,4]triazine (0.046 g, 0.17 mmol) as described in Example 37, step e, using 2 M $Na_2CO_3$ (0.26 ml) and tetrakis(triphenylphosphine) palladium(0) (0.010 g) in 1,2-dimethoxyethane (2 ml). The crude residue was purified by flash chromatography (silica gel, 2.5% $MeOH/CH_2Cl_2$) and triturated with $Et_2O$ to yield the title compound (23 mg, 35%): $^1H$ NMR (400 MHz, $CDCl_3$) δ 7.39 (1H, dd, J 8.8, 10.8 Hz), 7.51–7.56 (1H, m), 8.89–7.94 (1H, m), 8.14–8.17 (1H, m), 8.63 (1H, d, J 2.7 Hz), 8.66 (1H, s), 8.74 (1H, dd, J 7.4, 2.3 Hz), 8.83 (1H, s); MS ($ES^+$) m/z 378 [M+H]$^+$.

EXAMPLE 45

7-[3-(Pyrrol-1-yl)phenyl]-3-trifluoromethylimidazo [1,2-b][1,2,4]triazine a) 3-(3-Trifluoromethylimidazo[1,2-b][1,2,4]triazin-7-yl) phenylamine This reaction was carried out as in Example 6, step b, using a mixture of 3-aminophenylboronic acid (290 mg, 1.87 mmol) and 7-bromo-3-trifluoromethylimidazo[1,2-b] [1,2,4]triazine (250 mg, 0.93 mmol). The residue was purified by flash chromatography (silica gel, 35% EtOAc/ isohexane) to give 105 mg (41%) of the title compound: $^1H$ NMR (400 MHz, $CDCl_3$) δ 3.87 (2H, br s), 6.80 (1H, ddd, J 7.9, 2.4, 0.8 Hz), 7.34 (1H, t, J 7.9 Hz), 7.46–7.43 (2H, m), 8.57 (1H, s), 8.77 (1H, s); MS ($ES^+$) m/z 280 [M+H]$^+$.

b) 7-[3-(Pyrrol-1-yl)phenyl]-3-trifluoromethylimidazo[1,2-b][1,2,4]triazine

A mixture of 3-(3-trifluoromethylimidazo[1,2-b][1,2,4] triazin-7-yl)phenylamine and 2,5-dimethoxytetrahydrofuran in acetic acid was heated at 130° C. for 20 min. The reaction mixture was cooled to room temperature and concentrated under reduced pressure. The residue was purified by flash chromatography (silica gel, 10% $Et_2O$/isohexane) to give 40 mg (62%) of the title compound: $^1H$ NMR (400 MHz, $CDCl_3$) δ 6.41 (2H, t, J 2.2 Hz), 7.18 (2H, t, J 2.2 Hz), 7.51 (1H, ddd, J 8.3, 2.5, 1.1 Hz), 7.62 (1H, t, J 8.3 Hz), 7.92 (1H, dt, J 8.8, 1.1 Hz), 8.21 (1H, t, J 2.2 Hz), 8.66 (1H, s), 8.81 (1H, s); MS ($ES^+$) m/z 330 [M+H]$^+$.

EXAMPLE 46

7-[3-(Pyridin-4-yl)phenyl]-3-trifluoromethylimidazo [1,2-b][1,2,4]triazine a) 7-(3-Bromophenyl)-3-trifluoromethylimidazo[1,2-b][1,2, 4]triazine 3-(3-Trifluoromethylimidazo[1,2-b][1,2,4]triazin-7-yl) phenylamine (750 mg, 2.69 mmol) in 1,4-dioxane (15 ml)

and 48% HBr (6 ml) was cooled to 0° C., then sodium nitrite (204 mg, 2.96 mmol) was added portionwise as a solution in water (2 ml). The mixture was stirred for 1 h at 4° C., then a solution of copper(I) bromide in 48% HBr was added, keeping the temperature below 4° C. Finally the solution was stirred at 5–10° C. for 1 h and allowed to warm to room temperature. To the reaction mixture was added 4 N NaOH (30 ml) followed by 30% aqueous ammonia (15 ml). The resultant mixture was extracted with dichloromethane (3×25 ml), and the organic extracts were combined, dried with MgSO$_4$ and concentrated under reduced pressure. The residue was purified by chromatography (silica gel, 10% EtOAc/isohexane and then 20% Et$_2$O/isohexane) to give 193 mg (21%) of the title compound: $^1$H NMR (360 MHz, CDCl$_3$) δ 7.44 (1H, t, J 8.1 Hz), 7.61 (1H, d, J 8.1 Hz), 8.01 (1H, d, J 8.1 Hz), 8.30 (1H, s), 8.61 (1H, s), 8.81 (1H, s); MS (ES$^+$) m/z 343, 345.

b) 7-[3-(Pyridin-4-yl)phenyl]-3-trifluoromethylimidazo[1,2-b][1,2,4]triazine

A mixture of 7-(3-bromophenyl)-3-trifluoromethylimidazo[1,2-b][1,2,4]triazine (21 mg, 0.06 mmol), 4-pyridylboronic acid (11 mg, 0.09 mmol) and 2 M Na$_2$CO$_3$ (0.09 ml) in 1,2-dimethoxyethane (1.5 ml) was degassed with a stream of nitrogen for 10 min. Tetrakis(triphenylphosphine)palladium(0) (4 mg, 0.003 mmol) was added and the mixture was stirred under nitrogen at 65° C. for 12 h. After allowing to cool to room temperature, the mixture was diluted with ethyl acetate and partitioned between water (20 ml) and ethyl acetate (30 ml). The organic extracts were dried (MgSO$_4$) and evaporated in vacuo. The residue was purified by flash chromatography (silica gel, 5% MeOH/CH$_2$Cl$_2$) and triturated with diethyl ether to give 9.2 mg (44%) of the title compound: $^1$H NMR (400 MHz, CDCl$_3$) δ 7.58 (2H, m), 7.70 (1H, t, J 7.3 Hz), 7.74–7.77 (1H, m), 8.13 (1H, dt, J 7.3, 1.6 Hz), 8.39 (1H, t, J 1.6 Hz), 8.68 (1H, s), 8.72 (2H, m), 8.83 (1H, s); MS (ES$^+$) m/z 342 [M+H]$^+$.

EXAMPLE 47

7-[3-(Thiazol-2-yl)phenyl]-3-trifluoromethylimidazo[1,2-b][1,2,4]triazine

A mixture of 7-(3-bromophenyl)-3-trifluoromethylimidazo[1,2-b][1,2,4]triazine (0.2 g, 0.58 mmol), 2-tributylstannylthiazole (0.44 g, 1.17 mmol) and tetrakis(triphenylphosphine)palladium(0) (67 mg, 0.06 mmol) in THF (2 ml) was degassed with a stream of N$_2$ for 10 min and stirred at 65° C. for 12 h. After allowing to cool to room temperature, the mixture was concentrated in vacuo. The residue was purified by flash chromatography (silica gel, 25% EtOAc/isohexane) and triturated with Et$_2$O to give 64 mg (32%) of the title compound: $^1$H NMR (360 MHz, CDCl$_3$) δ 7.42 (1H, d, J 3.2 Hz), 7.65 (1H, t, J 7.9 Hz), 7.94 (1H, d, J 3.2 Hz), 8.04 (1H, dq, J 7.9, 1.0 Hz), 8.06 (1H, dq, J 7.9, 1.0 Hz), 8.71 (1H, s), 8.76 (1H, t, J 1.6 Hz), 8.86 (1H, s); MS (ES$^+$) m/z 348 [M+H]$^+$.

EXAMPLE 48

7-[3-(5-Fluoropyridin-2-yl)phenyl]-3-trifluoromethylimidazo[1,2-b][1,2,4]triazine a) 7-[3-(5,5-Dimethyl-[1,3,2]dioxaborinan-2-yl)phenyl]-3-trifluoromethylimidazo[1,2-b][1,2,4]triazine A solution of 7-(3-bromophenyl)-3-trifluoromethylimidazo[1,2-b][1,2,4]triazine (0.380 g, 1.11 mmol) in 1,4-dioxane (50 ml) was degassed by evacuation and refilling with nitrogen three times before dichloro[1,1'-bis(diphenylphosphino)ferrocene]palladium(II) dichloromethane adduct (0.045 g, 0.055 mmol), potassium acetate (0.326 g, 3.32 mmol) and bis(neopentyl glycolato)diboron (0.253 g, 1.12 mmol) were added. The mixture was degassed again before heating at reflux temperature for 12 h. The mixture was partitioned between water (15 ml) and diethyl ether (15 ml). The aqueous layer was washed with diethyl ether (3×15 ml), and the organic extracts were combined, dried (MgSO$_4$) and concentrated under reduced pressure to give 421 mg (quantitative) of the title compound: $^1$H NMR (400 MHz, CDCl$_3$) δ 1.06 (6H, s), 3.82 (4H, s), 7.55 (1H, t, J 7.7 Hz), 7.91 (1H, dt, J 7.7, 1.2 Hz), 8.19 (1H, dq, J 7.7, 1.2 Hz), 8.44 (1H, s), 8.64 (1H, s), 8.81 (1H, s); MS (ES$^+$) m/z 309.

b) 7-[3-(5-Fluoropyridin-2-yl)phenyl]-3-trifluoromethylimidazo[1,2-b][1,2,4]triazine 7-[3-(5,5-Dimethyl-[1,3,2]dioxaborinan-2-yl)phenyl]-3-trifluoromethylimidazo[1,2-b][1,2,4]triazine (0.2 g, 0.53 mmol) was added to 1,2-dimethoxyethane (2 ml), 2-bromo-5-fluoropyridine (94 mg, 0.53 mmol) and 2 N Na$_2$CO$_3$ (0.53 ml). The mixture was degassed with a stream of nitrogen for 10 min before tetrakis(triphenylphosphine)palladium(0) (31 mg, 0.027 mmol) was added and the mixture heated at 80° C. for 6 h. The mixture was cooled to ambient temperature before partitioning between water (15 ml) and ethyl acetate (15 ml). The organic extracts were then washed with NaOH (15 ml), dried (MgSO$_4$) and evaporated in vacuo. The residue was purified by chromatography (silica gel, 3% MeOH/CH$_2$Cl$_2$) then triturated with diethyl ether to give 53 mg (28%) of the title compound: $^1$H NMR (400 MHz, CDCl$_3$) δ 7.51–7.56 (1H, m), 7.67 (1H, t, J 7.7 Hz), 7.83 (1H, dd, J 9.2, 4.1 Hz), 8.03 (1H, dq, J 7.7, 1.0 Hz), 8.14 (1H, dq, J 7.7, 1.0 Hz), 8.60 (1H, d, J 3.1 Hz), 8.70 (1H, s), 8.72 (1H, t, J 1.6 Hz), 8.84 (1H, s); MS (ES$^+$) m/z 360 [M+H]$^+$.

EXAMPLE 49

7-[4-Fluoro-3-(pyrazol-1-yl)phenyl]-3-trifluoromethylimidazo[1,2-b][1,2,4]triazine A solution of pyrazole (6.8 g, 100 mmol) was formed in N,N-dimethylformamide (80 ml) and cooled to 0° C. Sufficient sodium hydride (4.36 g, 182 mmol) was added until hydrogen evolution ceased. With the temperature maintained at 0° C., 3,4-difluoronitrobenzene (10 ml, 95 mmol) was added dropwise. The mixture was stirred at room temperature for 18 h. The mixture was added to water (1 l) and the resulting yellow precipitate was filtered and sucked dry. Purification of the filter by chromatography on silica gel eluting with dichloromethane, then recrystalisation from dichloromethane with isohexane, gave 1-(2-fluoro-4-nitrophenyl)-1H-pyrazole as a yellow solid: $^1$H NMR (400 MHz, CDCl$_3$) δ 6.57 (1H, dd, J 3, 2 Hz), 7.82 (1H, d, J 2 Hz), 8.14–8.20 (3H, m), 8.25–8.30 (1H, m).

A solution of 1-(2-fluoro-4-nitrophenyl)-1H-pyrazole (3 g, 14.5 mmol) and platinum(IV) oxide (100 mg) in ethanol (100 ml) with ethyl acetate (100 ml) was reduced under 40 psi hydrogen for 30 min, then filtered and the solvent removed, to give 5-fluoro-4-(pyrazol-1-yl)phenylamine as a colourless oil: MS (ES$^+$) m/z 178 [M+H]$^+$.

To a solution of 5-fluoro-4-(pyrazol-1-yl)phenylamine (2.56 g, 14.5 mmol) in tetrahydrofuran (50 ml) was added dropwise a solution of pyridinium tribromide (5.09 g, 15.9 mmol) in tetrahydrofuran (50 ml). The mixture was stirred for 1 h at room temperature then diluted with diethyl ether (250 ml). After stirring for a further 30 min the precipitate was filtered and washed with diethyl ether (50 ml×2). The white solid was dissolved in water (200 ml) and extracted with ethyl acetate (100 ml×3). The combined organic phases were dried over magnesium sulphate, filtered and the solvent removed to leave an orange oil. Purification by chromatography (silica gel, $CH_2Cl_2$) gave 2-bromo-5-fluoro-4-(pyrazol-1-yl)phenylamine as a white solid: MS ($ES^+$) m/z 256 and 258 $[M+H]^+$.

A solution of 2-bromo-5-fluoro-4-(pyrazol-1-yl)phenylamine (1.94 g, 7.58 mmol) was formed in sulphuric acid (50%, 40 ml), and cooled to 0° C. Sodium nitrite (732 mg, 10.6 mmol) was added dropwise as a solution in water (5 ml) maintaining internal temperature <5° C. The mixture was stirred at 0° C. for 1 h. Ethanol (5 ml) and then iron sulphate heptahydrate (1.05 g, 3.79 mmol) was added and the mixture allowed to warm to room temperature for 2 h. The mixture was cooled to 0° C. and neutralised with sodium hydroxide solution (4 N) then extracted with ethyl acetate (4×50 ml). The combined organic phases were dried over magnesium sulphate, filtered and the solvent removed to leave an orange oil. Purification by chromatography on silica gel eluting with dichloromethane gave 1-(5-bromo-2-fluorophenyl)-1H-pyrazole as an orange solid: (400 MHz, $CDCl_3$) δ 6.49 (1H, dd, J 3, 2 Hz), 7.12 (1H, dd, J 11, 9 Hz), 7.34–7.39 (1H, m), 7.75 (1H, d, J 2 Hz), 8.02 (1H, t, J 3 Hz), 8.13 (1H, dd, J 7, 2 Hz).

A degassed solution of 1-(5-bromo-2-fluorophenyl)-1H-pyrazole (1 g, 4.15 mmol) and bis(neopentyl glycolato)diboron (1.03 g, 4.56 mmol) was formed in 1,4-dioxane (20 ml) with dimethylsulphoxide (0.4 ml). Potassium acetate (815 mg, 8.3 mmol) and dichloro[1,1'-bis(diphenylphosphino)ferrocene]palladium(II) dichloromethane adduct (60 mg, 0.1 mmol) were added and the mixture stirred at 80° C. for 18 h. The reaction was allowed to cool to ambient temperature and the solvent removed under reduced pressure. The residue was dissolved in 2 N sodium hydroxide solution (50 ml) and filtered. The filtrate was washed with diethyl ether (3×50 ml) then cooled to 0° C. and neutralised with concentrated hydrochloric acid. The resulting precipitate was filtered and dried over phosphorus pentoxide to give 1-[5-(5,5-dimethyl-[1,3,2]dioxaborinan-2-yl)-2-fluorophenyl]-1H-pyrazole as a white solid: $^1$H NMR (400 MHz, DMSO-$d_6$) δ 0.96 (6H, s), 3.78 (4H, s), 6.57 (1H, t, J 2 Hz), 7.44 (1H, dd, J 12, 8 Hz), 7.67–7.71 (1H, m), 7.79 (1H, d, J 2 Hz), 8.08 (1H, dd, J 9, 2 Hz), 8.21 (1H, t, J 3 Hz).

7-Bromo-3-trifluoromethylimidazo[1,2-b)(1,2,4]triazine was coupled with 1-[5-(5,5-dimethyl-[1,3,2]dioxaborinan-2-yl)-2-fluorophenyl]-1H-pyrazole as described in Example 3, step f, final paragraph, to give 41 mg (39%) of the title compound: $^1$H NMR (360 MHz, DMSO-$d_6$) δ 6.63 (1H, t, J 2.1 Hz), 7.74 (1H, dd, J 8.7, 11.2 Hz), 8.23 (1H, ddd, J 2.1, 4.2, 8.7 Hz), 8.31 (1H, t, J 2.8 Hz), 8.71 (1H, dd, J 2.5, 7.7 Hz), 9.00 (1H, s), 9.41 (1H, s); MS ($ES^+$) m/z 349 $[M+H]^+$.

EXAMPLE 50

7-[4-Fluoro-3-([1,2,4]triazol-1-yl)phenyl]-3-trifluoromethylimidazo[1,2-b][1,2,4]triazine 1H-[1,2,4]Triazole (6.91 g, 100 mmol) was reacted with sodium hydride (4.3 g, 180 mmol) then with 3,4-difluoronitrobenzene (10 ml, 95 mmol) as in Example 49 to give 1-(2-fluoro-4-nitrophenyl)-1H-[1,2,4]triazole as a yellow solid: $^1$H NMR (400 MHz, $CDCl_3$) δ 8.19–8.28 (4H, m), 8.85 (1H, d, J 3 Hz).

1-(2-Fluoro-4-nitrophenyl)-1H-[1,2,4]triazole (3 g, 14 mmol) was reduced using the method in Example 49 to give 5-fluoro-4-([1,2,4]triazol-1-yl)phenylamine as a white solid: $^1$H NMR (400 MHz, $CDCl_3$) δ 3.99 (2H, s), 6.51–6.56 (2H, m), 7.50 (1H, t, J 9 Hz), 8.07 (1H, s), 8.45 (1H, d, J 3 Hz).

5-Fluoro-4-([1,2,4]triazol-1-yl)phenylamine (2.2 g, 12 mmol) was brominated using the method in Example 49 to give 2-bromo-5-fluoro-4-([1,2,4]triazol-1-yl)phenylamine as a white solid: $^1$H NMR (360 MHz, $CDCl_3$) δ 4.40 (2H, br s), 6.65 (1H, d, J 12 Hz), 7.86 (1H, d, J 7 Hz), 8.08 (1H, s), 8.47 (1H, d, J 3 Hz).

2-Bromo-5-fluoro-4-([1,2,4]triazol-1-yl)phenylamine (1.35 g, 5.24 mmol) was deaminated using the method in Example 49 to give 1-(5-bromo-2-fluorophenyl)-1H-[1,2,4]triazole as a brown solid: $^1$H NMR (400 MHz, $CDCl_3$) δ 7.19 (1H, dd, J 11, 9 Hz), 7.46–7.50 (1H, m), 8.11–8.13 (2H, m), 8.69 (1H, d, J 3 Hz).

1-(5-Bromo-2-fluorophenyl)-1H-[1,2,4]triazole (1.1 g, 4.5 mmol) was reacted with bis(neopentyl glycolato)diboron (1.13 g, 5.0 mmol) using the method in Example 49 to give 4-fluoro-3-([1,2,4]triazol-1-yl)phenylboronic acid as a white solid: MS ($ES^+$) m/z 208 $[M+H]^+$.

7-Bromo-3-trifluoromethylimidazo[1,2-b][1,2,4]triazine was coupled with 4-fluoro-3-([1,2,4]triazol-1-yl)phenylboronic acid as described in Example 3, step f, final paragraph, to give the title compound: $^1$H NMR (360 MHz, DMSO-d6) δ 7.82 (1H, dd, J 8.7, 10.5 Hz), 8.34–8.39 (1H, m), 8.39 (1H, s), 8.71 (1H, dd, J 2.4, 7.4 Hz), 9.02 (1H, s), 9.13 (1H, d, J 2.4 Hz); MS ($ES^+$) m/z 350 $[M+H]^+$.

EXAMPLE 51

7-[4-Fluoro-3-(oxazol-2-yl)phenyl]-3-trifluoromethylimidazo[1,2-b][1,2,4]triazine A solution of trifluoromethanesulfonic acid 2-fluoro-5-(3-trifluoromethylimidazo[1,2-b][1,2,4]triazin-7-yl)phenyl ester (45 mg, 0.104 mmol), 2-(tributylstannyl)oxazole (70 mg, 0.196 mmol), tetrakis(triphenylphosphine)palladium(0) (30 mg, 0.026 mmol) and copper(I) iodide (15 mg, 0.079 mmol) in 1,4-dioxane (4 ml) was heated at 170° C. for 30 min using a Smith Synthesizer microwave apparatus. The mixture was evaporated in vacuo and the residue was purified by chromatography (silica gel, 8% $Et_2O/CH_2Cl_2$), followed by trituration with diethyl ether, to give 13 mg (35%) of the title compound: $^1$H NMR (360 MHz, $CDCl_3$) δ 7.37 (1H, s), 7.42 (1H, dd, J 8.7, 10.2 Hz), 7.85 (1H, s), 8.19 (1H, ddd, J 8.8, 4.6, 2.4 Hz), 8.66 (1H, s), 8.82 (1H, dd, J 9.1, 2.4 Hz), 8.86 (1H, s); MS ($ES^+$) m/z 350.

EXAMPLES 52 TO 77

The following Examples were prepared by the procedures shown.

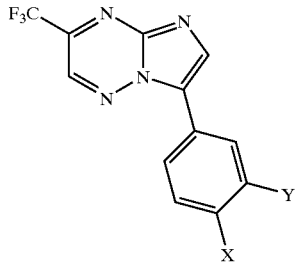

| Example | X | Y | Procedure |
|---------|---|---|-----------|

| | | | |
|---|---|---|---|
| 52 | H |  | Example 36 |
| 53 | H | 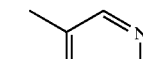 | Example 36 |
| 54 | F | 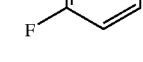 | Example 36 |
| 55 | F | 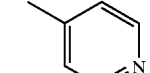 | Example 9, step d |
| 56 | F | 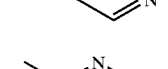 | Example 9, step d |
| 57 | F | 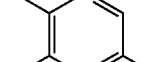 | Example 36 |
| 58 | F | 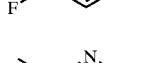 | Example 6, step e |
| 59 | F | 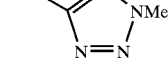 | Example 6, step e |
| 60 | F | 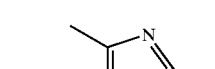 | Example 6, step e |
| 61 | F | 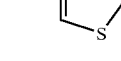 | Example 51 |
| 62 | H | 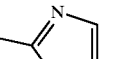 | Example 46, step b |
| 63 | H | 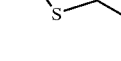 | Example 46, step b |
| 64 | H | 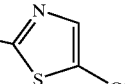 | Example 46, step b |
| 65 | H |  | Example 46, step b |
| 66 | H | 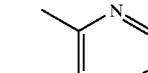 | Example 47 |
| 67 | H | 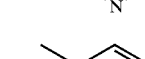 | Example 47 |
| 68 | H | 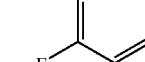 | Example 48, step b |
| 69 | H | 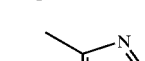 | Example 48, step b |
| 70 | F | 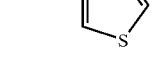 | Example 48, step b |
| 71 | H | 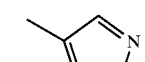 | Example 37, step e |
| 72 | H | 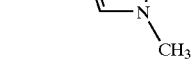 | Example 37, step e |
| 73 | H | 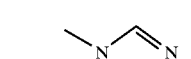 | Example 37, step e |
| 74 | H | 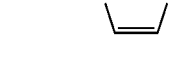 | Example 37, step e |
| 75 | H | 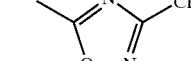 | Example 37, step e |
| 76 | H | 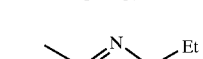 | Example 37, step e |
| 77 | H | 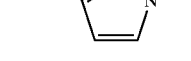 | Example 19 |

EXAMPLES 78 TO 101

The following Examples were prepared in a similar manner to Example 46 using either trifluoromethanesulfonic acid 2-fluoro-5-(3-trifluoromethylimidazo[1,2-b][1,2,4]triazin-7-yl)phenyl ester or 7-(3-bromophenyl)-3-trifluoromethylimidazo[1,2-b][1,2,4]triazine.

| Example | Name | ¹H NMR (400 MHz, DMSO-d6) |
|---|---|---|
| 78 | 7-(2'-Methoxybiphenyl-3-yl)-3-trifluoromethylimidazo[1,2-b][1,2,4]triazine | 3.79 (3 H, s), 7.08 (1 H, t, J 7.4 Hz), 7.17 (1 H, d, J 8.2 Hz), 7.37–7.42 (2 H, m), 7.58–7.65 (2 H, m), 8.14 (1 H, d, J 7.6 Hz), 8.31 (1 H, s), 8.93 (1 H, s), 9.32 (1 H, s). |
| 79 | 1-[3'-(3-Trifluoromethyl-imidazo[1,2-b][1,2,4]triazin-7-yl)-biphenyl-3-yl]ethanone | 2.68 (3 H, s), 7.69 (1 H, t, J 8 Hz), 7.74 (1 H, t, J 7.6 Hz), 7.86 (1 H, d, J 7.6 Hz), 8.00–8.05 (2 H, m), 8.24–8.27 (2 H, m), 8.51 (1 H, s), 9.02 1 H, s), 9.34 (1 H, s). |
| 80 | 3'-(3-Trifluoromethylimidazo[1,2-b][1,2,4]triazin-7-yl)biphenyl-4-caxbaldehyde | 7.75 (1 H, t, J 7.8 Hz), 7.89 (1 H, d, J 8.0 Hz), 8.01–8.07 (4 H, m), 8.29 (1 H, d, J 7.8 Hz), 8.56 (1 H, s), 9.03 (1 H, s), 9.35 (1 H, s). |
| 81 | 7-(2-Fluoro-3',4'-dimethoxy-biphenyl-5-yl)-3-trifluoromethyl-imidazo[1,2-b][1,2,4]triazine | 3.83 (6 H, s), 7.11 (1 H, d, J 8.6 Hz), 7.17–7.19 (2 H, m), 7.54 (1 H, dd, J 10.4, 8.8 Hz), 8.19–8.22 (1 H, m), 8.32–8.35 (1 H, m), 8.97 (1 H, s), 9.34 (1 H, s). |
| 82 | 1-[2'-Fluoro-5'-(3-trifluoromethyl-imdazo[1,2-b][1,2,4]triazin-7-yl)-biphenyl-3-yl]ethanone | 2.55 (3 H, s), 7.62 (1 H, dd, J 10.4, 8.8 Hz), 7.71 (1 H, t, J 7.6 Hz), 7.91 (1 H, d, J 7.6 Hz), 8.06 (1 H, d, J 7.8 Hz), 8.17 (1 H, s), 8.29–8.32 (1 H, m), 8.39–8.41 (1 H, m), 8.99 (1 H, s), 9.14 (1 H, s). |
| 83 | 3-[2'-Fluoro-5'-(3-trifluoromethyl-imidazo[1,2-b][1,2,4]triazin-7-yl)-biphenyl-3-yl]acrylic acid | 6.64 (1 H, d, J 16 Hz), 7.55–7.63 (2 H, m), 7.63–7.72 (2 H, m), 7.79 (1 H, d, J 7.7 Hz), 7.93 (1 H, s), 8.28–8.32 (1 H, m), 8.36–8.40 (1 H, m), 8.98 (1 H, s), 9.33 (1 H, s). |
| 84 | 2'-Fluoro-5'-(3-trifluoromethyl-imidazo[1,2-b][1,2,4]triazin-7-yl)-biphenyl-4-carbaldehyde | 7.63 (1 H, dd, J 10.2, 8.8 Hz), 7.89 (2 H, d, J 7.4 Hz), 8.07 (2 H, d, J 7.4 Hz), 8.29–8.35 (1 H, m), 8.39–8.44 (1 H, m), 8.99 (1 H, s), 9.34 (1 H, s). |
| 85 | 2'-Fluoro-5'-(3-trifluoromethyl-imidazo[1,2-b][1,2,4ltriazin-7-yl)-biphenyl-3-ylamine | 6.79 (1 H, d, J 7.4 Hz), 6.90 (1 H, d, J 7.4 Hz), 7.00 (1 H, s), 7.25 (1 H, t, J 7.4 Hz), 7.54 (1 H, dd, J 10.2, 8.8 Hz), 8.20–8.25 (1 H, m), 8.30–8.35 (1 H, m), 8.94 (1 H, s), 9.32 (1 H, s). |
| 86 | N-[3'-(3-trifluoromethyl-imidazo[1,2-b][1,2,4]triazin-7-yl)-biphenyl-3-yl]acetamide | 2.10 (3 H, s), 7.40–7.50 (2 H, m), 7.55–7.65 (1 H, m), 7.65–7.75 (2 H, m), 7.95 (1 H, s), 8.15–8.22 (1 H, m), 8.43 (1 H, s), 8.98 (1 H, s), 9.32 (1 H, s). |
| 87 | 3'-(3-Trifluoromethylimidazo[1,2-b][1,2,4]triazin-7-yl)biphenyl-2-carbaldehyde | 7.55–7.90 (5 H, m), 7.98 (1 H, d, J 7.1 Hz), 8.31–8.33 (2 N, m), 8.98 (1 H, s), 9.30 (1 H, s), 9.97 (1 H, s). |
| 88 | 3'-(3-Trifluoromethylimidazo[1,2-b][1,2,4]triazin-7-yl)biphenyl-4-yl]-methanol | 4.57 (2 H, s), 7.46 (2 H, d, 8 Hz), 7.65–7.85 (4 H, m), 8.18 (1 H, d, J 7.8 Hz), 8.47 (1 H, s), 9.00 (1 H, s), 9.34 (1 H, s). |
| 89 | 1-[3'-(3-Trifluoromethyl-imidazo[1,2-b][1,2,4]triazin-7-yl)-biphenyl-4-yl]ethanone | 2.55 (3 H, s), 7.74 (1 H, t, J 7.8 Hz), 7.87 (1 H, d, J 7.8 Hz), 7.94 (2 H, d, J 8.3 Hz), 8.06 (2 H, d, J 8.3 Hz), 8.27 (1 H, d, J 7.8 Hz), 8.54 (1 H, s), 9.02 (1 H, s), 9.34 (1 H, s). |
| 90 | 3-[3-(3-Trifluoromethyl-imidazo[1,2-b][1,2,4]triazin-7-yl)-phenyl]thiophene-2-carbaldehyde | 7.52 (1 H, d, J 5.0 Hz), 7.74–7.78 (2 H, m), 8.21 (1 H, d, J 5.0 Hz), 8.30–8.35 (1 H, m), 8.42 (1 H, s), 8.99 (1 H, s), 9.32 (1 H, s), 9.89 (1 H, s). |
| 91 | 3'-(3-Trifluoromethylimidazo[1,2-b][1,2,4]triazin-7-yl)biphenyl-4-carbonitrile | 7.75 (1 H, t, J 7.8 Hz), 7.87 (1 H, d, J 7.8 Hz), 7.98 (4 H, s), 8.29 (1 H, d, J 7.8 Hz), 8.52 (1 H, s), 9.02 (1 H, s), 9.34 (1 H, s). |
| 92 | 7-[3-(3,5-Dimethylisoxazol-4-yl)-4-fluorophenyl]-3-trifluoromethyl- | 2.30 (6 H, s), 7.51 (1 H, d, J 7.8 Hz), 7.70 (1 H, t, J 7.8 Hz), 8.15– |

-continued

| Example | Name | ¹H NMR (400 MHz, DMSO-d6) |
|---|---|---|
|  | imidazo[1,2-b][1,2,4]triazine | 8.25 (2 H, m), 8.93 (1 H, s), 9.31 (1 H, s). |
| 93 | 7-[3-(3-Methoxypyridazin-5-yl)-phenyl]-3-trifluoromethyl-imidazo[1,2-b][1,2,4]triazine | 4.11 (3 H, s), 7.66 (1 H, s), 7.79 (1 H, t, J 8 Hz), 8.04 (1 H, d, J 8 Hz), 8.43 (1 H, d, J 8 Hz), 8.66 (1 H, s), 9.10 (1 H, s), 9.40 (1 H, s), 9.44 (1 H, s). |
| 94 | 7-(2-Fluoro-4'-methoxybiphenyl-5-yl)-3-trifluoromethylimidazo[1,2-b][1,2,4]triazine | 3.83 (3 H, s), 7.10 (2 H, d, J 8.7 Hz), 7.50 (1 H, dd, J 8.8, 10.4 Hz), 7.58 (2 H, d, J 8.7 Hz), 8.17–8.22 (1 H, m), 8.30–8.33 (1 H, m), 8.95 (1 H, s), 9.32 (1 H, s). |
| 95 | 7-[4-Fluoro-3-(fur-2-yl)phenyl]-3-trifluoromethylimidazo[1,2-b][1,2,4]triazine | 6.70–6.74 (1 H, m), 6.95–7.05 (1 H, m), 7.58 (1 H, dd, J 8.8, 10.4 Hz), 7.90 (1 H, d, J 1.2 Hz), 8.10–8.20 (1 H, m), 8.64–8.66 (1 H, m), 8.95 (1 H, s), 9.37 (1 H, s). |
| 96 | 7-(2-Fluoro-4'-methylthiobiphenyl-5-yl)-3-trifluoromethylimidazo[1,2-b][1,2,4]triazine | 2.55 (3 H, s), 7.40 (2 H, d, J 8.4 Hz), 7.55 (1 H, dd, J 8.8, 10.4 Hz), 7.59 (2 H, d, J 8.4 Hz), 8.22–8.25 (1 H, m), 8.32–8.35 (1 H, m), 8.96 (1 H, s), 9.32 (1 H, s). |
| 97 | 7-(2-Fluoro-2'-methoxybiphenyl-5-yl)-3-trifluoromethylimidazo[1,2-b][1,2,4]triazine | 3.77 (3 H, s), 7.09 (1 H, t, J 7.4 Hz), 7.16 (1 H, d, J 7.4 Hz), 7.33 (1 H, d, J 7.4 Hz), 7.40–7.53 (2 H, m), 8.15–8.30 (2 H, m), 8.92 (1 H, s), 9.30 (1 H, s). |
| 98 | 1{5-[2-Fluoro-5-(3-trifluoromethyl-imidazo[1,2-b][1,2,4]triazin-7-yl)-phenyl]thien-2-yl}ethanone | 2.55 (3 H, s), 7.65 (1 H, dd, J 8.8, 10.4 Hz), 7.81 (1 H, d, J 4.8 Hz), 8.03 (1 H, d, J 4.8 Hz), 8.28–8.35 (1 H, m), 8.65–8.70 (1 H, m), 9.00 (1 H, s), 9.38 (1 H, s). |
| 99 | 7-(2,4'-Difluorobiphenyl-5-yl)-3-trifluoromethylimidazo[1,2-b][1,2,4]triazine | 7.37 (2 H, t, J 8.8 Hz), 7.57 (1 H, dd, J 8.8, 10.4 Hz), 7.60–7.75 (2 H, m), 8.24–8.28 (1 H, m), 8.30–8.35 (1 H, m), 8.96 (1 H, s), 9.32 (1 H, s). |
| 100 | 2'-Fluoro-5'-(3-trifluoromethyl-imidazo[1,2-b][1,2,4]triazin-7-yl)-biphenyl-4-ol | 6.91 (2 H, d, J 8.7 Hz), 7.48 (2 H, d, 8.7 Hz), 7.50 (1 H, dd, J 8.8, 10.4 Hz), 8.17–8.22 (1 H, m), 8.30–8.33 (1 H, m), 8.95 (1 H, s), 9.32 (1 H, s), 9.81 (1 H, s). |
| 101 | 7-(3'-Nitrobiphenyl-3-yl)-3-trifluoromethylimidazo[1,2 b][1,2,4]triazine | 7.77 (1 H, t, J 7.8 Hz), 7.84(1 H, t, J 7.8, 10.4 Hz), 7.91 (1 H, d, J 7.8 Hz), 8.25–8.35 (3 H, m), 8.56 (2 H, m), 9.04 (1 H, s), 9.35 (1 H, s). |

What is claimed is:

1. A compound of formula I, or a pharmaceutically acceptable salt thereof:

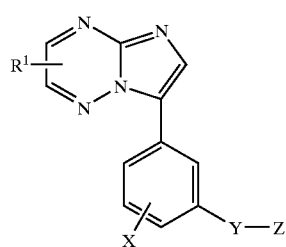

(I)

wherein:

X represents hydrogen or halogen;

Y represents a chemical bond, an oxygen atom, or a —NH-linkage;

Z represents an optionally substituted aryl or heteroaryl group;

$R^1$ represents hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$ alkyl), indanyl, phenyl, phenyl($C_{1-6}$ alkyl), a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$; and $R^a$ and $R^b$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$ alkyl), indanyl, phenyl, phenyl($C_{1-6}$ alkyl), or a heterocyclic group.

2. The compound of claim 1 of the formula IIA, or a pharmaceutically acceptable salt thereof:

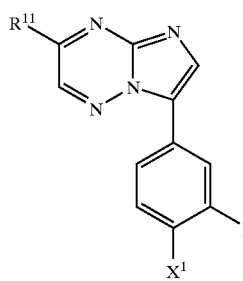

(IIA)

wherein:

X$^1$ represents hydrogen or fluoro;

Z represents an optionally substituted aryl or heteroaryl group;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, heteroaryl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl.

3. The compound of claim 2 of the formula IIB, or a pharmaceutically acceptable salt thereof:

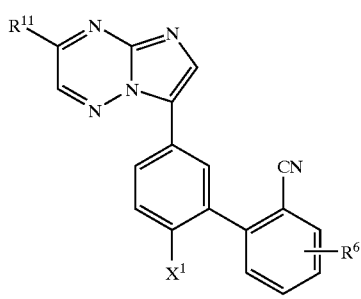

(IIB)

wherein:

X$^1$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, heteroaryl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl; and R$^6$ represents hydrogen.

4. The compound of claim 2 of the formula IIC, or a pharmaceutically acceptable salt thereof:

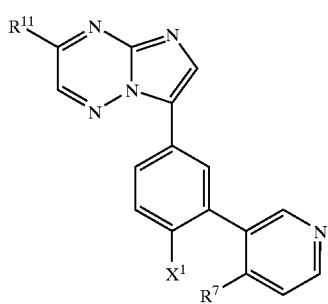

(IIC)

X$^1$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, heteroaryl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl; and R$^7$ represents hydrogen, halogen or C$_{1-6}$ alkyl.

5. The compound of claim 2 of the formula IID, or a pharmaceutically acceptable salt thereof:

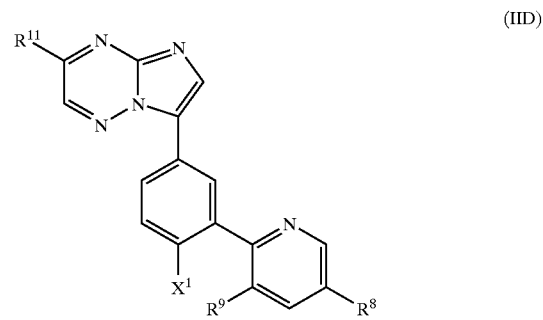

(IID)

wherein

X$^1$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, heteroaryl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl;

R$^8$ represents hydrogen or fluoro; and

R$^9$ represents hydrogen, fluoro or cyano.

6. The compound of claim 5 wherein R$^8$ and R$^9$ both represent fluoro.

7. The compound of claim 2 wherein R$^1$ represents fluoro.

8. The compound of claim 2 wherein R$^{11}$ represents 2-hydroxyprop-2-yl.

9. The compound of claim 1 of the formula IIE, or a pharmaceutically acceptable salt thereof:

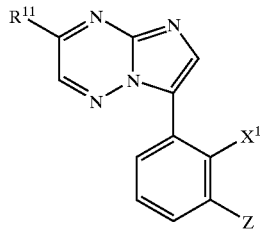

(IIE)

wherein:

Z represents an optionally substituted aryl or heteroaryl group;

X$^1$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, heteroaryl, halogen, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl.

10. A compound selected from:

3'-(2-methylimidazo[1,2-b][1,2,4]triazin-7-yl)biphenyl-2-carbonitrile,

3'-(3-methylimidazo[1,2-b][1,2,4]triazin-7-yl)biphenyl-2-carbonitrile;

2-fluoro-5'-(3-trifluoromethylimidazo[1,2-b][1,2,4]triazin-7-yl)biphenyl-2-carbonitrile;

or a pharmaceutically acceptable salt thereof.

11. A compound selected from:

3-(1-fluoro-1-methylethyl)-7-[4-fluoro-3-(pyridin-3-yl)phenyl]imidazo[1,2-b][1,2,4]triazine;

2'-fluoro-5'-(imidazo[1,2-b][1,2,4]triazin-7-yl)biphenyl-2-carbonitrile;

7-[4-fluoro-3-(pyridin-2-yl)phenyl]-3-trifluoromethylimidazo[1,2-b][1,2,4]triazine;

2'-fluoro-3'-(3-trifluoromethylimidazo[1,2-b][1,2,4]triazin-7-yl)biphenyl-2-carbonitrile;

2-[2-fluoro-5-(3-trifluoromethylimidazo[1,2-b]triazin-7-yl)phenyl]-niconitrile;

3-(1,1-difluoroethyl)-7-[4-fluoro-3-(pyridin-3-yl)phenyl]imidazo[1,2-b][1,2,4]triazine;

3-tert-butyl-7-[4-fluoro-3-(pyridin-3-yl)phenyl]imidazo[1,2-b][1,2,4]-triazine;

3-tert-butyl-7-[4-fluoro-3-(pyridin-2-yl)phenyl]imidazo[1,2-b][1,2,4]-triazine;

2-{7-[4-fluoro-3-(pyridin-3-yl)phenyl]imidazo[1,2-b][1,2,4]triazin-3-yl}propan-2-ol;

2-{7-[4-fluoro-3-(pyridin-4-yl)phenyl]imidazo[1,2-b][1,2,4]triazin-3-yl}propan-2-ol;

2'-fluoro-5'-[3-(1-hydroxy-1-methylethyl)imidazo[1,2-b][1,2,4]triazin-7-yl]biphenyl-2-carbonitrile;

2-{7-[2-fluoro-3-(pyridin-4-yl)phenyl]imidazo[1,2-b][1,2,4]triazin-3-yl}propan-2-ol;

or a pharmaceutically acceptable salt thereof.

12. A compound selected from:

2-{2-fluoro-5-[3-(1-hydroxy-1-methylethyl)imidazol[1,2-b][1,2,4]triazin-7-yl]phenyl}nicotinonitrile;

7-[6-fluoro-2'-(methanesulfonyl)biphenyl-3-yl]-3-trifluoromethyl-imidazo[1,2-b][1,2,4]triazine;

3'-[3-(1-hydroxy-1-methylethyl)imidazo[1,2-b][1,2,4]triazin-7-yl]biphenyl-2-carbonitrile;

2-{7-[3-(3,5-difluoropyridin-2-yl)-4-fluorophenyl]imidazo[1,2-b][1,2,4]triazin-3-yl}propan-2-ol;

4-{2-fluoro-5-[3-(1-hydroxy-1-methylethyl)imidazo[1,2-b][1,2,4]triazin-7-yl]phenyl}nicotinonitrile;

6,2'-difluoro-5'-[3-(1-fluoro-1-methylethyl)imidazo[1,2-b][1,2,4]triazin-7-yl]biphenyl-2-carbonitrile;

7-[3-(3,5-difluoropyridin-2-yl)-4-fluorophenyl]-3-(1-fluoro-1-methylethyl)-imidazo[1,2-b][1,2,4]triazine;

4,6,2'-trifluoro-5'-[3-(1-fluoro-1-methylethyl)imidazo[1,2-b][1,2,4]triazin-7-yl]biphenyl-2-carbonitrile;

2-{7-[4-fluoro-3-(3-fluoropyridin-2-yl)phenyl]imidazo[1,2-b][1,2,4]triazin-3-yl}propan-2-ol;

2-{7-[4-fluoro-3-(5-fluoropyridin-2-yl)phenyl]imidazo[1,2-b][1,2,4]triazin-3-yl}propan-2-ol;

2-[7-(4-fluoro-3-(pyridin-2-yl)phenyl)imidazo[1,2-b][1,2,4]triazin-3-yl]-propan-2-ol;

2-[7-(4-fluoro-3-(pyridazin-3-yl)phenyl)imidazo[1,2-b][1,2,4]triazin-3-yl]-propan-2-ol;

2-[7-(4-fluoro-3-(pyrimidin-4-yl)phenyl)imidazo[1,2-b][1,2,4]triazin-3-yl]-propan-2-ol;

2-[7-(4-fluoro-3-(pyridazin-4-yl)phenyl)imidazo[1,2-b][1,2,4]triazin-3-yl]-propan-2-ol;

4-{2-fluoro-5-[3-(1-hydroxy-1-methylethyl)imidazo[1,2-b][1,2,4]triazin-7-yl]phenyl}pyrimidine-5-carbonitrile;

2-{7-[3-(3,5-difluoropyridin-2-yl)phenyl]imidazo[1,2-b][1,2,4]triazin-3-yl}-propan-2-ol;

7-[3-(1-methyl-1H-pyrazol-3-yl)phenyl]-3-trifluoromethylimidazo[1,2-b][1,2,4]triazine;

7-[4-chloro-3-(pyridin-3-yl)phenyl]-3-trifluoromethylimidazo[1,2-b][1,2,4]-triazine;

7-[3-(pyridin-3-yl)phenyl]-3-trifluoromethylimidazo[1,2-b][1,2,4]triazine;

7-[3-([1,2,4]triazol-1-yl)phenyl]-3-trifluoromethylimidazo[1,2-b][1,2,4]triazine;

7-[3-(2-methyl-2H-[1,2,3]triazol-4-yl)phenyl]-3-trifluoromethylimidazo[1,2-b][1,2,4]triazine;

7-[3-(1-methyl-1H-[1,2,4]triazol-3-yl)phenyl]-3-trifluoromethylimidazo[1,2-b][1,2,4]triazine;

7-[4-fluoro-3-(imidazol-1-yl)phenyl]-3-trifluoromethylimidazo[1,2-b][1,2,4]triazine;

7-[4-fluoro-3-(pyridin-3-yl)phenyl]-3-trifluoromethylimidazo[1,2-b][1,2,4]triazine;

7-[4-fluoro-3-(5-fluoropyridin-2-yl)phenyl]-3-trifluoromethylimidazo[1,2-b][1,2,4]triazine;

7-[3-(pyrrol-1-yl)phenyl]-3-trifluoromethylimidazo[1,2-b][1,2,4]triazine;

7-[3-(pyridin-4-yl)phenyl]-3-trifluoromethylimidazo[1,2-b][1,2,4]triazine;

7-[3-(thiazol-2-yl)phenyl]-3-trifluoromethylimidazo[1,2-b][1,2,4]triazine;

7-[3-(5-fluoropyridin-2-yl)phenyl]-3-trifluoromethylimidazo[1,2-b][1,2,4]triazine;

7-[4-fluoro-3-(pyrazol-1-yl)phenyl]-3-trifluoromethylimidazo[1,2 b][1,2,4]triazine;

7-[4-fluoro-3-([1,2,4]triazol-1-yl)phenyl]-3-trifluoromethylimidazo[1,2-b][1,2,4]triazine;

7-[4-fluoro-3-(oxazol-2-yl)phenyl]-3-trifluoromethylimidazo[1,2-b][1,2,4]triazine;

7-[3-(fur-2-yl)phenyl]-3-trifluoromethylimidazo[1,2-b][1,2,4]triazine;

7-[3-(2-methyltetrazol-5-yl)phenyl]-3-trifluoromethylimidazo[1,2-b][1,2,4]triazine;

7-[4-fluoro-3-(4-fluoropyridin-3-yl)phenyl]-3-trifluoromethylimidazo[1,2-b][1,2,4]triazine;

7-[4-fluoro-3-(pyridin-4-yl)phenyl]-3-trifluoromethylimidazo[1,2-b][1,2,4]triazine;

7-[3-(3,5-difluoropyridin-2-yl)-4-fluorophenyl]-3-trifluoromethyl-imidazo[1,2-b][1,2,4]triazine;

7-[4-fluoro-3-(2-methyltetrazol-5-yl)phenyl]-3-trifluoromethylimidazo[1,2-b][1,2,4]triazine;

7-[4-fluoro-3-(thiazol-4-yl)phenyl]-3-trifluoromethylimidazo[1,2-b][1,2,4]triazine;

7-[4-fluoro-3-(5-nitrothiazol-2-yl)phenyl]-3-trifluoromethylimidazo[1,2-b][1,2,4]triazine;

7-[3-(5-dimethylaminocarbonylthiazol-2-yl)-4-fluorophenyl]3-trifluoromethylimidazo[1,2-b][1,2,4]triazine;

7-[4-fluoro-3-(thiazol-2-yl)phenyl]-3-trifluoromethylimidazo[1,2-b][1,2,4]triazine;

7-[3-(thien-2-yl)phenyl]-3-trifluoromethylimidazo[1,2-b][1,2,4]triazine;

7-[3-(thien-3-yl)phenyl]-3-trifluoromethylimidazo[1,2-b][1,2,4]triazine;

7-[3-(fur-3-yl)phenyl]-3-trifluoromethylimidazo[1,2-b][1,2,4]triazine;

7-[3-(4-methylpyridin-2-yl)phenyl)-3-trifluoromethylimidazo[1,2-b][1,2,4]triazine;

7-[3-(pyridin-2-yl)phenyl]-3-trifluoromethylimidazo[1,2-b][1,2,4]triazine;

7-[3-(pyrazin-2-yl)phenyl]-3-trifluoromethylimidazo[1,2-b][1,2,4]triazine;

7-[3-(4-fluoropyridin-2-yl)phenyl]-3-trifluoromethylimidazo[1,2-b][1,2,4]triazine;

7-[3-(thiazol-4-yl)phenyl]-3-trifluoromethylimidazo[1,2-b][1,2,4]triazine;

7-[4-fluoro-3-(1-methylpyrazol-4-yl)phenyl]-3-trifluoromethylimidazo[1,2-b][1,2,4]triazine;

7-[3-(imidazol-1-yl)phenyl]-3-trifluoromethylimidazo[1,2-b][1,2,4]triazine;

7-[3-(3-methyl-[1,2,4]oxadiazol-5-yl)phenyl]-3-trifluoromethylimidazo[1,2-b][1,2,4]triazine;

7-[3-(1-ethylpyrazol-3-yl)phenyl]-3-trifluoromethylimidazo[1,2-b][1,2,4]triazine;

7-(3-(5-methyl-[1,2,4]oxadiazol-2-yl)phenyl]-3-trifluoromethylimidazo[1,2-b][1,2,4]triazine;

7-[3-([1,2,3]thiadiazol-4-yl)phenyl]-3-trifluoromethylimidazo[1,2-b][1,2,4]triazine;

7-[3-(5-methyl-[1,2,4]thiadiazol-2-yl)phenyl]-3-trifluoromethylimidazo[1,2-b][1,2,4]triazine;

7-[-2-fluoro-3-(pyridin-4-yl)phenyl]-3-trifluoromethylimidazo[1,2-b][1,2,4]triazine;

7-(2'-methoxybiphenyl-3-yl)-3-trifluoromethylimidazo[1,2-b][1,2,4]triazine;

1-[3'-(3-trifluoromethylimidazo[1,2-b][1,2,4]triazin-7-yl)biphenyl-3-yl]ethanone;

3'-(3-trifluoromethylimidazo[1,2-b][1,2,4]triazin-7-yl)biphenyl-4-carbaldehyde;

7-(2-fluoro-3',4'-dimethoxybiphenyl-5-yl)-3-trifluoromethylimidazo[1,2-b][1,2,4]triazine;

1-[2'-fluoro-5'-(3-trifluoromethylimidazo[1,2-b][1,2,4]triazin-7-yl)biphenyl-3-yl]ethanone;

3-[2'-fluoro-5'-(3-trifluoromethylimidazo[1,2-b][1,2,4]triazin-7-yl)biphenyl-3-yl]acrylic acid;

2'-fluoro-5'-(3-trifluoromethylimidazo[1,2-b][1,2,4]triazin-7-yl)biphenyl-4-carbaldehyde;

2'-fluoro-5'-(3-trifluoromethylimidazo[1,2-b][1,2,4]triazin-7-yl)biphenyl-3-ylamine;

N-[3'-(3-trifluoromethylimidazo[1,2-b][1,2,4]triazin-7-yl)biphenyl-3-yl]acetamide;

3'-(3-trifluoromethylimidazo[1,2-b][1,2,4)triazin-7-yl)biphenyl-2-carbaldehyde;

[3'-(3-trifluoromethylimidazo[1,2-b][1,2,4]triazin-7-yl)biphenyl-4-yl)-methanol;

1-[3'-(3-trifluoromethylimidazo[1,2-b][1,2,4]triazin-7-yl)biphenyl-4-yl]-ethanone;

3-[3-(3-trifluoromethylimidazo[1,2-b][1,2,4]triazin-7-yl)phenyl]thiophene-2-carbaldehyde;

3'-(3-trifluoromethylimidazo[1,2-b]]1,2,4]triazin-7-yl)biphenyl-4-carbonitrile;

7-[3-(3,5-dimethylisoxazol-4-yl)-4-fluorophenyl]-3-trifluoromethyl-imidazo[1,2-b][1,2,4]triazine;

7-[3-(3-methoxypyridazin-5-yl)phenyl]-3-trifluoromethylimidazo[1,2-b][1,2,4]triazine;

7-(2-fluoro-4'-methoxybiphenyl-5-yl)-3-trifluoromethylimidazo[1,2-b][1,2,4]triazine;

7-[4-fluoro-3-(fur-2-yl)phenyl]-3-trifluoromethylimidazo[1,2-b][1,2,4]triazine;

7-(2-fluoro-4'-methylthiobiphenyl-5-yl)-3-trifluoromethylimidazo[1,2-b][1,2,4]triazine;

7-(2-fluoro-2'-methoxybiphenyl-5-yl)-3-trifluoromethylimidazo[1,2-b][1,2,4]triazine;

1-{5-[2-fluoro-5-(3-trifluoromethylimidazo[1,2-b][1,2,4]triazin-7-yl)-phenyl]thien-2-yl}ethanone;

7-(2,4'-difluorobiphenyl-5-yl)-3-trifluoromethylimidazo[1,2-b][1,2,4]triazine;

2'-fluoro-5'-(3-trifluoromethylimidazo[1,2-b][1,2,4]triazin-7-yl)biphenyl-4-ol;

7-(3'-nitrobiphenyl-3-yl)-3-trifluoromethylimidazo[1,2-b][1,2,4]triazine;

or a pharmaceutically acceptable salt thereof.

13. A pharmaceutical composition comprising a compound of claim 1, or a pharmaceutically acceptable salt thereof, and a pharmaceutically acceptable carrier.

14. A method for the treatment of anxiety which comprises administering to a patient in need of such treatment an effective amount of a compound of claim 1 or a pharmaceutically acceptable salt thereof.

15. A method for the treatment of convulsions which comprises administering to a patient in need of such treatment an effective amount of a compound of claim 1 or a pharmaceutically acceptable salt thereof.

16. A method for the treatment of a cognitive disorder which comprises administering to a patient in need of such treatment an effective amount of a compound of claim 1 or a pharmaceutically acceptable salt thereof.

17. A process for the preparation of a compound of claim 1, which comprises:

(A) reacting a compound of formula III with a compound of formula IV:

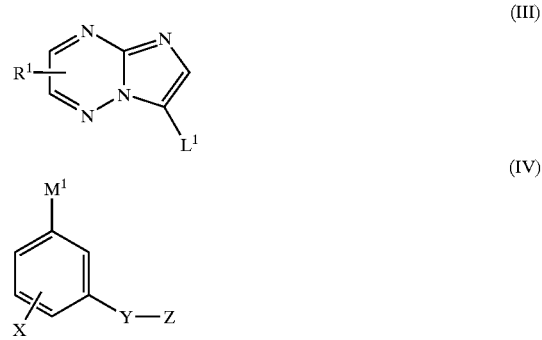

wherein X, Y, Z and $R^1$ are as defined in claim 1, $L^1$ represents a suitable leaving group, and $M^1$ represents a boronic acid moiety —$B(OH)_2$ or a cyclic ester thereof formed with an organic diol, or $M^1$ represents —$Sn(Alk)_3$ in which Alk represents a $C_{1-6}$ alkyl group; in the presence of a transition metal catalyst; or (B) reacting a compound of formula V with a compound of formula VI:

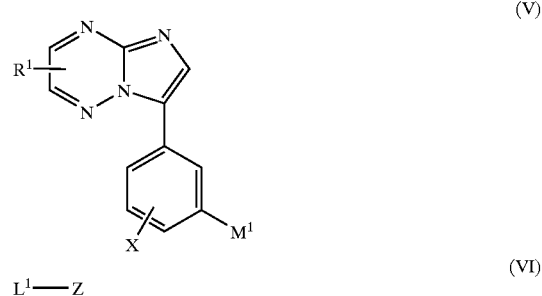

wherein X, Z and $R^1$ are as defined in claim 1, and $L^1$ and $M^1$ are as defined above; in the presence of a transition metal catalyst; or (C) reacting a compound of formula VI as defined above with a compound of formula VII:

(VII)

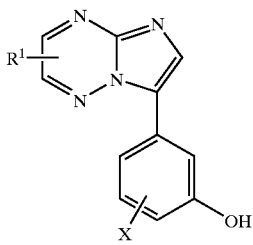

wherein X and R¹ are as defined in claim 1; or (D) reacting a compound of formula VI as defined above with a compound of formula VIII:

(VIII)

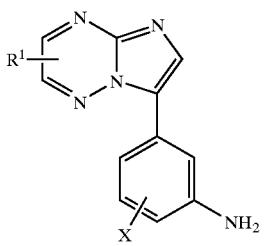

wherein X and R¹ are as defined in claim 1; or (E) reacting a compound of formula XII with a compound of formula XIII:

(XII)

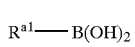

(XIII)

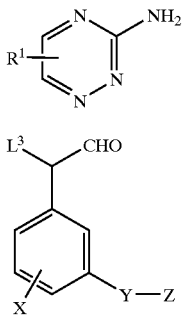

wherein X, Y, Z and R¹ are as defined in claim 1, and L³ represents a suitable leaving group; or (F) reacting a compound of formula XIV with a compound of formula XV:

(XIV)

$R^{a1}$—B(OH)₂

(XV)

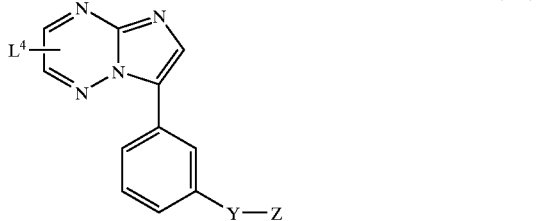

wherein Y and Z are as defined in claim 1, $R^{1a}$ represents an aryl or heteroaryl moiety, and L⁴ represents a suitable leaving group; in the presence of a transition metal catalyst; or (G) reacting a compound of formula M¹-Z with a compound of formula VA:

(VA)

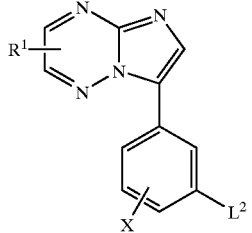

wherein X, Z and R¹ are as defined in claim 1, M¹ is as defined above, and L² represents a suitable leaving group; in the presence of a transition metal catalyst; or (H) reacting a compound of formula VIII as defined above with 2,5-dimethoxytetrahydrofuran.

* * * * *